US011033629B2

(12) United States Patent
Wilson et al.

(10) Patent No.: US 11,033,629 B2
(45) Date of Patent: Jun. 15, 2021

(54) ORAL FORMULATIONS OF KAPPA OPIOID RECEPTOR AGONISTS

(71) Applicant: Cara Therapeutics, Inc., Stamford, CT (US)

(72) Inventors: Bryan R. Wilson, Brewster, NY (US); Stephen J. O'Connor, Guilford, CT (US)

(73) Assignee: Cara Therapeutics, Inc., Stamford, CT (US)

( * ) Notice: Subject to any disclaimer, the term of this patent is extended or adjusted under 35 U.S.C. 154(b) by 0 days.

(21) Appl. No.: 16/570,333

(22) Filed: Sep. 13, 2019

(65) Prior Publication Data

US 2020/0085961 A1    Mar. 19, 2020

Related U.S. Application Data

(60) Provisional application No. 62/731,802, filed on Sep. 14, 2018.

(51) Int. Cl.

| | | |
|---|---|---|
| *A61K 38/07* | (2006.01) | |
| *A61K 47/54* | (2017.01) | |
| *A61K 31/40* | (2006.01) | |
| *A61K 31/485* | (2006.01) | |
| *A61K 47/14* | (2017.01) | |
| *A61K 9/48* | (2006.01) | |
| *A61K 47/18* | (2017.01) | |
| *A61K 9/107* | (2006.01) | |
| *A61K 38/08* | (2019.01) | |
| *A61K 47/64* | (2017.01) | |
| *A61K 47/26* | (2006.01) | |

(52) U.S. Cl.
CPC ............ *A61K 47/545* (2017.08); *A61K 9/107* (2013.01); *A61K 9/4891* (2013.01); *A61K 31/40* (2013.01); *A61K 31/485* (2013.01); *A61K 38/07* (2013.01); *A61K 38/08* (2013.01); *A61K 47/14* (2013.01); *A61K 47/183* (2013.01); *A61K 47/186* (2013.01); *A61K 47/26* (2013.01); *A61K 47/64* (2017.08)

(58) Field of Classification Search
CPC ...... A61K 47/545; A61K 38/07; A61K 31/40; A61K 31/485; A61K 47/14; A61K 9/4891; A61K 47/183; A61K 47/186; A61K 9/107; A61K 38/08; A61K 47/64; A61K 47/26; A61K 9/4866
See application file for complete search history.

(56) References Cited

U.S. PATENT DOCUMENTS

| | | | | |
|---|---|---|---|---|
| 5,804,557 A | * | 9/1998 | Cleland ................ | A61K 9/1694 514/11.3 |
| 6,187,330 B1 | * | 2/2001 | Wang .................... | A61K 9/0024 424/426 |
| 7,785,631 B2 | | 8/2010 | Roser et al. | |
| 7,956,028 B2 | | 6/2011 | Garigapati et al. | |
| 8,217,007 B1 | * | 7/2012 | Schteingart ............ | A61P 35/00 514/18.4 |
| 8,377,863 B2 | | 2/2013 | Stern et al. | |
| 8,592,366 B2 | | 11/2013 | Stern et al. | |
| 8,664,178 B2 | | 3/2014 | Stern et al. | |
| 9,302,010 B2 | | 4/2016 | Petrelski et al. | |
| 9,399,017 B2 | | 7/2016 | Stern et al. | |
| 2015/0150935 A1 | * | 6/2015 | Chalmers ............... | A61K 31/40 514/16.6 |
| 2018/0344831 A1 | | 12/2018 | Tanaka et al. | |
| 2019/0111001 A1 | | 4/2019 | Feng et al. | |

OTHER PUBLICATIONS

Maher et al (Advanced Drug Delivery Reviews, 2016, 106, 277-319) (Year: 2016).*
Niu et al (Advanced Drug Delivery Reviews, 2016, 106, 337-354) (Year: 2016).*
Leonard et al (Expert Opin Drug Deliv, 2006, 3(5) 685-692) (Year: 2006).*
Jain et al (Protein Science, 2009, vol. 18, 24-36) (Year: 2009).*
Maher et al (Pharm.Pat.Anal., 2014, 3(3), 313-336) (Year: 2014).*
Ohtake et al (Journal of Pharmaceutical Sciences, vol. 100, No. 6, May 2011, 2020-2053) (Year: 2011).*
Bruce J. Aungst, Absorption Enhancers: Applications and Advances. AAPS Journal, vol. 14, No. 1, Mar. 2012 (#2011).
Sarwar Beg et al., Bioavailability Enhancement Strategies: Basics, Formulation Approaches and Regulatory Considerations. Current Drug Delivery, 2011, 8, 000-000.
EFSA Panel on Food Additives and Nutrient Sources added to Food (ANS), Alicja Mortensen et al., Re-evaluation of fatty acids (E 570) as a food additive. doi: 10.2903/j.efsa.2017.4785; Apr. 4, 2017.
GRAS Notice (GRN) No. 449 http://www.fda.gov/Food/FoodIngredientsPackaging/GenerallyRecognizedasSafeGRAS/GRASListings/default.htm Robert Sloan, Lonza Inc., Re: Notification of the GRAS Determination of Medium Chain Triglycerides When Added Directly to Human Food, Nov. 20, 2012.
Maher, Sam et al., Safety and efficacy of sodium caprate in promoting oral drug absorption : from in vitro to the clinic. Advanced Drug Delivery Reviews, 61 (15): 1427-1449. Dec. 17, 2009.

(Continued)

*Primary Examiner* — Sudhakar Katakam
(74) *Attorney, Agent, or Firm* — Algis Anilionis; Anilionis IP Law, LLC

(57) ABSTRACT

The invention provides formulations for oral delivery of a therapeutic agent wherein the formulation comprises a kappa opioid receptor agonist and an absorption enhancer, the absorption enhancer includes a medium chain fatty acid or a salt of a medium chain fatty acid; and a medium chain fatty acid glyceride. The kappa opioid receptor agonist may be embedded in an oligosaccharide, such as trehalose. Also provided are capsules containing the oral formulations of the kappa opioid receptor agonists and the absorption enhancer of the invention and methods use of these formulations for the prophylaxis and treatment of variety of kappa opioid receptor-associated diseases and conditions such as pain, pruritus and inflammation; the method comprising administering to the mammal the formulation comprising the kappa opioid receptor agonist and an absorption enhancer.

20 Claims, 14 Drawing Sheets

(56) References Cited

OTHER PUBLICATIONS

Hetal N. Prajapati et al. A Comparative Evaluation of Mono-, Di- and Triglyceride of Medium Chain Fatty Acids by Lipid/Surfactant/Water Phase Diagram, Solubility Determination and Dispersion Testing for Application in Pharmaceutical Dosage Form Development. Pharm Res (2012) 29:285-305 DOI 10.1007/s11095-011-0541-3 Published online: Aug. 23, 2011.

* cited by examiner

ORAL FORMULATIONS OF KAPPA OPIOID RECEPTOR AGONISTS

FIELD OF THE INVENTION

The invention relates to a formulation for oral delivery of a therapeutic agent. The formulation includes a therapeutic agent in the form of an active pharmaceutical ingredient (API), a medium chain fatty acid or a salt of a medium chain fatty acid, and a medium chain fatty acid glyceride. Suitable active pharmaceutical ingredients include kappa opioid receptor agonists such as D-amino acid peptide amides.

The invention further relates to methods of prophylaxis or treatment of kappa opioid receptor-associated diseases and conditions in a human patient or other mammal, the method comprising administering to the patient or the mammal the oral formulation of the invention.

BACKGROUND

Kappa opioid receptor agonists are a new class of therapeutic agents that have unique physicochemical properties leading to the need for new formulations for efficient delivery and sufficient bioavailability for efficacy of prophylaxis or treatment of kappa opioid receptor-associated diseases and conditions. New Kappa include the synthetic peptide amides disclosed in U.S. Pat. Nos. 7,402,564, 7,713,937 and 7,842,662 to Schteingart et al. and asimadoline (N-[(1S)-2-[(3S)-3-hydroxypyrrolidin-1-yl]-1-phenylethyl]-N-methyl-2,2-diphenylacetamide), as well as nalfurafine ((2E)-N-[(5α, 6β)-17-(cyclopropylmethyl)-3,14-dihydroxy-4,5-epoxymorphinan-6-yl]-3-(3-furyl)-N-methylacrylamide).

Pharmaceutical formulations can be tailored for different delivery routes, such as for intra venous or intra muscular injection, for topical application, or for oral administration. Each of these formulations must meet the particular stability requirements that permit storage for a period of time after manufacture and before administration to the patient. In certain circumstances the different components of the formulation may interact over time resulting in a reduction in long term stability. Suitable formulations and additives for maximizing bioavailability of particular kappa opioid receptor agonists are unpredictable.

SUMMARY OF THE INVENTION

The present invention provides a formulation for oral delivery of a therapeutic agent that includes a kappa opioid receptor agonist and an absorption enhancer. In one embodiment, the formulation of the invention includes a medium chain fatty acid or a salt of a medium chain fatty acid, and a medium chain fatty acid glyceride as absorption enhancers suitable for optimizing uptake of the kappa opioid receptor agonist from the gastrointestinal system and thereby enhancing its biological activity. In one alternative, the invention provides an oral formulation including a medium chain fatty acid or a salt of a medium chain fatty acid, and no medium chain fatty acid glyceride. In another alternative, the invention provides an oral formulation including a medium chain fatty acid glyceride and no medium chain fatty acid or a salt of a medium chain fatty acid.

The invention further provides a bioactive composition that includes a biologically active peptide embedded in an oligomeric saccharide forming a particle including the stabilized biologically active peptide. The biologically active peptide can be any suitable biologically active peptide, such as for instance a biologically active peptide that includes one or more D-amino acids. In one embodiment, the biologically active peptide that includes one or more D-amino acids is a kappa opioid receptor agonist. The biologically active peptide kappa opioid receptor agonist that includes one or more D-amino acids can be any suitable biologically active peptide kappa opioid receptor agonist that includes one or more D-amino acids such as for instance, and without limitation, any of the peptide kappa opioid receptor agonists disclosed in U.S. Pat. No. 7,402,564. In one embodiment, the biologically active peptide kappa opioid receptor agonist that includes one or more D-amino acids is (D-Phe-D-Phe-D-Leu-D-Lys-[ω(4-aminopyperidine-4carboxylic acid)]-OH also known as CR845, as disclosed and identified as compound 2 in U.S. Pat. No. 7,402,564.

In another embodiment of the invention, the formulation for oral delivery of a therapeutic agent, interchangeably referred to herein as the oral formulation of the invention, includes a peptide amide kappa opioid receptor agonist which contains one or more D-amino acids and a medium chain fatty acid or a salt of a medium chain fatty acid, and a medium chain fatty acid glyceride as absorption enhancers. The peptide amide kappa opioid receptor agonist which contains one or more D-amino acids can be any suitable peptide amide containing at least one D-amino acid, such as for instance, but not limited to, any of the synthetic peptide amides disclosed in U.S. Pat. Nos. 7,402,564, 7,713,937 and 7,842,662 to Schteingart et al., the entire disclosures of which are herein incorporated by reference.

In another embodiment, the bioactive composition includes a biologically active peptide embedded in an oligomeric saccharide forming a particle including the stabilized biologically active peptide, wherein the oligomeric saccharide includes a disaccharide. The disaccharide can be any suitable disaccharide, such as for instance, a disaccharide that includes one or more glucose monomers. In one embodiment, the disaccharide includes trehalose, the 1,1-α-glycoside linked glucose dimer. In a particular embodiment the disaccharide can consist entirely of trehalose.

In one embodiment, the bioactive composition includes a biologically active peptide embedded in an oligomeric saccharide to form a particle including the stabilized biologically active peptide, wherein the oligomeric saccharide enhances the stability of the biologically active peptide over at least a year at 25° C.

In another embodiment of the oral formulation of the invention, the oral formulation includes a peptide amide kappa opioid receptor agonist and one or more absorption enhancers, wherein the peptide amide kappa opioid receptor agonist has a structure of the following formula:

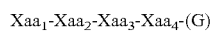  Formula I

In another embodiment of the oral formulation of the invention, the oral formulation includes a peptide amide kappa opioid receptor agonist and one or more absorption enhancers, wherein the peptide amide kappa opioid receptor agonist is CR845 having the structure of the following formula:

Formula II

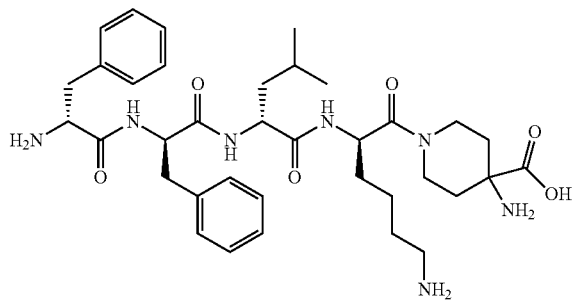

D-Phe-D-Phe-D-Leu-D-Lys-[ω(4-aminopiperidine-4-carboxylic acid)]-OH.

In still another embodiment, the oral formulation of the invention includes a peptide amide kappa opioid receptor agonist that includes one or more D-amino acids, and an absorption enhancer; wherein the synthetic peptide amide including one or more D-amino acids is CR845 and the absorption enhancer includes a medium chain fatty acid or a pharmaceutically acceptable salt of a medium chain fatty acid, and a medium chain fatty acid glyceride.

The present invention further provides methods of use of a formulation for oral delivery of a therapeutic agent that includes a kappa opioid receptor agonist and an absorption enhancer for the prophylaxis or treatment of kappa opioid receptor-associated diseases and conditions in a human patient or other mammal, the method comprising administering to the patient or the mammal the oral formulation of the invention. In one embodiment, the formulation of the invention includes a medium chain fatty acid or a salt of a medium chain fatty acid, and a medium chain fatty acid glyceride as absorption enhancers suitable for optimizing uptake of the kappa opioid receptor agonist from the gastrointestinal system and thereby enhancing its biological activity.

DETAILED DESCRIPTION OF THE INVENTION

Figure 1:
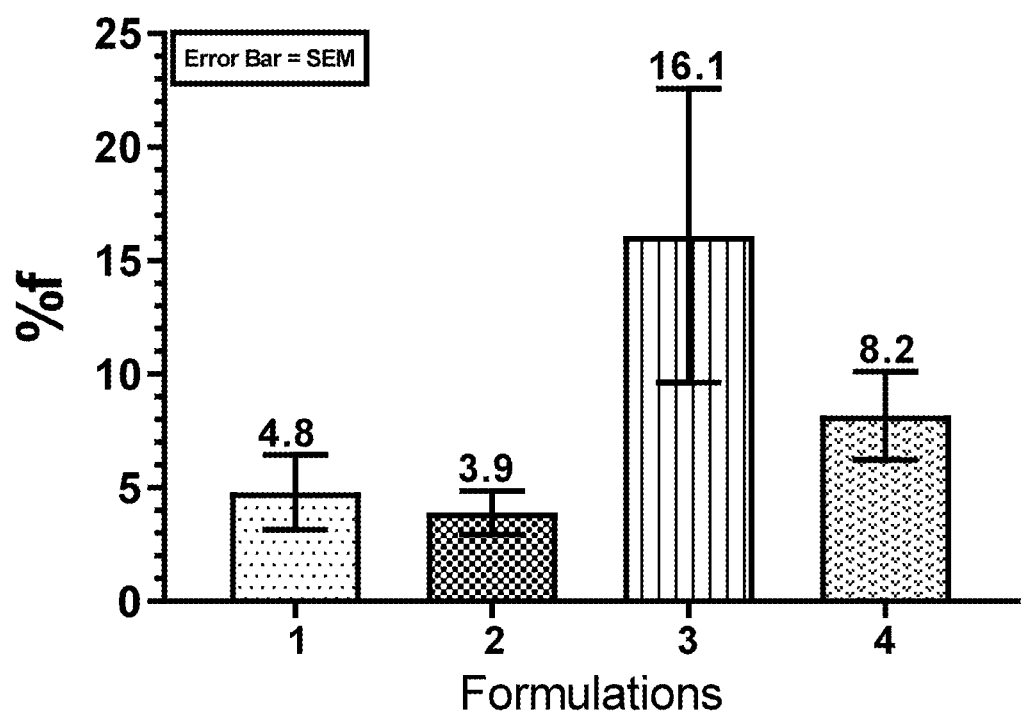
FIG. 1: Bioavailability of CR845 post oral administration to canines (n=8) of a formulation containing (1) 1.6 mg spray dried CR845.HCl in 90% Miglyol® 812, 10% sodium caprate; (2) 1.6 mg crystallized CR845.HCl in 90% Miglyol® 812, 10% sodium caprate; (3) 1.6 mg spray dried CR845.HCl in 90% Miglyol® 812, 10% capric acid; (4) 1.6 mg spray dried CR845.HCl in 70% Miglyol® 812, 30% capric acid.
Figure 2:
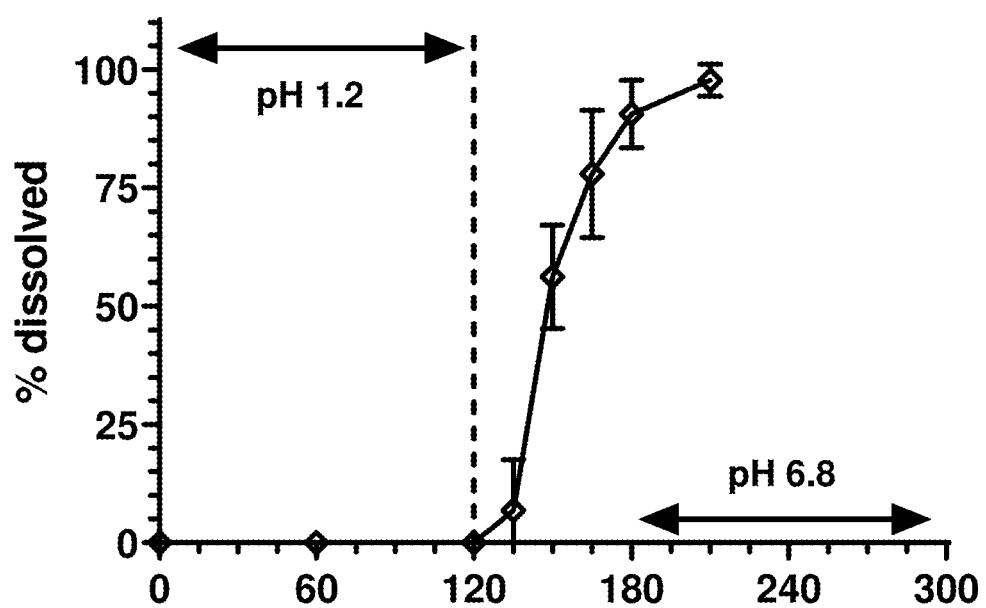
FIG. 2: Dissolution profile of formulation 1 containing 1.6 mg spray dried CR845.HCl in 90% Miglyol® 812, 10% sodium caprate on a scale of 0-300 mins.
Figure 3:
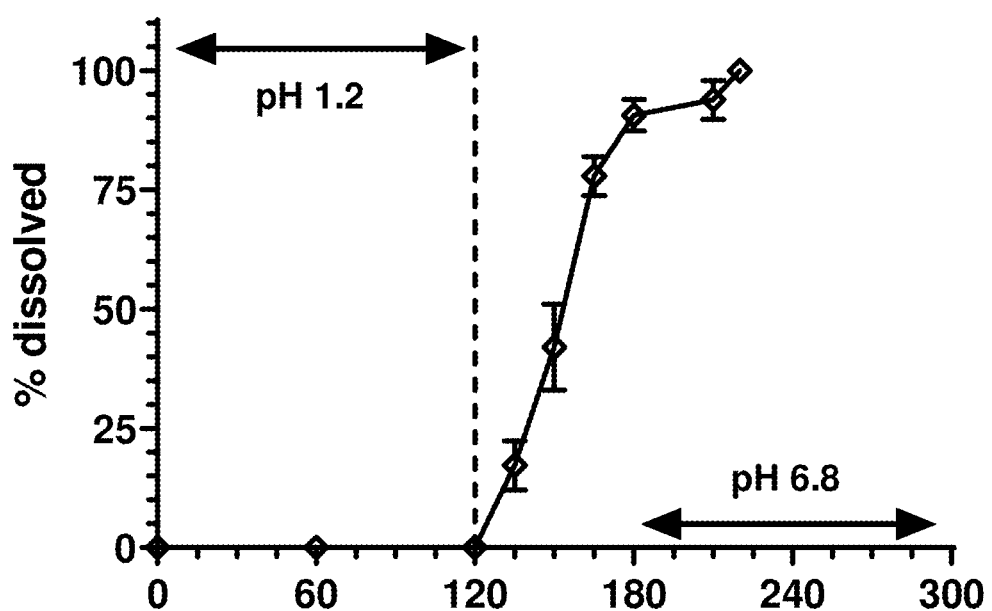
FIG. 3: Dissolution profile of formulation 2 containing 1.6 mg spray dried CR845.HCl in 90% Miglyol® 812, 10% capric acid on a scale of 0-300 mins.
Figure 4:
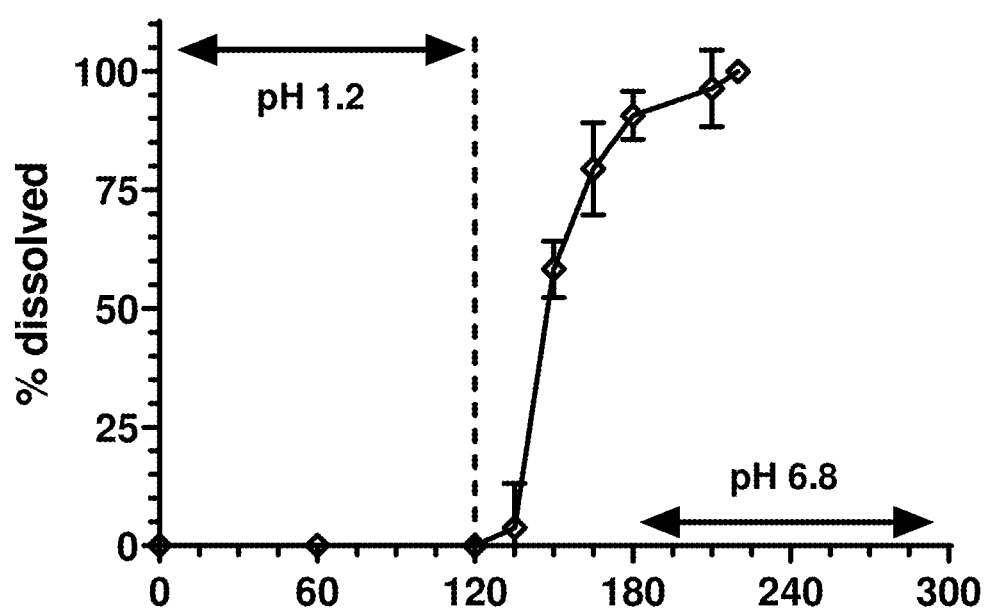
FIG. 4: Dissolution profile of formulation 3 containing 1.6 mg spray dried CR845.HCl in 70% Miglyol® 812, 30% capric acid on a scale of 0-300 mins.
Figure 5:
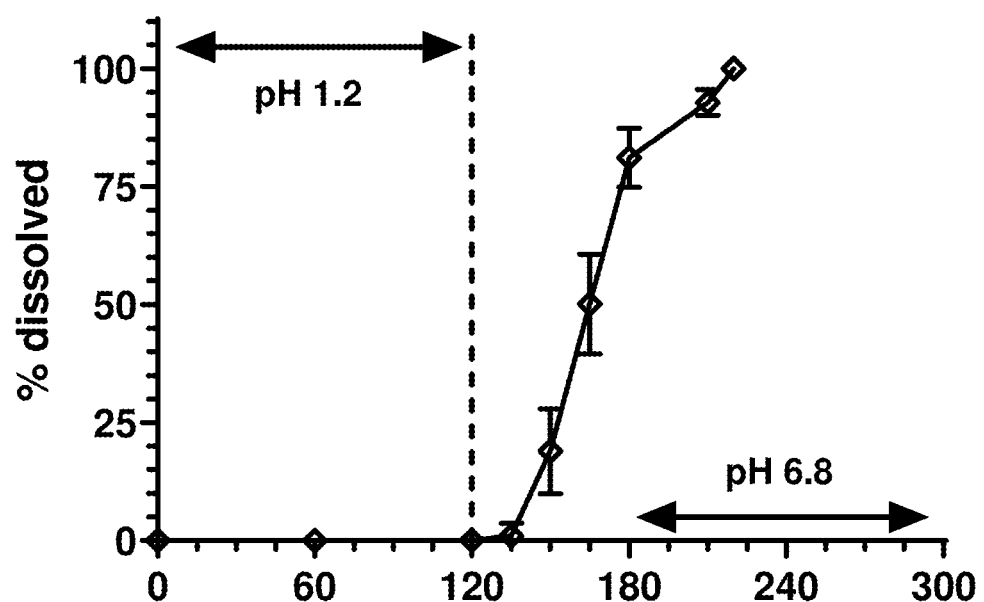
FIG. 5: Dissolution profile of formulation 4 containing 1.6 mg crystallized CR845.HCl in 90% Miglyol® 812, 10% sodium caprate on a scale of 0-300 mins.

In one embodiment, the oral formulation of the invention includes a therapeutic agent comprising a peptide, and at least one absorption enhancer, the absorption enhancer includes a medium chain fatty acid or a salt of a medium chain fatty acid, and a medium chain fatty acid glyceride, wherein the medium chain fatty acid or the salt of the medium chain fatty acid comprises capric acid or a salt of capric acid.

In another embodiment, the oral formulation of the invention includes a kappa opioid receptor agonist peptide, and at least one absorption enhancer, the absorption enhancer includes a medium chain fatty acid or a salt of a medium chain fatty acid, and a medium chain fatty acid glyceride, wherein the medium chain fatty acid or the salt of the medium chain fatty acid comprises capric acid or a salt of capric acid.

In another embodiment, the oral formulation of the invention includes a kappa opioid receptor agonist that includes one or more D-amino acids, and at least one absorption enhancer, the absorption enhancer includes a medium chain fatty acid or a salt of a medium chain fatty acid, and a medium chain fatty acid glyceride, wherein the medium chain fatty acid or the salt of the medium chain fatty acid comprises capric acid or a salt of capric acid. The salt of capric acid can be any suitable salt of capric acid, such as for instance, sodium caprate.

In another embodiment, the oral formulation of the invention includes a kappa opioid receptor agonist that includes one or more D-amino acids, and at least one absorption enhancer, the absorption enhancer includes a medium chain fatty acid or a salt of a medium chain fatty acid, and a medium chain fatty acid glyceride, wherein the medium chain fatty acid glyceride comprises a medium chain fatty acid triglyceride. The medium chain triglyceride can be any suitable medium chain fatty acid triglyceride, such as for instance, and without limitation, one or more of Miglyol® 810 (medium-chain triglycerides of 70% caprylic acid, 30% capric acid), Miglyol® 812 (medium-chain triglycerides of 55% caprylic acid, 45% capric acid), Miglyol® 812N (medium-chain triglyceride of caprylic acid and capric acid, ratio ~60:40% and plant derived glycerol), Capmul® MCM (medium-chain glyceride of 81-87% caprylic acid and 13-19% capric acid), Neobee® 1053 (medium-chain triglyceride of 55% caprylic acid, 44% capric acid), or Neobee® M5 (medium-chain triglyceride of 66% caprylic acid, 32% capric acid).

In one alternative, a suitable additional absorption enhancers can be included, such as lipophilic surfactants, for instance, a propylene glycol mono-di-caprylate/caprate e.g. Capmul® PGMC; a propylene glycol di-caprate such as Captex® 100, or a propylene glycol di-caprylate/caprate such as Captex® 200 to supplement the medium chain fatty acid triglyceride(s) in the kappa opioid receptor agonist formulations of the invention.

In another alternative, the suitable additional absorption enhancers that can be included can a hydrophilic surfactant such as for instance Tween® 80 (Polyoxyethylene 20 sorbitan mono-oleate), Tween® 60 (Polyoxyethylene 20 sorbitan mono-stearate), Lubrasol® ALF (PEG-8-caprylic/capric glycerides), Kolliphor® EL (PEG-35 glyceryl ricinoleate), Kolliphor® HS 15 (PEH-15 hydroxystearate), and Gelucare® 44/14 (Lauroyl PEG-32 mono/di/tri-glycerides) can be added to supplement the medium chain fatty acid triglyceride(s) in the kappa opioid receptor agonist formulations.

In one embodiment, the oral formulation of the invention includes a kappa opioid receptor agonist that includes one or more D-amino acids, and an absorption enhancer, wherein the absorption enhancer includes from about 0.01% to about 5% (w/w) of a kappa opioid receptor agonist such as CR845; from about 25% to about 92% (w/w) Miglyol® 812; and from about 5% to about 50% (w/w) capric acid.

In another embodiment, the oral formulation of the invention includes a kappa opioid receptor agonist that includes one or more D-amino acids, and an absorption enhancer, wherein the absorption enhancer includes from about 0.1% to about 1% (w/w) of a kappa opioid receptor agonist such as CR845; from about 60% to about 90% (w/w) Miglyol® 812; and from about 10% to about 40% (w/w) capric acid.

In another embodiment, the oral formulation of the invention includes a kappa opioid receptor agonist that includes one or more D-amino acids, and an absorption enhancer, wherein the absorption enhancer includes 0.5% (w/w) of a kappa opioid receptor agonist such as CR845; about 70% (w/w) Miglyol® 812; and 30% (w/w) capric acid.

In still another embodiment, the oral formulation of the invention includes a kappa opioid receptor agonist that includes one or more D-amino acids, and an absorption enhancer, wherein the absorption enhancer includes 0.5% (w/w) of a kappa opioid receptor agonist such as CR845; about 90% (w/w) Miglyol® 812; and 10% (w/w) capric acid.

In another embodiment, the oral formulation of the invention includes a kappa opioid receptor agonist that includes one or more D-amino acids, and an absorption enhancer, wherein the absorption enhancer includes from about 0.1% to about 1% (w/w) of a kappa opioid receptor agonist such as CR845; from about 60% to about 95% (w/w) Miglyol® 812; and from about 1% to about 20% (w/w) sodium caprate.

In still another embodiment, the oral formulation of the invention includes a kappa opioid receptor agonist that includes one or more D-amino acids, and an absorption enhancer, wherein the absorption enhancer includes about 0.5% (w/w) of a kappa opioid receptor agonist such as CR845; about 90% (w/w) Miglyol® 812; and about 10% (w/w) sodium caprate.

In one embodiment the kappa opioid receptor agonist can be optionally embedded in a particle matrix of an oligomeric saccharide such as for instance, trehalose.

The formulation of the invention including a kappa opioid receptor agonist that includes one or more D-amino acids, and at least one absorption enhancer, the absorption enhancer including a medium chain fatty acid or a salt of a medium chain fatty acid, and a medium chain fatty acid glyceride can be in the form of a gel or a capsule, wherein the formulation further includes one or one of a pharmaceutically acceptable diluent, an excipient or a carrier. In one embodiment the capsule is an enteric coated capsule or a capsule having intrinsic enteric properties.

In one embodiment, the formulation of the invention includes a kappa opioid receptor agonist such as but not limited to asimadoline (N-[(1S)-2-[(3S)-3-hydroxy-pyrrolidin-1-yl]-1-phenylethyl]-N-methyl-2,2-diphenylacetamide), or nalfurafine ((2E)-N-[(5α,6β)-17-(cyclopropylmethyl)-3,14-dihydroxy-4,5-epoxymorphinan-6-yl]-3-(3-furyl)-N-methylacrylamide), and at least one absorption enhancer, the absorption enhancer including a medium chain fatty acid or a salt of a medium chain fatty acid, and a medium chain fatty acid glyceride.

In another embodiment, the oral formulation of the invention includes a therapeutic agent comprising a peptide, and at least one absorption enhancer, the absorption enhancer includes a medium chain fatty acid or a salt of a medium chain fatty acid, and a medium chain fatty acid glyceride, wherein the medium chain fatty acid or the salt of the medium chain fatty acid comprises capric acid or a salt of capric acid, wherein the formulation does not include a stabilizer, such as polyvinylpyrolidine (PVP). Surprisingly, the formulations of the invention have been found to be effective without the use of PVP or other such stabilizers.

Also provided is a method of treating or preventing a kappa opioid receptor-associated disease or condition in a mammal. The method includes administering to the mammal a composition that includes an effective amount of the above-described formulation of the invention.

The term "medium chain fatty acids" as used in this specification refers to one or more straight chain fatty acids including caproic acid (a $C_6$ fatty acid), caprylic acid (a $C_8$ fatty acid), and capric acid (a $C_{10}$ fatty acid).

The term "medium chain triglyceride" as used herein refers to a glyceride ester of one or more medium chain fatty acids as defined above. The medium chain triglyceride can be any medium chain triglyceride, such as a triglyceride of caproic acid ($C_6$ fatty acid), a triglyceride of caprylic acid ($C_8$ fatty acid), or a triglyceride of capric acid ($C_{10}$ fatty acid). Alternatively, the medium chain triglyceride can be a triglyceride of a mixture of caproic acid and caprylic acid; a mixture of caproic acid and capric acid; or a mixture of caprylic acid and capric acid. In another alternative, the medium chain triglyceride can be a triglyceride of a mixture of all three of the medium chain fatty acids: i.e. caproic acid, caprylic acid and capric acid.

In one embodiment of the invention, the kappa opioid receptor agonist may be suspended in Miglyol® or about 90% Miglyol® and about 10% sodium caprate. Alternatively, the kappa opioid receptor agonist may be suspended in about 95% Miglyol® and about 5% capric acid. Optionally, these formulations may include from about 5 to about 10% EDTA.

The nomenclature used to define the peptides and D-amino acid peptides of the formulations of the invention is specified by Schroder & Lubke, *The Peptides*, Academic Press, 1965, wherein, in accordance with conventional representation, the N-terminus appears to the left and the C-terminus to the right. Where an amino acid residue has isomeric forms, both the L-isomer form and the D-isomer form of the amino acid are intended to be covered unless otherwise indicated. Amino acids are commonly identified herein by the standard three-letter code. The D-isomer of an amino acid is specified by the prefix "D-" as in "D-Phe" which represents D-phenylalanine, the D-isomer of phenylalanine. Similarly, the L-isomer is specified by the prefix "L-" as in "L-Phe." Peptides are represented herein according to the usual convention as amino acid sequences from left to right: N-terminus to C-terminus, unless otherwise specified.

As used herein, D-Arg represents D-arginine, D-Har represents D-homoarginine, which has a side chain one methylene group longer than D-Arg, and D-Nar represents D-norarginine, which has a side chain one methylene group shorter than D-Arg. Similarly, D-Leu means D-leucine, D-Nle means D-norleucine, and D-Hle represents D-homoleucine. D-Ala means D-alanine, D-Tyr means D-tyrosine, D-Trp means D-tryptophan, and D-Tic means D-1,2,3,4-tetrahydroisoquinoline-3carboxylic acid. D-Val means D-valine and D-Met means D-methionine. D-Pro means D-proline, Pro-amide means the D- or L-form of proline amide. D-Pro amide represents D-proline with an amide formed at its carboxy moiety wherein the amide nitrogen may be alkyl substituted, as in —$NR_aR_b$, wherein $R_a$ and $R_b$ are each independently a $C_1$-$C_6$ alkyl group, or one of $R_a$ and $R_b$ is —H. Gly means glycine, D-Ile means D-isoleucine, D-Ser means D-serine, and D-Thr means D-threonine. (E)D-Ala means the D-isomer of alanine which is substituted by the substituent (E) on the β-carbon. Examples of such substituent (E) groups include tert-butyl, cyclopropyl, cyclobutyl, cyclopentyl, cyclohexyl, furyl, pyridyl, thienyl, thiazolyl and benzothienyl. Thus, cyclopentyl-D-Ala means the D-isomer of alanine which is substituted by cyclopentyl on the β-carbon. Similarly, D-Ala(2-thienyl) and (2-thienyl) D-Ala are interchangeable and both mean the D-isomer of alanine substituted at the β-carbon with thienyl that is attached at the 2-ring position.

As used herein, D-Nal means the D-isomer of alanine substituted by naphthyl on the β-carbon. D-2Nal means naphthyl substituted D-alanine wherein the attachment to naphthalene is at the 2-position on the ring structure and D-1Nal means naphthyl-substituted D-alanine wherein the attachment to naphthalene is at the 1-position on the ring structure. By (A)(A')D-Phe is meant D-phenylalanine substituted on the phenyl ring with one or two substituents independently chosen from halo, nitro, methyl, halomethyl (such as, for example, trifluoromethyl), perhalomethyl, cyano and carboxamide. By D-(4-F)Phe is meant D-phenylalanine which is fluoro-substituted in the 4-position of the phenyl ring. By D-(2-F)Phe is meant D-phenylalanine which is fluoro-substituted in the 2-position of the phenyl ring. By D-(4-Cl)Phe is meant D-phenylalanine which is chloro substituted in the 4-phenyl ring position. By (α-Me)D-Phe is meant D-phenylalanine which is methyl substituted at the alpha carbon. By (α-Me)D-Leu is meant D-leucine which is methyl substituted at the alpha carbon.

The designations $(B)_2$D-Arg, $(B)_2$D-Nar, and $(B)_2$D-Har represent D-arginine, D-norarginine and D-homoarginine, respectively, each having two substituent (B) groups on the side chain. D-Lys means D-lysine and D-Hlys means D-homolysine. ζ-(B)D-Hlys, ε-(B)D-Lys, and ε-$(B)_2$-D-Lys represent D-homolysine and D-lysine each having the side chain amino group substituted with one or two substituent (B) groups, as indicated. D-Orn means D-ornithine and δ-(B)α-(B')D-Orn means D-ornithine substituted with (B') at the alpha carbon and substituted with (B) at the side chain δ-amino group.

D-Dap means D-2,3-diaminopropionic acid. D-Dbu represents the D-isomer of alpha, gamma-diamino butyric acid and $(B)_2$D-Dbu represents alpha, gamma-diamino butyric acid which is substituted with two substituent (B) groups at the gamma amino group. Unless otherwise stated, each of the (B) groups of such doubly substituted residues are independently chosen from H— and $C_1$-$C_4$-alkyl. As used herein, D-Amf means D-($NH_2CH_2$-)Phe, i.e., the D-isomer of phenylalanine substituted with aminomethyl on its phenyl ring and D-4Amf represents the particular D-Amf in which the aminomethyl is attached at the 4-position of the ring. D-Gmf means D-Amf(amidino) which represents D-Phe wherein the phenyl ring is substituted with —$CH_2NHC(NH)NH_2$. Amd represents amidino, —$C(NH)NH_2$, and the designations (Amd)D-Amf and D-Amf(Amd) are also interchangeably used for D-Gmf. The designations Ily and Ior are respectively used to mean isopropyl Lys and isopropyl Orn, wherein the side chain amino group is alkylated with an isopropyl group.

Alkyl means an alkane radical which can be a straight, branched, and cyclic alkyl group such as, but not limited to, methyl, ethyl, propyl, isopropyl, cyclopropyl, butyl, t-butyl, sec-butyl, pentyl, cyclopentyl, hexyl, cyclohexyl, cyclohexylethyl. $C_1$ to $C_8$ alkyl refers to alkyl groups having between one and eight carbon atoms. Similarly, $C_1$-$C_6$ alkyl refers to alkyl groups having between one and six carbon atoms. Likewise, $C_1$-$C_4$ alkyl refers to alkyl groups having between one and four carbon atoms. By lower alkyl is meant $C_1$-$C_6$ alkyl. Me, Et, Pr, Ipr, Bu, and Pn are interchangeably used to represent the common alkyl groups: methyl, ethyl, propyl, isopropyl, butyl, and pentyl, respectively. Although the linkage for an alkyl group is typically at one end of an alkyl chain, the linkage may be elsewhere in the chain, e.g. 3-pentyl which may also be referred to as ethylpropyl, or 1-ethylprop-1-yl. Alkyl-substituted, such as $C_1$ to $C_6$ alkyl-substituted amidino, indicates that the relevant moiety is substituted with one or more alkyl groups.

Where a specified moiety is null, the moiety is absent and if such moiety is indicated to be attached to two other moieties, such two other moieties are connected by one covalent bond. Where a connecting moiety is shown herein as attached to a ring at any position on the ring, and attached to two other moieties, such as $R_1$ and $R_2$, in the case where the connecting moiety is specified to be null, then the $R_1$ and $R_2$ moieties can each be independently attached to any position on the ring.

The terms "heterocycle", "heterocyclic ring" and "heterocyclyl" are used interchangeably herein and refer to a ring or ring moiety having at least one non-carbon ring atom, also called a heteroatom, which can be a nitrogen atom, a sulfur atom, or an oxygen atom. Where a ring is specified as having a certain number of members, the number defines the number of ring atoms without reference to any substituents or hydrogen atoms bonded to the ring atoms. Heterocycles, heterocyclic rings and heterocyclyl moieties can include multiple heteroatoms independently selected from nitrogen, sulfur, or oxygen atom in the ring. Rings can be substituted at any available position. For example, but without limitation, 6- and 7-membered rings are often substituted in the 4-ring position and 5-membered rings are commonly substituted in the 3-position, wherein the ring is attached to the peptide amide chain at the 1-ring position.

The term "saturated" means an absence of double or triple bonds and the use of the term in connection with rings describes rings having no double or triple bonds within the ring, but does not preclude double or triple bonds from being present in substituents attached to the ring. The term "non-aromatic" in the context of a particular ring refers to an absence of aromaticity in that ring, but does not preclude the presence of double bonds within the ring, including double bonds which are part of an aromatic ring fused to the ring in question. Nor is a ring atom of a saturated heterocyclic ring moiety precluded from being double-bonded to a non-ring atom, such as for instance a ring sulfur atom being double-bonded to an oxygen atom substituent. As used herein, heterocycles, heterocyclic rings and heterocyclyl moieties also include saturated, partially unsaturated and heteroaromatic rings and fused bicyclic ring structures unless otherwise specified. A heterocycle, heterocyclic ring or heterocyclyl moiety can be fused to a second ring, which can be a saturated, partially unsaturated, or aromatic ring, which ring can be a heterocycle or a carbocycle. Where indicated, two substituents can be optionally taken together to form an additional ring. Rings may be substituted at any available position. A heterocycle, heterocyclic ring and heterocyclyl moiety can, where indicted, be optionally substituted at one or more ring positions with one or more independently selected substituents, such as for instance, $C_1$-$C_6$ alkyl, $C_3$-$C_8$ cycloalkyl, $C_1$-$C_6$ alkoxy, halo $C_1$-$C_6$ alkyl, optionally substituted phenyl, aryl, heterocyclyl, oxo, —OH, —Cl, —F, —$NH_2$, —$NO_2$, —CN, —COOH and amidino. Suitable optional substituents of the phenyl substituent include for instance, but without limitation, one or more groups selected from $C_1$-$C_3$ alkyl, $C_1$-$C_3$ alkoxy, halo $C_1$-$C_3$ alkyl, oxo, —OH, —Cl, —F, —$NH_2$, —$NO_2$, —CN, —COOH and amidino.

D-Phe and substituted D-Phe are examples of a suitable amino acid for residue $Xaa_1$ in Formula I. The phenyl ring can be substituted at any of the 2-, 3- and/or 4-positions. Particular examples of permitted substitutions include, for instance, chlorine or fluorine at the 2- or 4-positions. Also the alpha-carbon atom may be methylated. Other equivalent residues which represent conservative changes to D-Phe can also be used. These include D-Ala(cyclopentyl), D-Ala(thienyl), D-Tyr and D-Tic. The residue at the second position, $Xaa_2$ can also be D-Phe or substituted D-Phe with such substitutions including a substituent on the 4-position carbon of the phenyl ring, or on both the 3- and 4-positions. Alternatively, $Xaa_2$ can be D-Trp, D-Tyr or D-alanine substituted by naphthyl. The third position residue, $Xaa_3$ can be any non-polar amino acid residue, such as for instance, D-Nle, D-Leu, (t-Me)D-Leu, D-Hle, D-Met or D-Val. However, D-Ala(cyclopropyl, cyclobutyl, cyclopentyl or cyclohexyl) or D-Phe can also be used as $Xaa_3$. The fourth position residue $Xaa_4$ can be any positively charged amino acid residue, such as for instance, D-Arg and D-Har, which can be optionally substituted with lower alkyl groups, such as one or two ethyl groups. Alternatively, D-Nar and any other equivalent residues can be used, such as, for instance, D-Lys or D-Orn (either of which can be ω-amino group alkylated, for example by methyl or isopropyl groups, or methylated at the α-carbon group). Moreover, D-Dbu, D-4-Amf (which can be optionally substituted with amidino), and D-Hlys are also suitable amino acids at this position.

D-amino acid peptides of the invention contain one or more chiral centers, each of which has two possible three-dimensional spatial arrangements (configurations) of the four substituents around the central carbon atom. These are known as "stereoisomers", and more specifically as "enantiomers" (all chiral centers inverted) or "diastereoisomers" (two or more chiral centers, at least one chiral center remaining the same). In a specific embodiment of the invention, the amino acids which make up the tetrapeptide backbone, $Xaa_1Xaa_2Xaa_3Xaa_4$ of the kappa opioid receptor agonist peptide amides are specified to be D-amino acids i.e., the opposite configuration to those generally found in mammals. Reference to stereoisomers of the synthetic peptide amides of the invention concerns chiral centers other than the alpha carbons of the D-amino acids which make up $Xaa_1$-$Xaa_4$. Thus, stereoisomers of synthetic peptide amides that are embodiments of the invention wherein each of $Xaa_1$-$Xaa_4$ are specified to be D-amino acids, do not include L-amino acids or racemic mixtures of the amino acids at these positions. Similarly, reference to racemates herein concerns a center other than the alpha carbons of the D-amino acids which make up $Xaa_1$-$Xaa_4$. Chiral centers in the synthetic peptide amides of the invention for which a stereoisomer may take either the R or S configuration include chiral centers in the moiety attached to the carboxy-terminus of $Xaa_4$, and also chiral centers in any amino acid side chain substituents of $Xaa_1$-$Xaa_4$.

The kappa opioid receptor agonist peptide amides useful in the practice of the invention described herein can be used or prepared in alternate forms. For example, many amino-containing compounds can be used or prepared as an acid salt. Often such salts improve isolation and handling properties. For example, depending on the reagents, reaction conditions and the like, compounds such as the kappa opioid receptor agonist peptide amides described herein can be used or prepared, for example, as the hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic kappa opioid receptor agonist peptide amides useful in the practice of the present invention may exist as zwitterions. All forms of these kappa opioid receptor agonist peptide amides, including free acid, free base and zwitterions, are contemplated to be within the scope of the present invention. It is well known in the art that compounds containing both amino and carboxyl groups often exist in equilibrium with their zwitterionic forms. Thus, for any compound described herein that contains, for example, both amino and carboxyl groups, it will also be understood to include the corresponding zwitterion.

As used herein, the chemical designation "tetrapeptide-[ω(4-amino-piperidine-4-carboxylic acid)]" is used to indicate the aminoacyl moiety of the kappa opioid receptor agonist peptide amides of the invention derived from 4-aminopiperidine-4-carboxylic acid, wherein the nitrogen atom of the piperidine ring is bound to the C-terminal carbonyl-carbon of the tetrapeptide fragment, unless otherwise indicated.

In another embodiment, the amide moiety of the D-amino acid amide (designated as "G" in structural formula I and formula III, below) is chosen from the following groups:

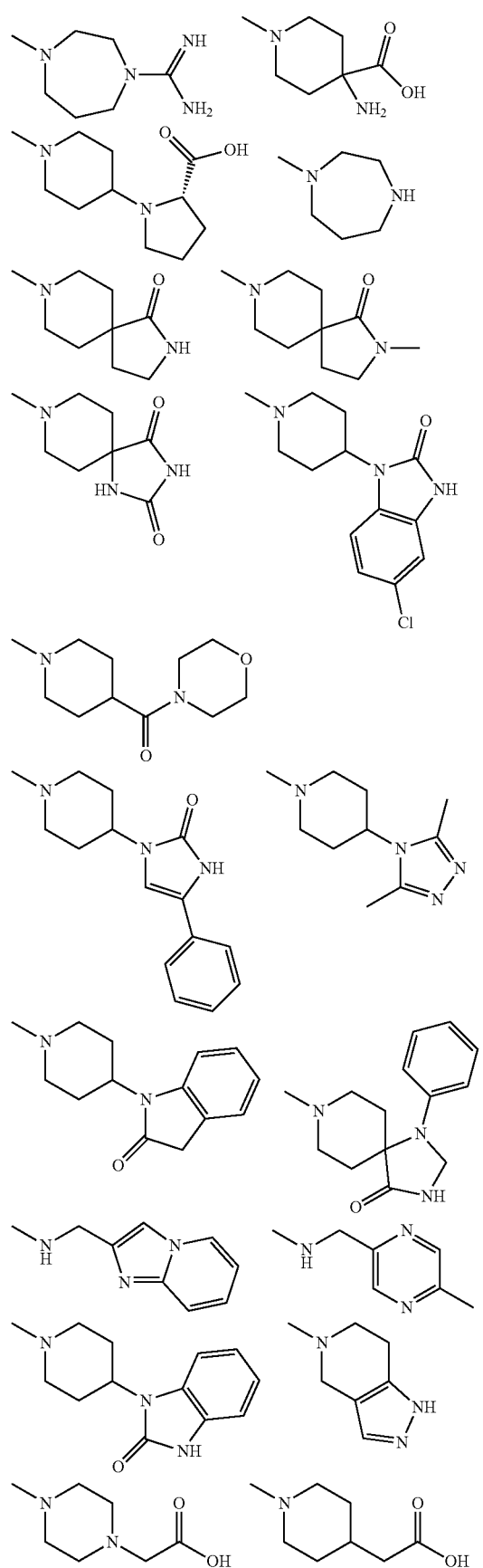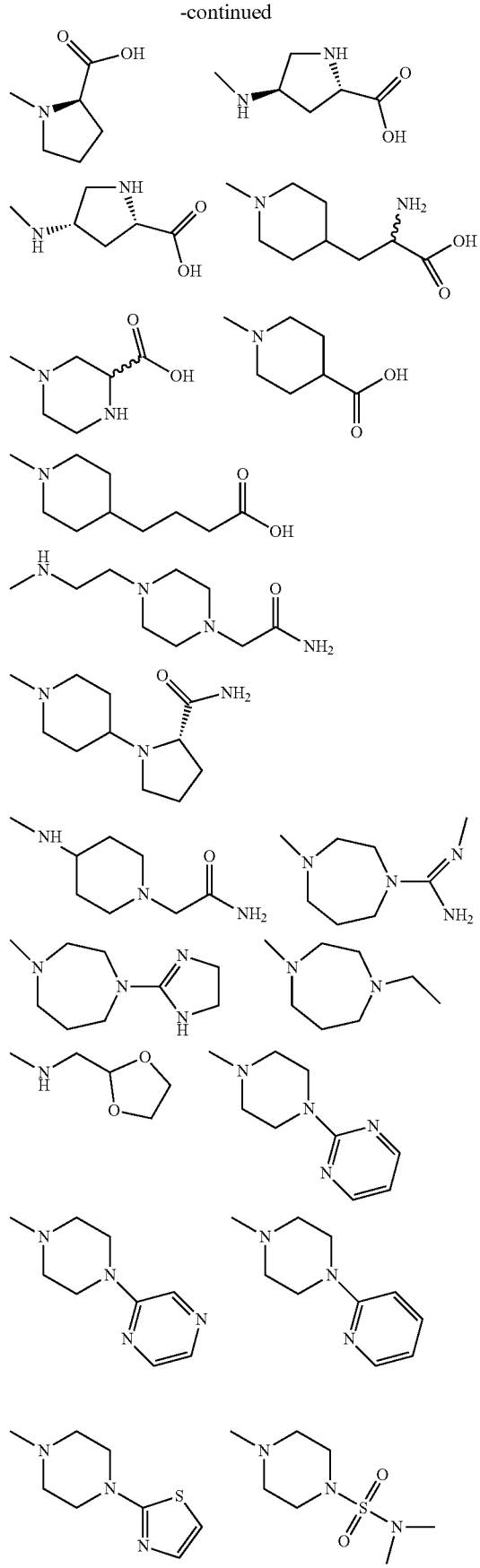

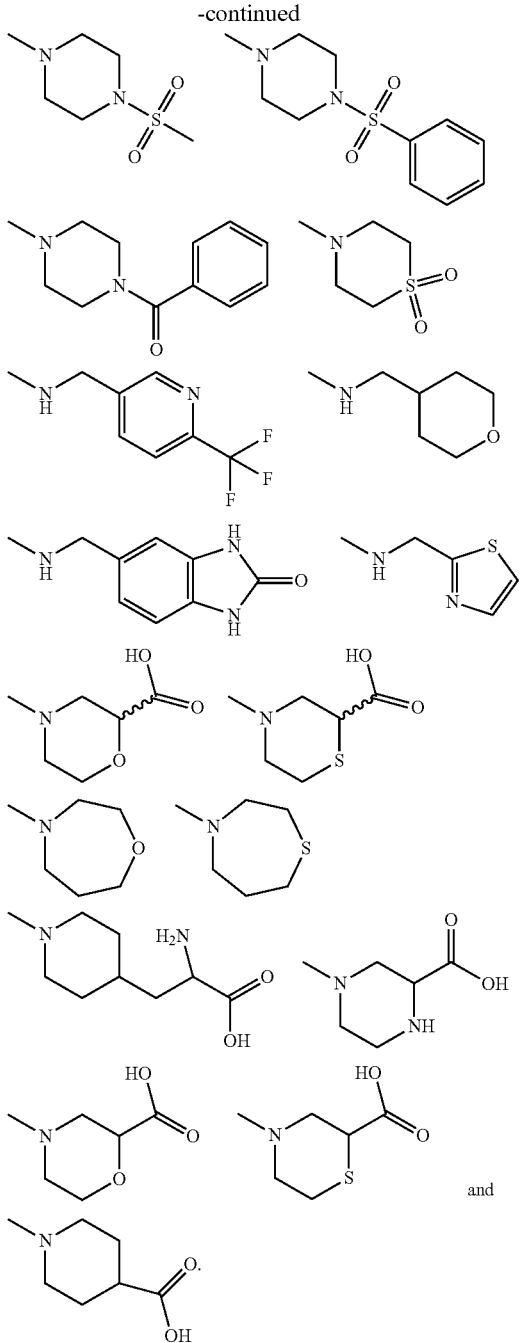

In another embodiment W is null and G is

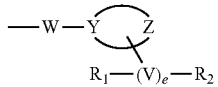

In another embodiment W is —N—$(CH_2)_b$ with b equal to 0, 1, 2, 3, or 4. In one aspect b is zero and Y is a carbon atom. In another aspect b is 1 or 2 and Y is a nitrogen atom. In another embodiment W is —N—$(CH_2)_c$—O—. In one particular aspect c is 1 or 2. In another aspect the Y and Z-containing ring moiety is a four or five membered ring and Y is a nitrogen atom. In another embodiment the Y and Z-containing ring moiety is a four or five membered ring and Y is a carbon atom.

In another embodiment the Y and Z-containing ring moiety is a six or seven membered ring, Y is nitrogen and Z is a carbon atom. In another alternative, the Y and Z-containing ring moiety is a six membered ring. In one aspect the Y and Z-containing ring moiety is a seven membered ring. In still another aspect the Y and Z-containing ring moiety is a six or seven membered ring and both Y and Z are nitrogen atoms.

In another embodiment e is zero and $R_1$ and $R_2$ are bonded directly to the same ring atom. In one aspect e is zero, $R_2$ is —H and $R_1$ is bonded directly to a carbon ring atom adjacent to Z. In another aspect $R_1$ is H, amidino, $C_1$-$C_3$ alkyl substituted amidino, $C_1$-$C_3$ alkyl, dihydroimidazole, D-Pro, D-Pro amide, or —$CONH_2$ and wherein e is zero and $R_2$ is —H. In another aspect $R_1$ is —H, amidino, or methyl amidino. In one aspect the Y and Z-containing ring moiety is a five membered ring, e is zero and $R_1$ is —COOH.

In another embodiment G is

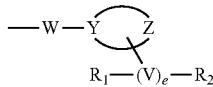

and $Xaa_1$ is D-Phe, $Xaa_2$ is D-Phe, $Xaa_3$ is D-Leu, $Xaa_4$ is $\epsilon(B)_2$D-Lys, or $\delta$-$(B)_2$D-Orn, wherein (B) is —H, methyl, or isopropyl; further wherein W is null, the Y and Z-containing ring moiety is a six or seven membered ring, Y is a nitrogen atom, e is zero, $R_1$ is —$NH_2$, amidino, $C_1$-$C_3$ alkyl, $C_1$-$C_3$ alkyl-substituted amidino, dihydroimidazole, D-Pro, or D-Pro amide, and $R_2$ is H or —COOH.

In one particular embodiment the kappa opioid receptor agonist peptide amide useful in the formulations of the invention has the formula:

(Formula III)

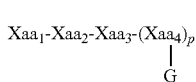

wherein G is:

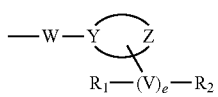

and b is zero and Y is a carbon atom. In another embodiment, b is 1 or 2 and Y is a nitrogen atom. In a particular aspect of the invention, b is 2.

In one embodiment, the invention provides a kappa opioid receptor agonist peptide amide wherein each $Xaa_1$ is D-Phe, each $Xaa_2$ is D-Phe, each $Xaa_3$ is D-Leu and each $Xaa_4$ is D-Lys. In another embodiment, each $Xaa_1$ is D-Ala(2-thienyl), each $Xaa_2$ is D-Phe, each $Xaa_3$ is D-Nle, and each $Xaa_4$ is D-Arg.

In another embodiment each $Xaa_4$ is chosen from $\epsilon(B)_2$D-Lys, $(B)_2$D-Arg, and $\delta$-$(B)_2$D-Orn. In another particular aspect each $Xaa_4$ is chosen from D-Arg, $(Et)_2$D-Arg, and $\delta$-(B)D-Orn, and (B) is H, Me, iPr, or Bu.

In another embodiment G is

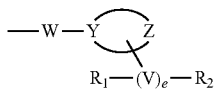

and the Y- and Z-containing moiety is [ω(4-aminopiperidine-4-carboxylic acid)]-OH.

In one particular embodiment $Xaa_1$ is chosen from D-Phe, D-(4-F)Phe, D-(2-F)Phe, cyclopentyl D-Ala, 2-thienyl D-Ala, $Xaa_2$ is chosen from D-(4-F)Phe, D-(4-Cl)Phe, D-1Nal, D-2Nal, and D-Trp, and $Xaa_3$-$Xaa_4$ is chosen from D-Nle-D-Arg and D-Leu-D-Orn.

In another embodiment W is an N-alkoxyl linker of the formula: —N—$(CH_2)_2$—O—. In an alternative embodiment W is null and $Xaa_1Xaa_2Xaa_3Xaa_4$ is directly bonded to Y. In a second alternative embodiment, W is —NH—$(CH_2)_2$—.

Alternatively, and in other embodiments, each instance of one or more of the pairs of residues $Xaa_1$, $Xaa_2$, $Xaa_3$ or $Xaa_4$ can be different. For example, one instance of $Xaa_1$ can be D-phenylalanine, while the second instance of $Xaa_1$ in the same molecule can be a different $Xaa_1$ residue, such as D-(4-F)phenylalanine. Similarly, one instance of $Xaa_2$ can be D-phenylalanine, while the second instance of $Xaa_2$ in the same molecule can be D-Ala(2-thienyl). Likewise, one instance of $Xaa_3$ can be D-norleucine, while the second instance of $Xaa_3$ in the same molecule can be D-leucine. In the same manner, one instance of $Xaa_4$ can be D-ornithine, while the second instance of $Xaa_4$ in the same molecule can be D-arginine, and so on.

In one embodiment, the invention provides a kappa opioid receptor agonist peptide amide wherein $Xaa_1$ is D-Ala(2-thienyl). In another embodiment $Xaa_1$ is D-(4-F) phenylalanine and $Xaa_2$ is D-(4-Cl)phenylalanine. In another embodiment each $Xaa_1$ is D-phenylalanine or D-Ala(2-thienyl) and each $Xaa_2$ is D-(4-Cl)phenylalanine. In another embodiment $Xaa_1$-$Xaa_2$ is D-phenylalanine-D-phenylalanine.

In one embodiment each $Xaa_3$ is chosen from D-norleucine and D-leucine. In another embodiment each $Xaa_2$ is D-phenylalanine, each $Xaa_3$ is D-norleucine, and each $Xaa_4$ is D-arginine. In another embodiment each $Xaa_3$ can be D-leucine or D-norleucine.

In another embodiment $Xaa_4$ is chosen from δ$(B)_2$D-ornithine and D-arginine. Alternatively, each $Xaa_4$ is δ$(B)_2$D-ornithine and each (B) is chosen from —H, methyl and isopropyl. In still another embodiment, each $Xaa_4$ is $(B)_2$D-ornithine, wherein one (B) is —H, and the other (B) chosen from methyl and isopropyl. In one aspect, each $Xaa_4$ is $(B)_2$D-arginine, or δ-$(B)_2$D-ornithine. In another embodiment each $Xaa_4$ can be a residue chosen from D-arginine, $(Et)_2$D-arginine, and δ-(B)D-ornithine, and wherein (B) is —H, methyl, isopropyl, or butyl. In one embodiment the dipeptide $Xaa_3$-$Xaa_4$ is chosen from D-leucine-D-ornithine and D-norleucine-D-arginine.

In another particular embodiment, the Y and Z-containing ring moiety is a four or five membered ring and Y is a nitrogen atom. Alternatively, the Y- and Z-containing ring moiety can be a four or five membered ring wherein Y is a carbon atom. In a different embodiment, the Y and Z-containing ring moiety is a 6- or 7-membered ring, Y is a nitrogen atom and Z is a carbon atom. In one aspect of this embodiment, the Y and Z-containing ring moiety is a 6-membered ring. Alternatively, the Y and Z-containing ring moiety can be a seven membered ring. In one aspect of this embodiment, the Y and Z-containing ring moiety is a 6- or 7-membered ring and both Y and Z are nitrogen atoms.

In another particular embodiment the Y- and Z-containing ring moiety is a six or seven membered ring, or an eight-membered ring, Y is a carbon atom, and Z is a nitrogen atom. In one aspect, Y is a nitrogen atom and Z is a carbon atom. In an alternative embodiment Y and Z are each nitrogen atoms.

In another particular embodiment the Y- and Z-containing ring moiety is an optionally substituted 4-, 5-, 6-, 7-, or 8-membered heterocyclic ring moiety wherein Y is a carbon or a nitrogen atom and Z is carbon, nitrogen, oxygen, sulfur, sulfoxide, or sulfonyl; and the 4-, 5-, 6-, 7-, or 8-membered heterocyclic ring moiety is optionally singly or doubly substituted with substituents independently chosen from $C_1$-$C_6$ alkyl, —$C_1$-$C_6$ alkoxy, oxo, —OH, —Cl, —F, —$NH_2$, —$NO_2$, —CN, —COOH, and amidino. In one aspect when the Y- and Z-containing ring moiety is a six, seven or eight-membered ring, then Y and Z are separated by at least two ring atoms. In another aspect, when the Y- and Z-containing ring moiety is non-aromatic and Z is a carbon or a nitrogen atom, then such ring moiety includes at least one sulfur or oxygen ring heteroatom. In a particular aspect, when the Y- and Z-containing ring moiety is aromatic, then Y is a carbon atom.

In one embodiment of the kappa opioid receptor agonist peptide amide of the invention, $R_1$ is —H, —OH, —$NH_2$, —COOH, $C_1$-$C_3$ alkyl, amidino, $C_1$-$C_3$ alkyl-substituted amidino, dihydroimidazole, D-Pro, D-Pro amide, or —$CONH_2$. In another particular embodiment $R_2$ is —H, —COOH, or $C_1$-$C_3$ alkyl. In one aspect, only one of $R_1$ and $R_2$ is a hydrogen atom. In a particular embodiment $R_1$ is —H, D-Pro, D-Pro amide, or —$NH_2$ and $R_2$ is H or —COOH. In one aspect of this embodiment, $R_1$ is —$NH_2$ and $R_2$ is —COOH.

In one embodiment, the operator, e is zero and $R_1$ and $R_2$ are bonded directly to the same ring atom. In a particular embodiment, e is zero, $R_2$ is —H and $R_1$ is bonded directly to a carbon ring atom adjacent to Z. In another particular embodiment, $R_1$ is —H, amidino, $C_1$-$C_3$ alkyl substituted amidino, $C_1$-$C_3$ alkyl, dihydroimidazole, D-Pro, D-Pro amide, or —$CONH_2$ and e is zero and $R_2$ is —H.

In one embodiment of the kappa opioid receptor agonist peptide amide of the invention, $Xaa_1$ is D-Phe, $Xaa_2$ is D-Phe, $Xaa_3$ is D-Leu, $Xaa_4$ is δ-$(B)_2$D-Orn, wherein (B) is —H, methyl, or isopropyl; such that wherein W is null, the Y and Z-containing ring moiety is a six or seven membered ring, Y is a nitrogen atom, e is zero, $R_1$ is —$NH_2$, amidino, $C_1$-$C_3$ alkyl, $C_1$-$C_3$ alkyl-substituted amidino, dihydroimidazole, D-Pro, or D-Pro amide, and $R_2$ is H or —COOH.

In one embodiment of the kappa opioid receptor agonist peptide amide of the invention: $Xaa_1$ is chosen from (A) D-Phe, (t-Me)D-Phe, D-Tyr, D-Tic, (tert-butyl)D-Gly, and β-(E)D-Ala, wherein (A) is chosen from —H, —F, —Cl, —$NO_2$, and —$CH_3$, and (E) is chosen from tert-butyl, cyclopentyl and thienyl; $Xaa_2$ is chosen from (A)(A')D-Phe, D-1Nal, D-2Nal, D-Tyr, and D-Trp, wherein (A') is H or Cl; $Xaa_3$ is chosen from D-Nle, D-Phe, (cyclopentyl) D-Ala, D-Leu, (α-Me)D-Leu, D-Hle, D-Val, and D-Met; and $Xaa_4$ is chosen from D-Arg, (ethyl)$_2$D-Arg, D-Nar, D-Har, (ethyl)$_2$D-Har, ε-(isopropyl)D-Lys, D-Lys, D-Amf, amidino-D-Amf, β-amidino-D-Dap, D-Dbu, D-Orn, α-(methyl) D-Orn and δ-(isopropyl)D-Orn.

In another embodiment of the kappa opioid receptor agonist peptide amide of the invention: $Xaa_1Xaa_2$ is D-Phe-D-Phe, $Xaa_3$ is D-Leu or D-Nle and $Xaa_4$ is chosen from $(B)_2$D-Arg, D-Lys, $(B)_2$D-Nar, $(B)_2$D-Har, ζ-(B)D-Hlys, D-Dap, amidino-D-Dap, ε-(B)D-Lys, ε-(B)$_2$-D-Lys, D-Amf, amidino-D-Amf, γ-(B)$_2$D-Dbu and δ-(B)$_2$α-(B')D-Orn.

In another embodiment of the kappa opioid receptor agonist peptide amide of the invention: Xaa$_4$ is chosen from D-Lys, (B)$_2$D-Har, c(B)-D-Lys, δ(B)$_2$-α(B')D-Orn and ε(B)$_2$-D-Lys.

In another embodiment of the kappa opioid receptor agonist peptide amide of the invention: Xaa$_1$ is chosen from (A) D-Phe, (α-Me)D-Phe, D-Tyr, D-Tic, (tert-butyl)D-Gly, and β-(E)D-Ala, wherein A is selected from the group consisting of —H, —F, —Cl, —NO$_2$, and —CH$_3$, and (E) is selected from the group consisting of tert-butyl, cyclopentyl and thienyl; Xaa$_2$ is selected from the group consisting of (A)(A')D-Phe, D-1Nal, D-2Nal, D-Tyr, and D-Trp, wherein (A') is H or Cl; Xaa$_3$ is selected from the group consisting of D-Nle, D-Phe, (cyclopentyl)D-Ala, D-Leu, (α-Me)D-Leu, D-Hle, D-Val, and D-Met; and Xaa$_4$ is selected from the group consisting of D-Arg, (ethyl)$_2$D-Arg, D-Nar, D-Har, (ethyl)$_2$D-Har, ε-(isopropyl)D-Lys, D-Lys, D-Amf, amidino-D-Amf, β-amidino-D-Dap, D-Dbu, D-Orn, α-(methyl)D-Orn and δ-(isopropyl)D-Orn.

In another embodiment of the kappa opioid receptor agonist peptide amide of the invention: Xaa$_1$ is D-Phe; Xaa$_2$ is D-Phe; Xaa$_3$ is D-Leu and Xaa$_4$ is chosen from D-Nar, D-Orn, and (isopropyl)D-Orn.

In another embodiment of the kappa opioid receptor agonist peptide amide of the invention: L is a linker chosen from ε-D-Lys, ε-Lys, δ-D-Orn, δ-Orn, 4-amino-4-carboxylic piperidine and bis(D-Lys-Gly)Lactam.

In another embodiment of the kappa opioid receptor agonist peptide amide, the Y and Z-containing ring moiety is a six-membered saturated ring. In a particular aspect of this embodiment, the Y and Z-containing ring moiety comprises a single heteroatom and e is zero, and R$_1$ and R$_2$ taken together or with one or two ring atoms of the Y and Z-containing ring moiety comprise an optionally substituted monocyclic or bicyclic 4-, 5, 6-, 7, 8- or 9-membered heterocyclic ring moiety. In a particular aspect of this embodiment, R$_1$ and R$_2$ taken together with one ring atom of the Y and Z-containing ring moiety comprises a five-membered heterocyclic ring moiety having only heteroatoms chosen from N and O, which heterocyclic ring moiety with the Y and Z-containing ring moiety forms a spiro structure.

In another embodiment of the kappa opioid receptor agonist peptide amide, the Y and Z-containing ring moiety includes two heteroatoms. In a particular aspect of this embodiment, the two heteroatoms of the Y and Z-containing ring moiety are both nitrogen. In another particular aspect of this embodiment, the integer e is zero, R$_2$ is hydrogen and the Y- and Z-containing ring moiety is 3-substituted with R$_1$. In still another particular aspect of this embodiment, the two heteroatoms of the Y- and Z-containing ring moiety are nitrogen and oxygen. In one particular aspect the Y- and Z-containing ring moiety is 3-substituted with R$_1$, the integer e is zero and R$_2$ is hydrogen. In another particular aspect the two heteroatoms of the Y- and Z-containing ring moiety are nitrogen and sulfur. In still another particular aspect the Y- and Z-containing ring moiety is 3-substituted with R$_1$, e is zero and R$_2$ is H.

As used herein, a kappa opioid receptor-associated disease, condition or disorder is any disease, condition or disorder that is preventable or treatable by activation of a kappa opioid receptor. In some embodiments, a particular oral dose of the formulation of the invention that includes the kappa opioid receptor agonist peptide amide can be chosen by a clinician to completely prevent or cure the disease, condition or disorder. In other embodiments a particular oral dose of the formulation of the invention that includes the kappa opioid receptor agonist peptide amide chosen by the clinician ameliorates or reduces one or more symptoms of the disease, condition or disorder.

As used herein, "effective amount" or "sufficient amount" of the of the formulation of the invention that includes the kappa opioid receptor agonist peptide amide included in the formulation of the invention refers to an amount of the formulation as described herein that may be therapeutically effective to inhibit, prevent, or treat a symptom of a particular disease, disorder, condition, or side effect.

As used herein, "pharmaceutically acceptable" refers to compounds, materials, compositions, and/or dosage forms which are, within the scope of sound medical judgment, suitable for contact with the tissues of human beings and animals without severe toxicity, irritation, allergic response, or other complications, commensurate with a benefit-to-risk ratio that is reasonable for the medical condition being treated.

As used herein, "dosage unit" refers to a physically discrete unit suited as unitary dosages for a particular individual or condition to be treated. Each unit may contain a predetermined quantity of the formulation of the invention comprising the active kappa opioid receptor agonist peptide amide calculated to produce the desired therapeutic effect(s), optionally in association with a pharmaceutical carrier. The specification for the dosage unit forms may be dictated by (a) the unique characteristics of the active kappa opioid receptor agonist peptide amide, and the particular therapeutic effect to be achieved, and (b) the limitations inherent in the art of compounding such active kappa opioid receptor agonist peptide amide. The dosage unit is often expressed as weight of compound per unit body weight, for instance, in milligrams of compound per kilogram of body weight of the subject or patient (mg/kg). Alternatively, the dosage can be expressed as the amount of the compound per unit body weight per unit time, (mg/kg/day) in a particular dosage regimen. In a further alternative, the dosage can be expressed as the amount of compound per unit body surface area (mg/m$^2$) or per unit body surface area per unit time (mg/m$^2$/day).

As used herein, a "pharmaceutically acceptable salt" refers to a derivative of a compound wherein the parent compound is modified by making an acid or a base salt thereof. Examples of pharmaceutically acceptable salts include, but are not limited to, mineral or organic acid salts of basic residues such as amines; alkali or organic salts of acidic residues such as carboxylic acids and the like. The pharmaceutically acceptable salts include the conventional non-toxic salts or the quaternary ammonium salts of the parent compound formed, for example, from non-toxic inorganic or organic acids. For instance, such conventional non-toxic salts include those derived from inorganic acids such as hydrochloric, hydrobromic, sulfuric, sulfamic, phosphoric, nitric acids and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic acids, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine. Thus, a pharmaceutically acceptable salt of a synthetic peptide amide can be formed from any such peptide amide having either acidic, basic or both functional groups. For example, a peptide amide having a carboxylic acid group, may in the presence of a pharmaceutically suitable base, form a carboxylate anion paired with a cation such as a sodium or potassium cation. Similarly, a peptide amide having an amine functional group may, in the presence of a pharmaceutically suitable acid such as HCl, form a salt.

An example of a pharmaceutically acceptable solvate of a kappa opioid receptor agonist peptide amide is a combination of a peptide amide with solvent molecules which yields a complex of such solvent molecules in association with the peptide amide. Combinations of a drug and propylene glycol (1,2-propanediol) have been used to form pharmaceutical drug solvates. See for example U.S. Pat. No. 3,970,651. Other suitable solvates are hydrates of drug compounds. Such hydrates include hydrates which either have comparable activity or hydrates which are converted back to the active compound following administration. A pharmaceutically acceptable N-oxide of a synthetic peptide amide is such a compound that contains an amine group wherein the nitrogen of the amine is bonded to an oxygen atom.

A pharmaceutically acceptable crystalline, isomorphic crystalline or amorphous form of a kappa opioid receptor agonist peptide amide useful in the formulations of the invention can be any crystalline or non-crystalline form of a pharmaceutically acceptable acidic, basic, zwitterionic, salt, hydrate or any other suitably stable, physiologically compatible form of the kappa opioid receptor agonist peptide amide according to the invention.

The kappa opioid receptor agonist peptide amide in the formulations of the invention can be incorporated into pharmaceutical compositions. The compositions can include an effective amount of the kappa opioid receptor agonist peptide amide in a pharmaceutically acceptable diluent, excipient or carrier. Conventional excipients, carriers and/or diluents for use in pharmaceutical compositions are generally inert and make up the bulk of the preparation. The pharmaceutical excipient or carrier can be any compatible, non-toxic substance suitable as a vehicle for delivery the synthetic peptide amide of the invention. Suitable excipients or carriers include, but are not limited to, sterile water (preferably pyrogen-free), saline, phosphate-buffered saline (PBS), water/ethanol, water/glycerol, water/sorbitol, water/polyethylene glycol, propylene glycol, cetylstearyl alcohol, carboxymethylcellulose, corn starch, lactose, glucose, microcrystalline cellulose, magnesium stearate, polyvinylpyrrolidone (PVP), citric acid, tartaric acid, oils, fatty substances, waxes or suitable mixtures of any of the foregoing.

The pharmaceutical composition according to the invention can be formulated as a liquid, semisolid or solid dosage form. For example the pharmaceutical preparation can be in the form of a solution, drops, syrup, spray, suspension, gel, emulsion or in a particulate form, such as pellets or granules, optionally pressed into tablets or lozenges, packaged in capsules or suspended in a liquid. The tablets can contain binders, lubricants, diluents, coloring agents, flavoring agents, wetting agents and may be enteric-coated to survive the acid environment of the stomach and dissolve in the more alkaline conditions of the intestinal lumen. Alternatively, the tablets can be sugar-coated or film coated with a water-soluble film. Pharmaceutically acceptable adjuvants, buffering agents, dispersing agents, and the like, may also be incorporated into the pharmaceutical compositions.

Binders include for instance, starch, mucilage, gelatin and sucrose. Lubricants include talc, lycopodium, magnesium and calcium stearate/stearic acid. Diluents include lactose, sucrose, mannitol, salt, starch and kaolin. Wetting agents include propylene glycol and sorbitan monostearate.

For oral administration, an active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. To facilitate drug stability and absorption, peptides of the invention can be released from a capsule after passing through the harsh proteolytic environment of the stomach.

The active ingredient may be administered all at once, or may be divided into a number of smaller doses to be administered at intervals of time, or as a controlled release formulation. The term "controlled release formulation" encompasses formulations that allow the continuous delivery of a synthetic peptide amide of the invention to a subject over a period of time, for example, several days to weeks. Such formulations may be administered subcutaneously or intramuscularly and allow for the continual steady state release of a predetermined amount of compound in the subject over time. The controlled release formulation of kappa opioid receptor agonist peptide amide may be, for example, a formulation of drug containing polymeric microcapsules, such as those described in U.S. Pat. Nos. 4,677,191 and 4,728,721, incorporated herein by reference. The concentration of the pharmaceutically active compound is adjusted so that administration provides an effective amount to produce a desired effect. The exact dose depends on the age, weight and condition of the patient or animal, as is known in the art. For any particular subject, specific dosage regimens can be adjusted over time according to the individual need and the professional judgment of the person administering or supervising the administration of the formulations. Thus, the concentration ranges set forth herein are exemplary only and are not intended to limit the scope or practice of the claimed invention.

The compositions can be administered for prophylaxis or treatment of individuals suffering from, or at risk of a disease or a disorder. Prophylaxis is defined as a measure designed to preserve the health of an individual. For therapeutic applications, a pharmaceutical composition is typically administered to a subject suffering from a disease or disorder, in an amount sufficient to inhibit, prevent, or ameliorate the disease or disorder. An amount adequate to accomplish this is defined as a "therapeutically effective dose."

The pharmaceutical formulations of the invention can be administered to a mammal for prophylactic or therapeutic purposes. The mammal can be any mammal, such as a domesticated or feral mammal, or even a wild mammal. The mammal can be any primate, ungulate, canine or feline. For instance, and without limitation, the mammal may be a pet or companion animal, such as a dog or a cat; a high-value mammal such as a thoroughbred horse or a show animal; a farm animal, such as a cow, a goat, a sheep or pig; or a primate such as an ape, gorilla, orangutan, lemur, monkey or chimpanzee. A suitable mammal for prophylaxis or treatment using the pharmaceutical formulations of the invention is a human.

The pharmaceutical formulations of the invention can be administered to a mammal having a disease or condition treatable by activation of the kappa opioid receptor. Alternatively, the pharmaceutical compositions can be administered as prophylactics to a mammal having a risk of contracting or developing a disease or condition preventable by activation of the kappa opioid receptor. Diseases or conditions that can be treated or prevented by administration of the pharmaceutical compositions of the invention include, without limitation, any condition that can be ameliorated by activation of the kappa opioid receptor, including such conditions as pain, inflammation, pruritus, hyponatremia, hypokalemia, congestive heart failure, liver cirrhosis, nephrotic syndrome, hypertension, edema, ileus, tussis and glaucoma.

In a particular embodiment, the pharmaceutical compositions of the invention can be co-administered with or can include one or more other therapeutic compounds or adjuvants, such as but not limited to other opioids, cannabinoids, antidepressants, anticonvulsants, neuroleptics, antihistamines, acetaminophen, corticosteroids, ion channel blocking agents, non-steroidal anti-inflammatory drugs (NSAIDs), and diuretics, many of which are synergistic in effect with the synthetic peptide amides of the invention.

The invention further provides a method of treating or preventing a kappa opioid receptor-associated disease or condition in a mammal, wherein the method includes administering to the mammal a composition containing an effective amount of a kappa opioid receptor agonist peptide amide in a formulation of the invention. The mammal can be any mammal, such as a domesticated or feral mammal, or even a wild mammal. Alternatively, the mammal can be a primate, an ungulate, a canine or a feline. For instance, and without limitation, the mammal may be a pet or companion animal, such as a high-value mammal such as a thoroughbred or show animal; a farm animal, such as a cow, a goat, a sheep or pig; or a primate such as an ape or monkey. In one particular aspect, the mammal is a human.

The kappa opioid receptor-associated disease, disorders or condition preventable or treatable with the kappa opioid receptor agonist peptide amide in a formulation of the invention can be any kappa opioid receptor-associated condition, including but not limited to acute or chronic pain, inflammation, pruritus, hyponatremia, edema, ileus, tussis and glaucoma. For instance, the kappa opioid receptor-associated pain can be neuropathic pain, somatic pain, visceral pain or cutaneous pain. Some diseases, disorders, or conditions are associated with more than one form of pain, e.g., postoperative pain can have any or all of neuropathic, somatic, visceral, and cutaneous pain components, depending upon the type and extent of surgical procedure employed.

The kappa opioid receptor-associated inflammation can be any inflammatory disease or condition including, but not limited to sinusitis, rheumatoid arthritis tenosynovitis, bursitis, tendonitis, lateral epicondylitis, adhesive capsulitis, osteomyelitis, osteoarthritic inflammation, inflammatory bowel disease (IBD), irritable bowel syndrome (IBS), ocular inflammation, otitic inflammation or autoimmune inflammation.

The kappa opioid receptor-associated pruritus can be any pruritic disease or condition such as, for instance, ocular pruritus (used interchangeably with the term pruritis), e.g., associated with conjunctivitis, otitic pruritus, pruritus associated with end-stage renal disease also known as uremic pruritus, where many patients are receiving kidney dialysis, and other forms of cholestasis, including primary biliary cirrhosis, intrahepatic cholestasis of pregnancy, chronic cholestatic liver disease, uremia, malignant cholestasis, jaundice, as well as dermatological conditions such as eczema (dermatitis), including atopic or contact dermatitis, psoriasis, polycythemia vera, lichen planus, lichen simplex chronicus, pediculosis (lice), thyrotoxicosis, tinea pedis, urticaria, scabies, vaginitis, anal pruritus associated with hemorrhoids and, as well as insect bite pruritus and drug-induced pruritus, such as mu opioid-induced pruritus.

The kappa opioid receptor-associated edema can be any edematous disease or condition such as, for instance, edema due to congestive heart disease or to a syndrome of inappropriate antidiuretic hormone (ADH) secretion. Kappa opioid receptor-associated ileus can be any ileus disease or condition including, but not limited to, post-operative ileus and opioid-induced bowel dysfunction. Kappa opioid receptor-associated neuropathic pain can be any neuropathic pain, such as, for instance, trigeminal neuralgia, diabetic pain, viral pain such as herpes zoster-associated pain, chemotherapy-induced pain, nerve-encroaching metastatic cancer pain, neuropathic pain associated with traumatic injury and surgical procedures, as well as variants of headache pain that are thought to have a neuropathic component, e.g., migraine.

Kappa opioid-associated pain also includes ocular pain, such as that following photo-refractive keratectomy (PRK), ocular laceration, orbital floor fracture, chemical burns, corneal abrasion or irritation, or pain associated with conjunctivitis, corneal ulcers, scleritis, episcleritis, sclerokeratitis, herpes zoster ophthalmicus, interstitisal keratitis, acute iritis, keratoconjunctivitis sicca, orbital cellulites, orbital pseudotumor, pemphigus, trachoma or uveitis.

Kappa opioid-associated pain also includes throat pain, particularly associated with inflammatory conditions, such as allergic rhinitis, acute bronchitis, the common cold, contact ulcers, herpes simplex viral lesions, infectious mononucleosis, influenza, laryngeal cancer, acute laryngitis, acute necrotizing ulcerative gingivitis, peritonsillar abscess, pharyngeal burns, pharyngitis, reflux laryngopharyngitis, acute sinusitis, and tonsillitis.

In addition, kappa opioid receptor-associated pain can be arthritic pain, kidney-stone, urinary tract stone, gallstone, and bile duct stone pain, dysmenorrhea, uterine cramping, endometriosis, mastitis, dyspepsia, post-surgical pain (such as, for instance, from appendectomy, open colorectal surgery, hernia repair, prostatectomy, colonic resection, gastrectomy, splenectomy, colectomy, colostomy, pelvic laparoscopy, tubal ligation, hysterectomy, vasectomy or cholecystectomy), post medical procedure pain (such as, for instance, after colonoscopy, cystoscopy, hysteroscopy or cervical or endometrial biopsy), otitic pain, breakthrough cancer pain, and pain associated with a GI disorder such as IBD or IBS or other inflammatory conditions, particularly of the viscera (e.g., gastro-esophageal reflux disease, pancreatitis, acute polynephritis, ulcerative colitis, acute pyelonephritis, cholecystitis, cirrhosis, hepatic abscess, hepatitis, duodenal or gastric ulcer, esophagitis, gastritis, gastroenteritis, colitis, diverticulitis, intestinal obstruction, ovarian cyst, pelvic inflammatory disease, perforated ulcer, peritonitis, prostatitis, interstitial cystitis), or exposure to toxic agents, such as insect toxins, or inflammation due to the effects of drugs such as salicylates or NSAIDs.

The present invention provides a method of treating or preventing a kappa opioid receptor-associated disease or condition in a mammal, such as a human, wherein the method includes administering to the mammal a formulation of the invention comprising an effective amount of a kappa opioid receptor agonist peptide amide, and an absorption enhancer of the invention. In another embodiment the kappa opioid receptor-associated condition is pain, inflammation (such as rheumatoid arthritic inflammation, osteoarthritic inflammation, IBD inflammation, IBS inflammation, ocular inflammation, otitic inflammation or autoimmune inflammation), pruritus (such as atopic dermatitis, kidney-dialysis-associated pruritus, ocular pruritus, otitic pruritus, insect bite pruritus, or opioid-induced pruritus), edema, ileus, tussis or glaucoma. In one aspect, the pain is a neuropathic pain (such as trigeminal neuralgia, migraine, diabetic pain, viral pain, chemotherapy-induced pain or metastatic cancer pain), a somatic pain, a visceral pain or a cutaneous pain. In another aspect the pain is arthritic pain, kidney-stone pain, uterine cramping, dysmenorrhea, endometriosis, dyspepsia, post-surgical pain, post medical procedure pain, ocular pain, otitic pain, breakthrough cancer pain or pain associated with a GI disorder, such as IBD or IBS. In another aspect the pain is pain associated with surgery, wherein the surgery is pelvic laparoscopy, tubal ligation, hysterectomy and cholecystecomy. Alternatively, the pain can be pain associated with a medical procedure, such as for instance, colonoscopy, cystoscopy, hysteroscopy or endometrial biopsy. In a specific aspect, the atopic dermatitis can be psoriasis, eczema or contact dermatitis. In another specific aspect, the ileus is post-operative ileus or opioid-induced bowel dysfunction.

Another form of kappa opioid receptor-associated pain treatable or preventable with the synthetic peptide amides of the invention is hyperalgesia. In one embodiment, the method includes administering an effective amount of a synthetic peptide amide of the invention to a mammal suffering from or at risk of developing hyperalgesia to prevent, ameliorate or completely alleviate the hyperalgesia.

Kappa opioid receptor-associated pain includes hyperalgesia, which is believed to be caused by changes in the milieu of the peripheral sensory terminal occur secondary to local tissue damage. Tissue damage (e.g., abrasions, burns) and inflammation can produce significant increases in the excitability of polymodal nociceptors (C fibers) and high threshold mechanoreceptors. This increased excitability and exaggerated responses of sensory afferents is believed to underlie hyperalgesia, where the pain response is the result of an exaggerated response to a stimulus. The importance of the hyperalgesic state in the post-injury pain state has been repeatedly demonstrated and appears to account for a major proportion of the post-injury/inflammatory pain state.

In another embodiment the kappa opioid receptor-associated condition is pain, inflammation (such as rheumatoid arthritic inflammation, osteoarthritic inflammation, IBD inflammation, IBS inflammation, ocular inflammation, otitic inflammation or autoimmune inflammation), pruritus (such as atopic dermatitis, kidney-dialysis-associated pruritus, ocular pruritus, otitic pruritus, insect bite pruritus, or opioid-induced pruritus), edema, ileus, tussis or glaucoma. In one aspect, the pain is a neuropathic pain (such as trigeminal neuralgia, migraine, diabetic pain, viral pain, chemotherapy-induced pain or metastatic cancer pain), a somatic pain, a visceral pain or a cutaneous pain. In another aspect the pain is arthritic pain, kidney-stone pain, uterine cramping, dysmenorrhea, endometriosis, dyspepsia, post-surgical pain, post medical procedure pain, ocular pain, otitic pain, breakthrough cancer pain or pain associated with a GI disorder, such as IBD or IBS. In another aspect the pain is pain associated with surgery, wherein the surgery is pelvic laparoscopy, tubal ligation, hysterectomy and cholecystecomy. Alternatively, the pain can be pain associated with a medical procedure, such as for instance, colonoscopy, cystoscopy, hysteroscopy or endometrial biopsy. In a specific aspect, the atopic dermatitis can be psoriasis, eczema or contact dermatitis. In another specific aspect, the ileus is post-operative ileus or opioid-induced bowel dysfunction.

In another embodiment the kappa opioid receptor-associated condition is a kappa opioid receptor-associated condition preventable or treatable by sodium and potassium-sparing diuresis, also known as aquaresis. An example of such kappa opioid receptor-associated conditions preventable or treatable by administering a kappa opioid receptor agonist peptide amide in the formulation of the invention includes edema. The edema may be due to any of a variety of diseases or conditions, such as congestive heart disease or syndrome of inappropriate ADH secretion.

In another embodiment the kappa opioid receptor-associated condition is hyponatremia or other edematous disease. The kappa opioid receptor-associated hyponatremia or edema can be any hyponatremic or edematous disease or condition such as, for instance, hyponatremia and edema associated with congestive heart failure or to a syndrome of inappropriate antidiuretic hormone (ADH) secretion, or hyponatremia that is associated with intensive diuretic therapy with thiazides and/or loop diuretics. The synthetic peptide amides of the invention exhibit a significant sodium-sparing and potassium-sparing aquaretic effect, which is beneficial in the treatment of edema-forming pathological conditions associated with hyponatremia and/or hypokalemia. Accordingly, the synthetic peptide amides of the invention also have utility in methods of treating or preventing hyponatremia-related conditions, examples of which are provided below. Hyponatremia-related conditions can be categorized according to volume status as hypervolemic, euvolemic, or hypovolemic.

Hypervolemic hyponatremia is usually caused by an increase in total body water level as may be observed in cases of congestive heart failure, nephrotic syndrome and hepatic cirrhosis. Euvolemic hyponatremia is often found in the syndrome of inappropriate antidiuretic hormone (ADH) secretion and may also be associated with pneumonia, small-cell lung cancer, polydipsia, cases of head injury, and organic causes (e.g., use of certain drugs, such as haloperidol) or a psychogenic cause. Hypovolemic hyponatremia is due to a relative decrease in total body sodium level and may be associated with, for instance and without limitation, diuretic use, cases of interstitial nephritis or excessive sweating.

The kappa opioid receptor-associated hyponatremia can be any disease or condition where hyponatremia (low sodium condition) is present, e.g., in humans, when the sodium concentration in the plasma falls below 135 mmol/L, an abnormality that can occur in isolation or, more frequently, as a complication of other medical conditions, or as a consequence of using medications that can cause sodium depletion.

In addition to these conditions, numerous other conditions are associated with hyponatremia including, without limitation: neoplastic causes of excess ADH secretion, including carcinomas of lung, duodenum, pancreas, ovary, bladder, and ureter, thymoma, mesothelioma, bronchial adenoma, carcinoid, gangliocytoma and Ewing's sarcoma; infections such as: pneumonia (bacterial or viral), abscesses (lung or brain), cavitation (aspergillosis), tuberculosis (lung or brain), meningitis (bacterial or viral), encephalitis and AIDS; vascular causes such as: cerebrovascular occlusions or hemorrhage and cavernous sinus thrombosis; neurologic causes such as: Guillain-Barre syndrome, multiple sclerosis, delirium tremens, amyotrophic lateral sclerosis, hydrocephalus, psychosis, peripheral neuropathy, head trauma (closed and penetrating), CNS tumors or infections and CNS insults affecting hypothalamic osmoreceptors; congenital malformations including: agenesis of corpus callosum, cleftlip/palate and other midline defects; metabolic causes such as: acute intermittent porphyria, asthma, pneurothorax and positive-pressure respiration; drugs such as: thiazide diuretics, acetaminophen, barbiturates, cholinergic agents, estrogen, oral hypoglycemic agents, vasopressin or desmopressin, high-dose oxytocin, chlorpropamide, vincristine, carbamezepine, nicotine, phenothiazines, cyclophosphamide, tricyclic antidepressants, monoamine oxidase inhibitors and serotonin reuptake inhibitors; administration of excess hypotonic fluids, e.g., during hospitalization, surgery, or during or after athletic events (i.e., exercise-associated hyponatremia), as well as use of low-sodium nutritional supplements in elderly individuals.

Other conditions associated with hyponatremia include renal failure, nephrotic syndrome (membranous nephropathy and minimal change disease), cachexia, malnutrition, rhabdomyolysis, surgical procedures, elective cardiac catheterization, blood loss, as well as hypercalcemia, hypokalemia, and hyperglycemia with consequent glycosuria leading to osmotic diuresis.

The invention also provides a method of treating or preventing a neuro-degenerative disease or condition in a mammal, such as a human, wherein the method includes administering to the mammal a formulation that includes an effective amount of a kappa opioid receptor agonist peptide amide and an absorption enhancer as described above. The neurodegenerative disease or condition can be any neurodegenerative disease or condition, such as for instance, ischemia, anoxia, stroke, brain injury, spinal cord injury or reperfusion injury. Alternatively, the neurodegenerative disease or condition can be a neurodegenerative disease of the eye. Particular neurodegenerative diseases of the eye treatable or preventable by the method of the invention include glaucoma, macular degeneration, retinal ischemic disease and diabetic neuropathy.

In certain embodiments the invention provides methods of prevention or treatment of certain neuronal diseases and conditions, such as diseases and conditions having a neurodegenerative component. Synthetic peptide amides of the invention can be administered in an amount effective to protect neuronal cells against the effects of pathology or injury that would lead to neurodegeneration and/or neuronal cell death of the untreated cells. Progression of these diseases and conditions is believed to involve neurodegeneration or neuronal cell death, for example by programmed cell death (apoptosis) in which the neuronal cells are committed to a pathway that without intervention would lead to cell death. It has been found that development or progression of these diseases and conditions can be prevented, or at least slowed, by treatment with kappa opioid receptor agonists.

In other embodiments the invention provides methods of prevention or treatment of certain cardiovascular diseases and conditions having a cellular degenerative component. Formulations comprising a kappa opioid receptor agonist peptide amide and an absorption enhancer of the invention can be administered in an amount effective to protect myocardial cells against the effects of pathology or injury that would lead to degeneration and/or cell death of the untreated cells. For example, several cardiovascular diseases or conditions can be prevented or treated by administration of an effective amount of the formulations of the invention. Such cardiovascular diseases and conditions include, without limitation, coronary heart disease, ischemia, cardiac infarct, reperfusion injury and arrhythmia.

Diseases and conditions of other tissues and organs that can be prevented or treated by administration of an effective amount of the synthetic peptide amides of the invention include, but are not limited to ischemia, anoxia, stroke, brain or spinal cord injury and reperfusion injury.

The invention also provides a bioactive composition that includes a biologically active peptide embedded in an oligomeric saccharide forming a particle including the stabilized biologically active peptide. In one embodiment the bioactive composition that includes a biologically active peptide embedded in an oligomeric saccharide forming a particle including the stabilized biologically active peptide also includes one or more of the following: a salt of a carboxylic acid, an absorption enhancer, a binding agent, a chelating agent and a pharmaceutically acceptable carrier or excipient. The salt of a carboxylic acid can be any suitable salt of a carboxylic acid, such as but not limited to sodium citrate. The absorption enhancer can be any suitable absorption enhancer, such as for instance, lauroyl L-carnitine. The binding agent can be any suitable binding agent to promote cohesiveness, such as cellulose, methyl or ethyl cellulose, starch, gelatin, PVP, PEG, polyvinyl alcohols and polymethacrylates. The chelating agent, can be any suitable chelating agent such as, and without limitation, succinic acid or EDTA. Commonly used pharmaceutically acceptable carriers or excipients include calcium salts, such as calcium chloride, calcium phosphate and calcium sulfate; metallic oxides, sugars, sugar alcohols and sweeteners to name a just few of those well known in the art.

The biologically active peptide can be any suitable a biologically active peptide, such as, and without limitation, a kappa opioid receptor agonist peptide. In one embodiment the a kappa opioid receptor agonist peptide can be a D-amino acid tetrapeptide amide as described in U.S. Pat. Nos. 7,402,564, 7,713,937 and 7,842,662.

In one embodiment, the D-amino acid tetrapeptide amide is the kappa opioid receptor agonist compound: D-Phe-D-Phe-D-Leu-D-Lys-[ω(4-aminopiperidine-4-carboxylic acid)]-OH also referred to in the literature as CR845 (difelikefalin).

The oligomeric saccharide in which the biologically active peptide is embedded can be any suitable oligomeric saccharide, such as for instance an oligomeric saccharide such as a disaccharide. In one embodiment the disaccharide may include a glucose monomer such as dextrose. In another embodiment the disaccharide may be a glucose dimer such as trehalose.

In one embodiment the biologically active peptide is a tetrapeptide amide kappa opioid receptor agonist embedded in a composition comprising trehalose to form a particle comprising a stabilized biologically active peptide, wherein the particles have an average diameter of from about 2 microns to about 100 microns. In another embodiment the particles have an average diameter of from about 5 microns to about 50 microns.

In another embodiment, the invention further provides a bioactive composition that includes a biologically active peptide embedded in an oligomeric saccharide forming a particle including the stabilized biologically active peptide, wherein the particle is dispersed in a liquid suspension that includes one or more medium chain fatty acids or one or more salts of a medium chain fatty acid and a medium chain fatty acid glyceride. In one embodiment the liquid suspension includes a medium chain fatty acid ($C_6$-$C_{12}$ fatty acid). In another embodiment, the liquid suspension includes a medium chain ($C_8$-$C_{12}$) fatty acid. In a further embodiment the liquid suspension includes a medium chain ($C_6$-$C_{12}$) fatty acid triglyceride. In another embodiment the liquid suspension includes a medium chain ($C_8$-$C_{12}$) fatty acid triglyceride.

In one embodiment, the liquid suspension including the particle formed from the biologically active peptide embedded in an oligomeric saccharide includes at least one ($C_6$-$C_{12}$) fatty acid and at least one ($C_6$-$C_{12}$) fatty acid triglyceride. The ($C_6$-$C_{12}$) chain fatty acid can be a ($C_8$-$C_{12}$) fatty acid and the ($C_6$-$C_{12}$) chain fatty acid triglyceride can be a ($C_8$-$C_{12}$) fatty acid triglyceride. The ($C_8$-$C_{12}$) fatty acid and the ($C_6$-$C_{12}$) chain fatty acid triglyceride can be a ($C_8$-$C_{12}$) fatty acid triglyceride can be a Miglyol® such as for instance Miglyol®812. The suspension can also include one or more of an emulsifying agent, a salt of a carboxylic acid, an absorption enhancer, a binding agent and a pharmaceutically acceptable carrier or excipient.

In another embodiment, the invention provides a bioactive composition that includes a biologically active peptide, such as the kappa opioid receptor agonist, CR845 embedded in an oligomeric saccharide forming a particle including the stabilized biologically active peptide, wherein the oligomeric saccharide includes a disaccharide such as trehalose, the 1,1-α-glycoside linked glucose dimer. Such trehalose/CR845 particles are useful as medicinal dry powders, incorporated into blends of medicinal dry powders, or compressed into tablets with solid absorption enhancers, such as lauroyl L-carnitine, and/or citric acid amongst many other well-known absorption enhancers without the use of a medium chain fatty acid, salt of a medium chain fatty acid or a medium chain fatty acid glyceride.

The invention further provides a bioactive composition including a biologically active peptide embedded in an oligomeric saccharide particle to form a stabilized biologically active peptide particle, wherein the oligomeric saccharide enhances the stability of the biologically active peptide over at least a year at 25° C. In one embodiment, the biologically active peptide is a kappa opioid receptor agonist comprising one or more D-amino acids and the oligomeric disaccharide comprises glucose. The kappa opioid receptor agonist comprising one or more D-amino acids can be any suitable kappa opioid receptor agonist, such as a tetrapeptide amide kappa opioid receptor agonist, such as for instance CR845 and the oligomeric disaccharide comprising glucose can be for instance, and without limitation, trehalose.

The bioactive composition of the invention including a biologically active peptide embedded in an oligomeric saccharide particle can be included in a pharmaceutically acceptable tablet, caplet, capsule, powder, or liquid suspension for administration as a medicament. The pharmaceutically acceptable tablet, caplet, capsule, powder, or liquid suspension may further include one or more of a salt of a carboxylic acid, an absorption enhancer, a binding agent and a pharmaceutically acceptable carrier or excipient. In one embodiment the pharmaceutically acceptable tablet, caplet, capsule, powder, or liquid suspension may include sodium citrate as the carboxylic acid. In another embodiment the pharmaceutically acceptable tablet, caplet, capsule, powder, or liquid suspension may include lauroyl L-carnitine as an absorption enhancer.

In a further embodiment, the pharmaceutically acceptable tablet, caplet, capsule, powder, or liquid suspension may include CR845 as the a kappa opioid receptor agonist biologically active peptide embedded in an oligomeric saccharide in the form of stabilized particles having a diameter of about 50 microns. In some embodiments, the oligomeric saccharide is a glucose-containing oligomeric saccharide, such as trehalose.

The formulations including the kappa opioid receptor agonist peptide amides and absorption enhancers of the invention can be administered by methods disclosed herein for the treatment or prevention of any hyperalgesic condition, such as, but without limitation, a hyperalgesic condition associated with allergic dermatitis, contact dermatitis, skin ulcers, inflammation, rashes, fungal irritation and hyperalgesic conditions associated with infectious agents, burns, abrasions, bruises, contusions, frostbite, rashes, acne, insect bites/stings, skin ulcers, mucositis, gingivitis, bronchitis, laryngitis, sore throat, shingles, fungal irritation, fever blisters, boils, Plantar's warts, surgical procedures or vaginal lesions.

Moreover, the formulations including the kappa opioid receptor agonist peptide amides and absorption enhancers of the invention can be administered by methods disclosed herein for the treatment or prevention of any hyperalgesic condition associated with burns, abrasions, bruises, abrasions (such as corneal abrasions), contusions, frostbite, rashes, acne, insect bites/stings, skin ulcers (for instance, diabetic ulcers or a decubitus ulcers), mucositis, inflammation, gingivitis, bronchitis, laryngitis, sore throat, shingles, fungal irritation (such as athlete's foot or jock itch), fever blisters, boils, Plantar's warts or vaginal lesions (such as vaginal lesions associated with mycosis or sexually transmitted diseases).

Hyperalgesic conditions associated with post-surgery recovery can also be addressed by administration of formulations including the kappa opioid receptor agonist peptide amides and absorption enhancers of the invention. The hyperalgesic conditions associated with post-surgery recovery can be any hyperalgesic conditions associated with post-surgery recovery, such as for instance, radial keratectomy, tooth extraction, lumpectomy, episiotomy, laparoscopy and arthroscopy. Hyperalgesic conditions associated with inflammation can also be addressed by administration of formulations including the kappa opioid receptor agonist peptide amides and absorption enhancers of the invention.

EXAMPLES

The following listing of D-amino acid peptide amides listed as compounds (1)-(103) can be used in the formulations of the present invention:

D-Amino Acid Peptide Amides

Examples (1)-(103)

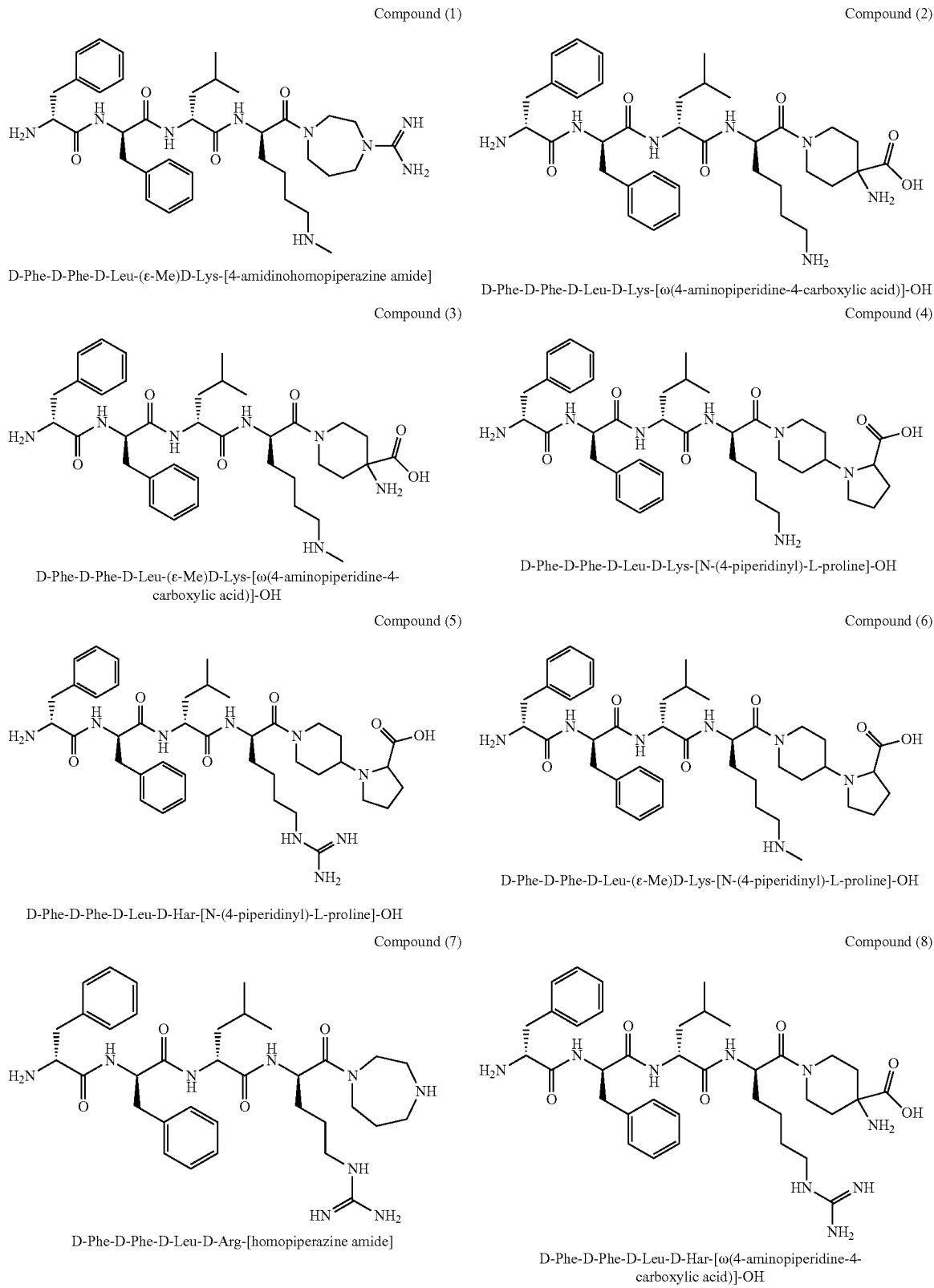

Compound (1): D-Phe-D-Phe-D-Leu-(ε-Me)D-Lys-[4-amidinohomopiperazine amide]

Compound (2): D-Phe-D-Phe-D-Leu-D-Lys-[ω(4-aminopiperidine-4-carboxylic acid)]-OH Compound (3): D-Phe-D-Phe-D-Leu-(ε-Me)D-Lys-[ω(4-aminopiperidine-4-carboxylic acid)]-OH Compound (4): D-Phe-D-Phe-D-Leu-D-Lys-[N-(4-piperidinyl)-L-proline]-OH Compound (5): D-Phe-D-Phe-D-Leu-D-Har-[N-(4-piperidinyl)-L-proline]-OH Compound (6): D-Phe-D-Phe-D-Leu-(ε-Me)D-Lys-[N-(4-piperidinyl)-L-proline]-OH Compound (7): D-Phe-D-Phe-D-Leu-D-Arg-[homopiperazine amide]

Compound (8): D-Phe-D-Phe-D-Leu-D-Har-[ω(4-aminopiperidine-4-carboxylic acid)]-OH -continued Compound (9)

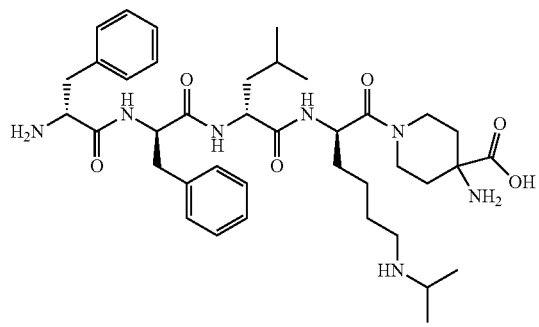

D-Phe-D-Phe-D-Leu-(ε-iPr)D-Lys-[ω(4-aminopiperidine-4-carboxylic acid)]-OH

Compound (10)

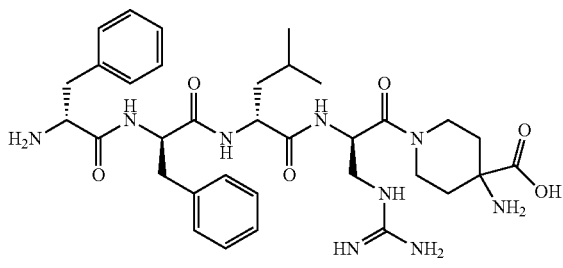

D-Phe-D-Phe-D-Leu-(β-amidino)D-Dap-[ω(4-aminopiperidine-4-carboxylic acid)]-OH

Compound (11)

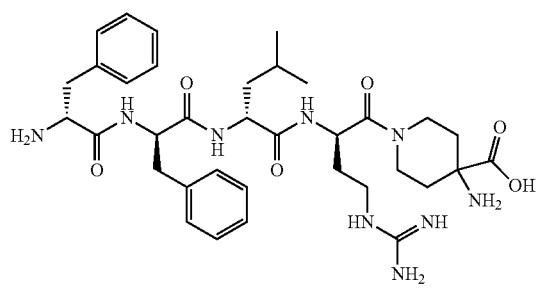

D-Phe-D-Phe-D-Leu-D-Nar-[ω(4-aminopiperidine-4-carboxylic acid)]-OH

Compound (12)

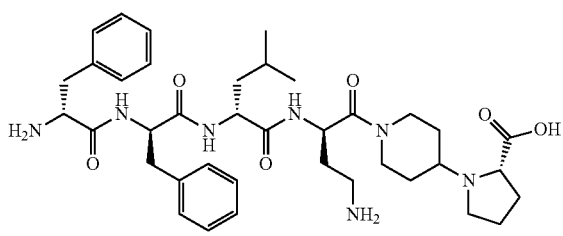

D-Phe-D-Phe-D-Leu-D-Dbu-[N-(4-piperidinyl)-L-proline]-OH

Compound (13)

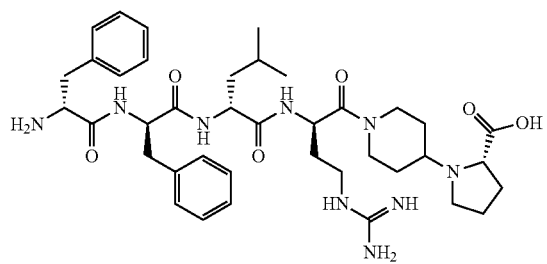

D-Phe-D-Phe-D-Leu-D-Nar-[N-(4-piperidinyl)-L-proline]-OH

Compound (14)

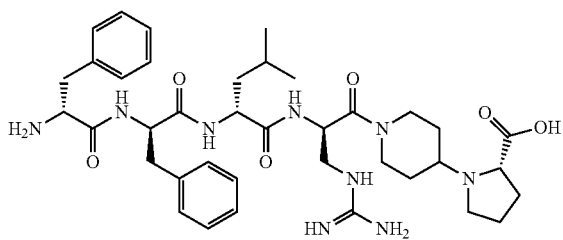

D-Phe-D-Phe-D-Leu-D-Dap(amidino)-[N-(4-piperidinyl)-L-proline]-OH

Compound (15)

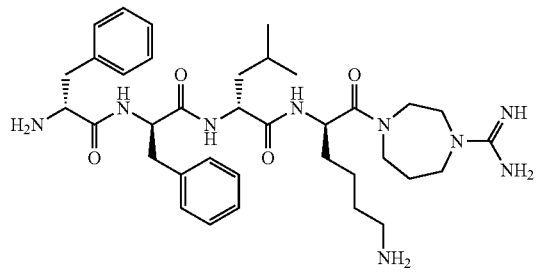

D-Phe-D-Phe-D-Leu-D-Lys-[4-amidinohomopiperazine amide]

Compound (16)

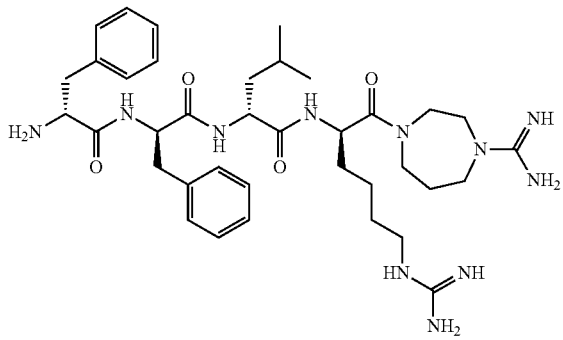

D-Phe-D-Phe-D-Leu-D-Har-[4-amidinohomopiperazine amide]

Compound (17)

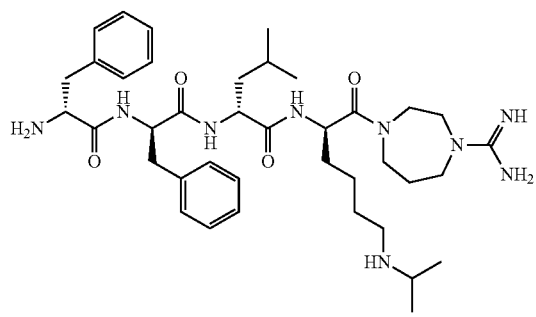

D-Phe-D-Phe-D-Leu-(ε-iPr)D-Lys-[4-amidinohomo-piperazine amide]

Compound (18)

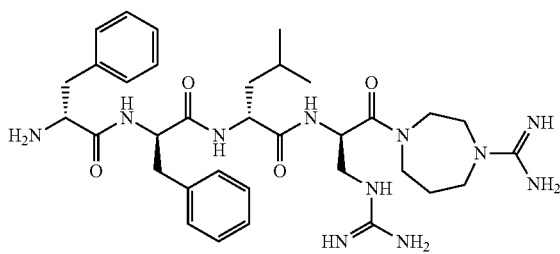

D-Phe-D-Phe-D-Leu-(β-amidino)D-Dap-[4-amidinohomopiperazine amide]

Compound (19)

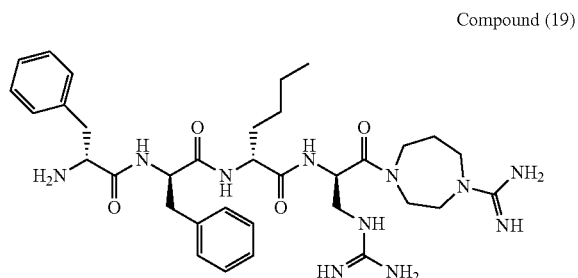

D-Phe-D-Phe-D-Nle-(β-amidino)D-Dap-[4-amidinohomopiperazine amide]

Compound (20)

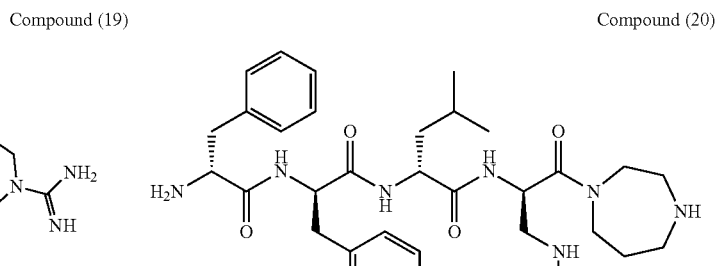

D-Phe-D-Phe-D-Leu-(β-amidino)D-Dap-[homopiperazine amide]

Compound (21)

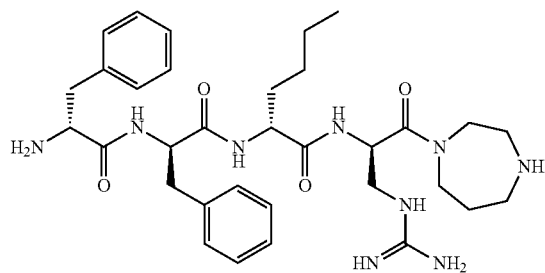

D-Phe-D-Phe-D-Nle-(β-amidino)D-Dap-[homopiperazine amide]

Compound (22)

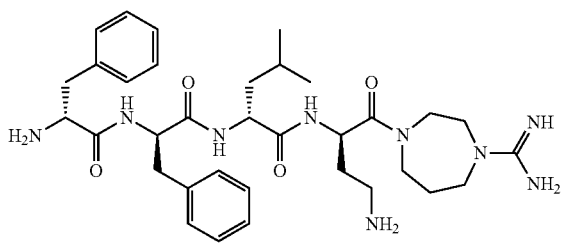

D-Phe-D-Phe-D-Leu-D-Dbu-[4-amidinohomopiperazine amide]

Compound (23)

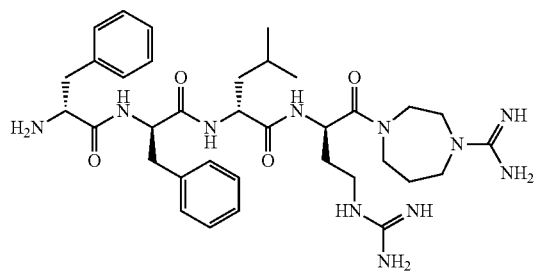

D-Phe-D-Phe-D-Leu-D-Nar-[4-amidinohomopiperazine amide]

Compound (24)

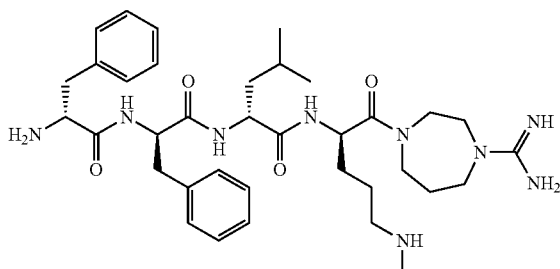

D-Phe-D-Phe-D-Leu-D-Arg-[4-amidinohomopiperazine amide]

-continued

Compound (25)

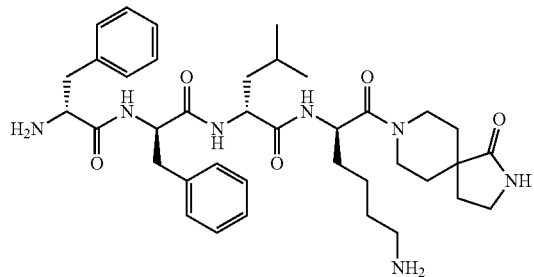

D-Phe-D-Phe-D-Leu-D-Lys-[2,8-diazaspiro[4,5]decan-1-one amide]

Compound (26)

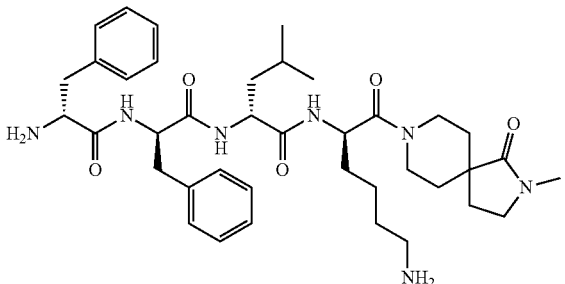

D-Phe-D-Phe-D-Leu-D-Lys-[2-methyl-2,8-diazaspiro[4,5]decan-1-one amide]

Compound (27)

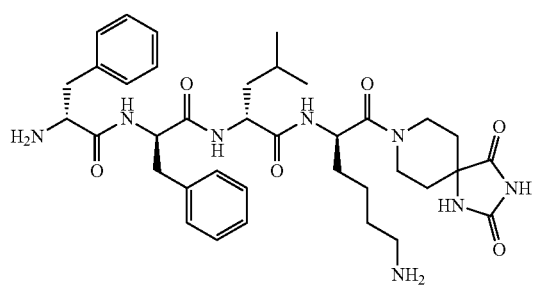

D-Phe-D-Phe-D-Leu-D-Lys-[1,3,8-triazaspiro[4,5]decan-1-one amide]

Compound (28)

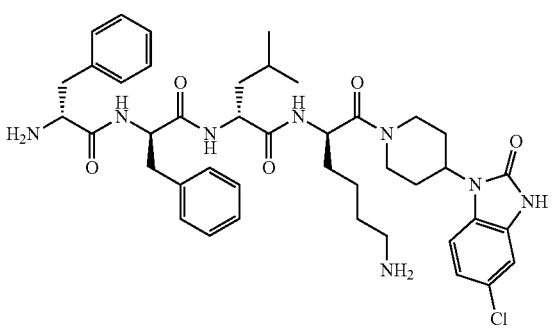

D-Phe-D-Phe-D-Leu-D-Lys-[5-chloro-1-(piperidin-4-yl)-1H-benzo[d]imidazol-2(3H)H-one amide]

Compound (29)

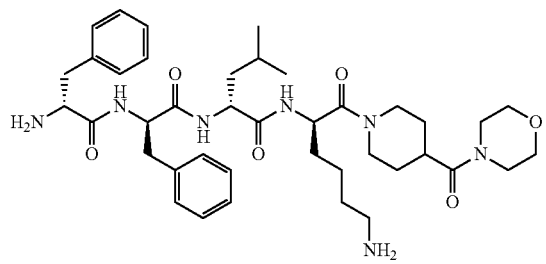

D-Phe-D-Phe-D-Leu-D-Lys-[morpholino(piperidin-4-yl)methanone amide]

Compound (30)

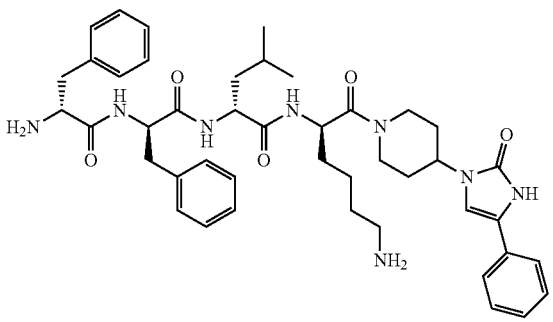

D-Phe-D-Phe-D-Leu-D-Lys-[4-phenyl-1-(piperidin-yl-1H-imidazol-2(3H)-one amide]

Compound (31)

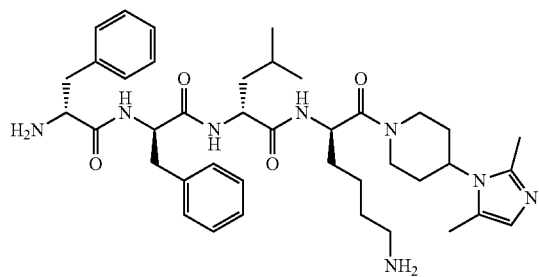

D-Phe-D-Phe-D-Leu-D-Lys-[4-(3,5-dimethyl-4H-1,2,4-triazol-4-yl)piperidine amide]

Compound (32)

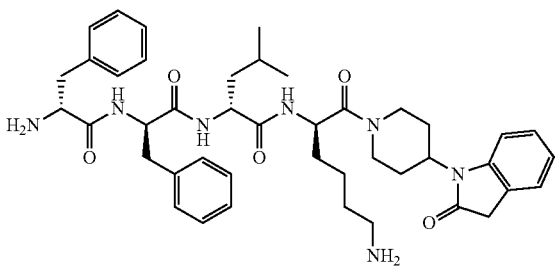

D-Phe-D-Phe-D-Leu-D-Lys-[1-(piperidin-4-yl)indolin-2-one amide]

-continued

Compound (33)

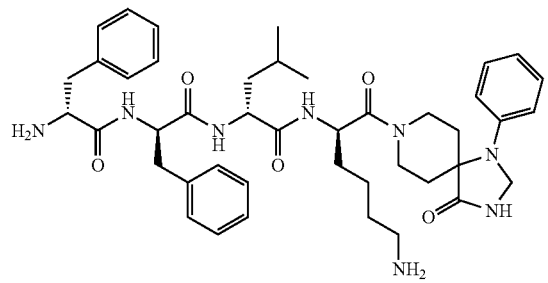

D-Phe-D-Phe-D-Leu-D-Lys-[1-phenyl-1,3,8-triazaspiro[4.5]decan-4-amide]

Compound (34)

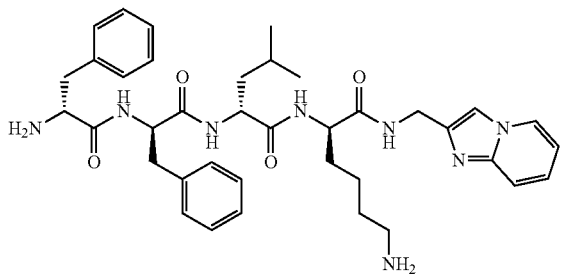

D-Phe-D-Phe-D-Leu-D-Lys-[imidazo[1,2-a]pyridine-2-ylmethyl amide]

Compound (35)

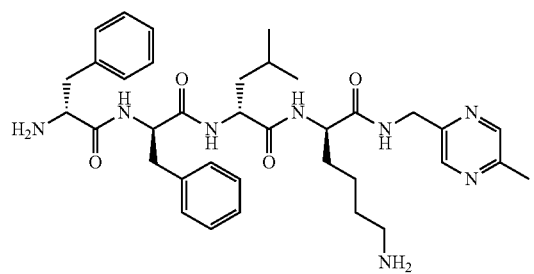

D-Phe-D-Phe-D-Leu-D-Lys-[(5-methylpyrazin-2-yl)methyl amide]

Compound (36)

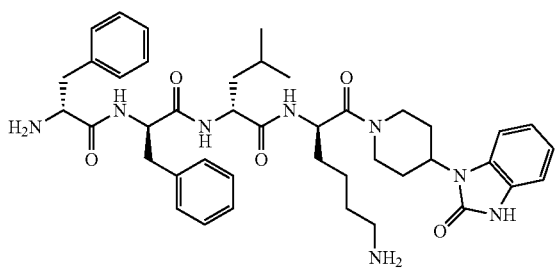

D-Phe-D-Phe-D-Leu-D-Lys-[1-(piperidin-4-yl)-1H-benzo[d]imidazol-2(3H)-one amide]

Compound (37)

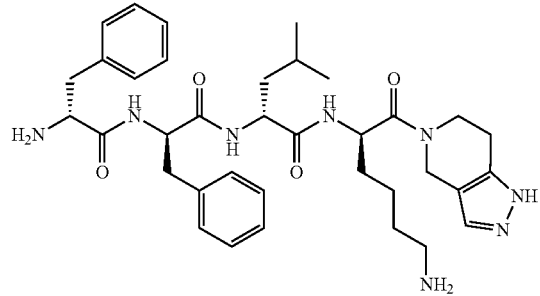

D-Phe-D-Phe-D-Leu-D-Lys-[4,5,6,7-tetrahydro-1H-pyrazolo[4,3-c]pyridine amide]

Compound (38)

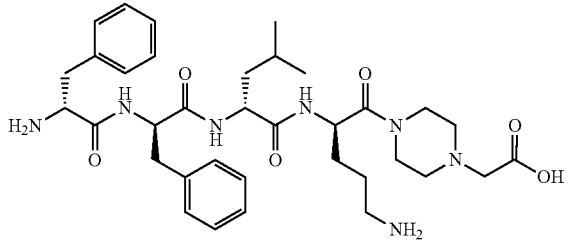

D-Phe-D-Phe-D-Leu-D-Orn-[4-(2-aminoethyl)-1-carboxymethyl-piperazine]-OH

Compound (39)

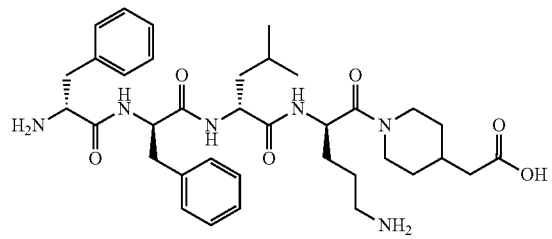

D-Phe-D-Phe-D-Leu-D-Orn-[4-carboxymethyl-piperadine]-OH

Compound (40)

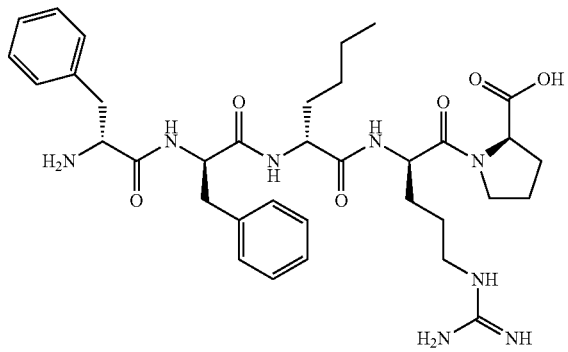

D-Phe-D-Phe-D-Nle-D-Arg-D-Pro-OH

-continued

Compound (41)

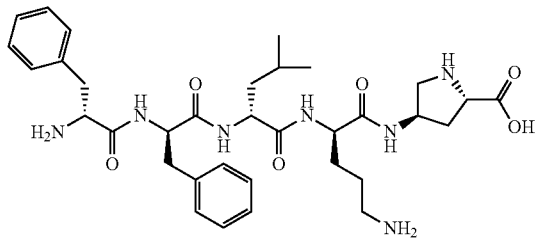

D-Phe-D-Phe-D-Leu-D-Orn-[(2S,4R)-4-amino-pyrrolidine-2-carboxylic acid]-OH

Compound (42)

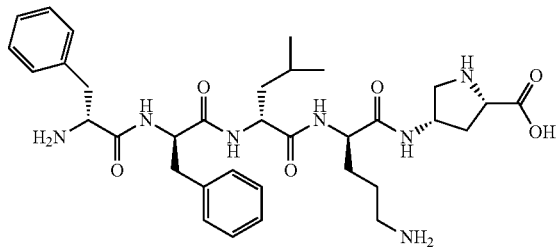

D-Phe-D-Phe-D-Leu-D-Orn-[(2S,4S)-4-amino-pyrrolidine-2-carboxylic acid]-OH

Compound (43)

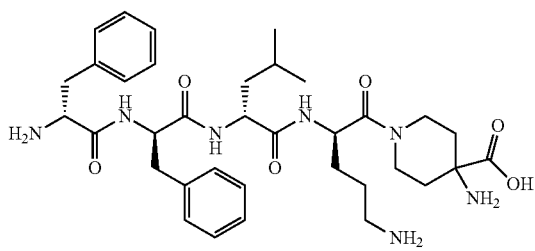

D-Phe-D-Phe-D-Leu-D-Orn-(ω(4-aminopiperidine-4-carboxylic acid)]-OH

Compound (44)

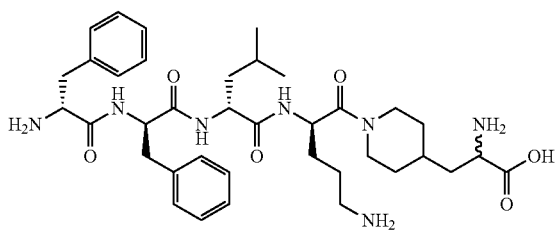

D-Phe-D-Phe-D-Leu-D-Orn-(ω(D/L-2-amino-3-(4-N-piperidinyl)propionic acid)]-OH

Compound (45)

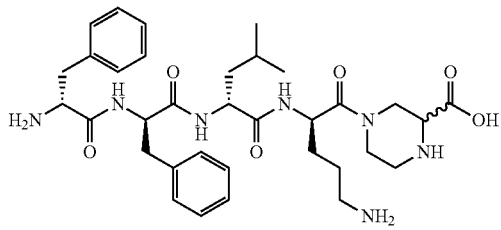

D-Phe-D-Phe-D-Leu-D-Orn-(ω(D/L-4-piperazine-2-carboxylic acid)]-OH

Compound (46)

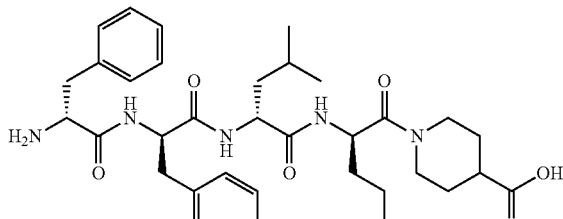

D-Phe-D-Phe-D-Leu-D-Orn-[Isonipecotic acid]-OH

Compound (47)

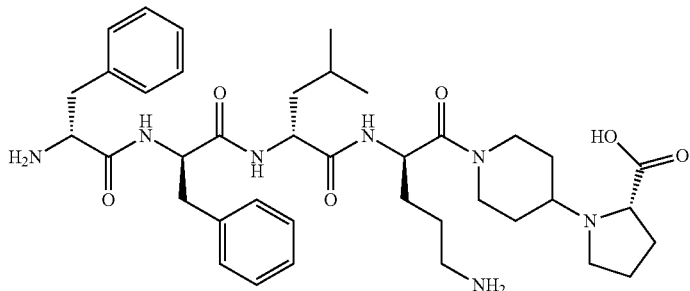

D-Phe-D-Phe-D-Leu-D-Orn-[N-(4-piperidinyl)-L-proline]-OH

Compound (48)
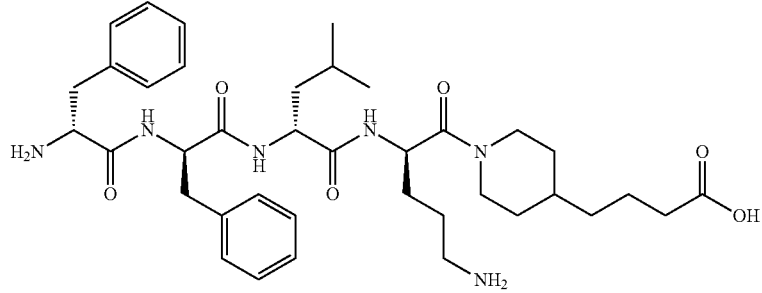
D-Phe-D-Phe-D-Leu-D-Orn-[4-(4-piperidinyl)-butanoic acid)]-OH
Compound (49)
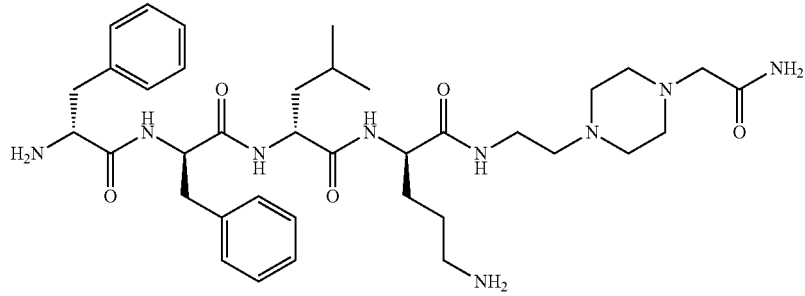
D-Phe-D-Phe-D-Leu-D-Orn-[4-(2-aminoethyl)-1-carboxymethyl-piperazine]-NH$_2$
Compound (50)
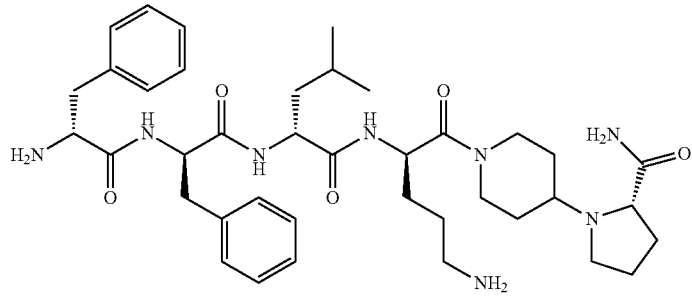
D-Phe-D-Phe-D-Leu-D-Orn-[N-(4-piperidinyl)-L-proline]-NH$_2$
Compound (51)
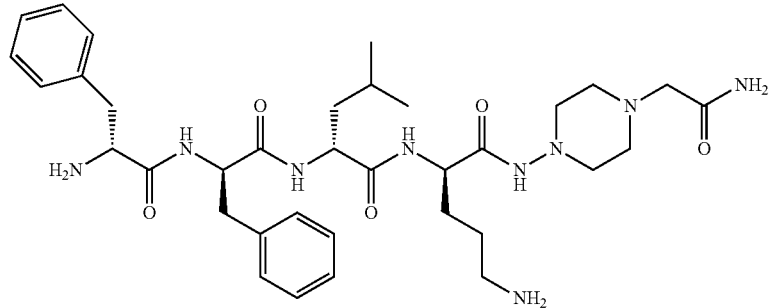
D-Phe-D-Phe-D-Leu-D-Orn-[4-(2-aminoethyl)-1-carboxymethyl-piperazine]-NH$_2$ Compound (52)

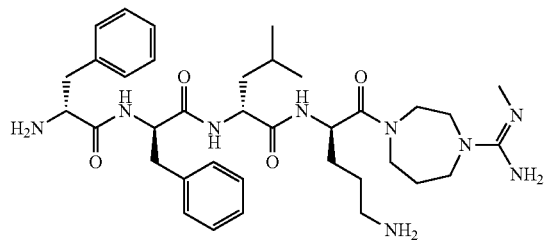

D-Phe-D-Phe-D-Leu-D-Orn-[4-(N-methyl)amidino-homopiperazine amide]

Compound (53)

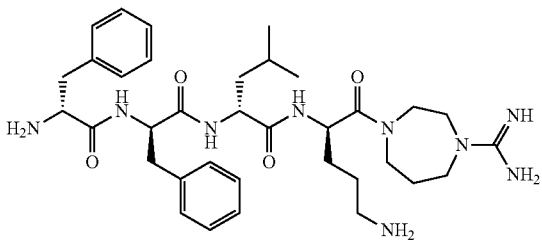

D-Phe-D-Phe-D-Leu-D-Orn-[4-amidinohomopiperazine amide]

Compound (54)

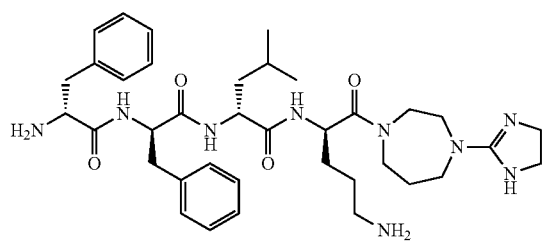

D-Phe-D-Phe-D-Leu-D-Orn-[4-(4,5-dihydro-1H-imidazol-2-yl)homopiperazine amide]

Compound (55)

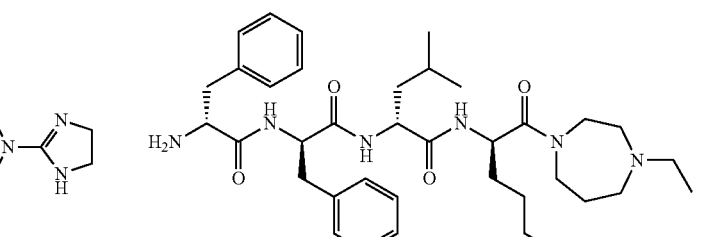

D-Phe-D-Phe-D-Leu-D-Orn-[4-ethylhomopiperazine amide]

Compound (56)

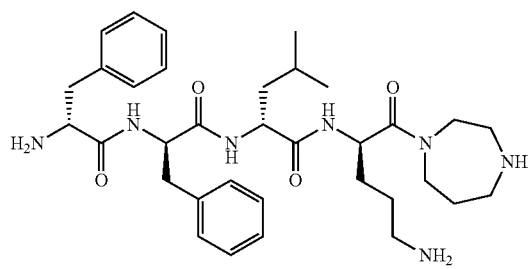

D-Phe-D-Phe-D-Leu-D-Orn-[homopiperazine amide]

Compound (57)

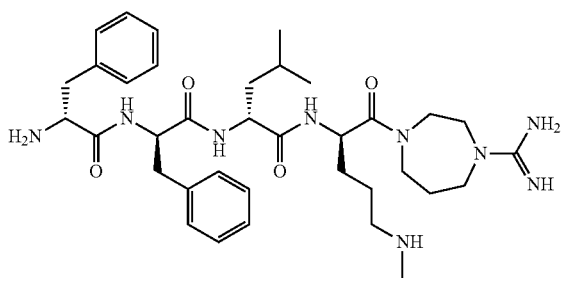

D-Phe-D-Phe-D-Leu-(δ-Me)D-Orn-[4-amidinohomopiperazine amide]

Compound (58)

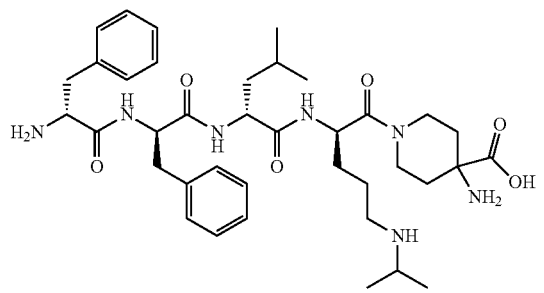

D-Phe-D-Phe-D-Leu-(δ-iPr)D-Orn-(ω(4-aminopiperidine-4-carboxylic acid)]-OH

Compound (59)

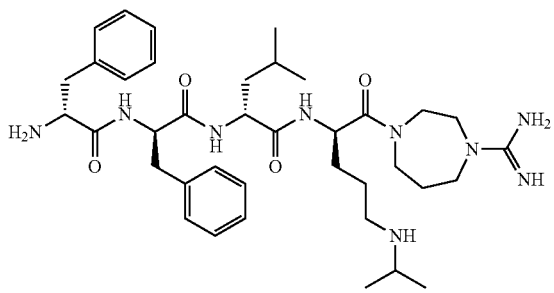

D-Phe-D-Phe-D-Leu-(δ-iPr)D-Orn-[4-amidinohomopriperazine amide]

-continued

Compound (60)

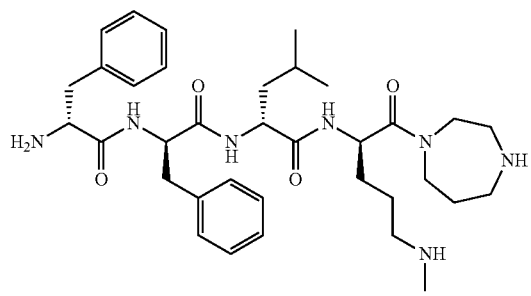

D-Phe-D-Phe-D-Leu-(δ-Me)D-Orn-[homopriperazine amide]

Compound (61)

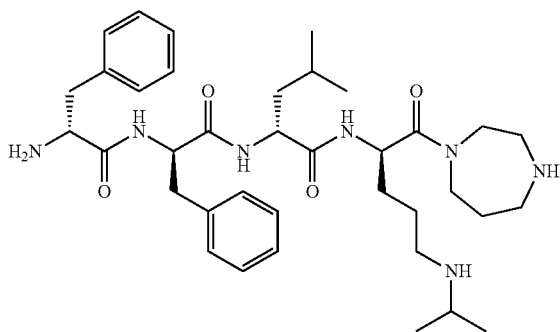

D-Phe-D-Phe-D-Leu-(δ-iPr)D-Orn-[homopriperazine amide]

Compound (62)

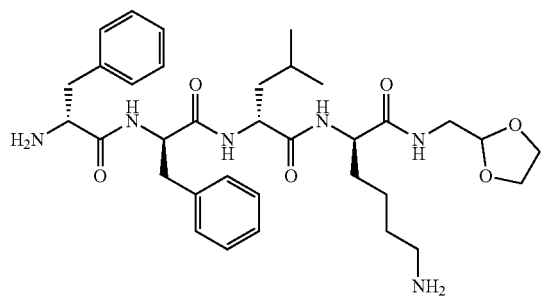

D-Phe-D-Phe-D-Leu-D-Lys-[1,3-dioxolan-2-yl)methanamine amide]

Compound (63)

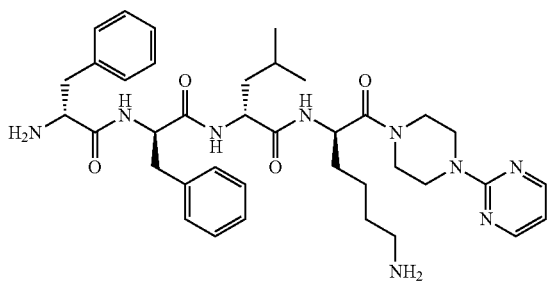

D-Phe-D-Phe-D-Leu-D-Lys-[2-(piperazin-1-yl)pyrimidine amide]

Compound (64)

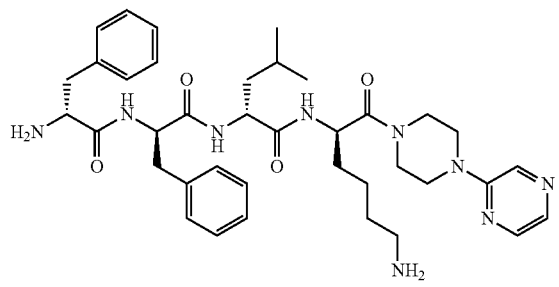

D-Phe-D-Phe-D-Leu-D-Lys-[2-(piperazin-1-yl)pyrazine amide]

Compound (65)

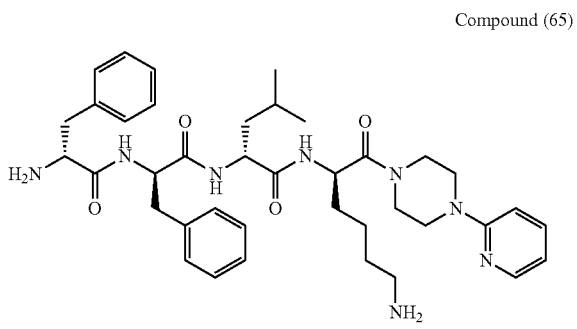

D-Phe-D-Phe-D-Leu-D-Lys-[2-(pyridin-2-yl)piperazine amide]

Compound (66)

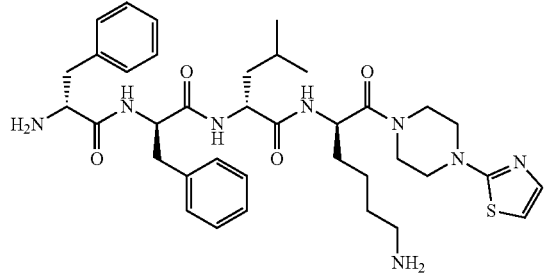

D-Phe-D-Phe-D-Leu-D-Lys-[2-(piperazin-1-yl)thiazole amide]

Compound (67)

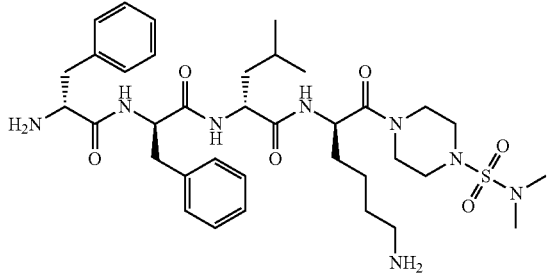

D-Phe-D-Phe-D-Leu-D-Lys-[N,N-dimethylpiperazine-1-sulfonamide amide]

Compound (68)

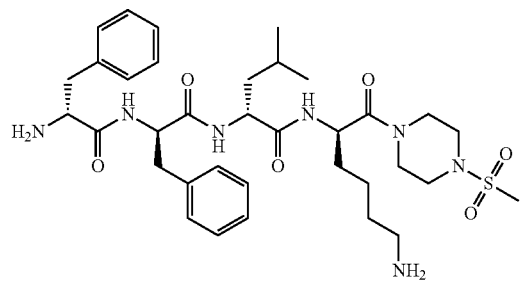

D-Phe-D-Phe-D-Leu-D-Lys-[1-(methylsulfonyl)piperazine amide]

Compound (69)

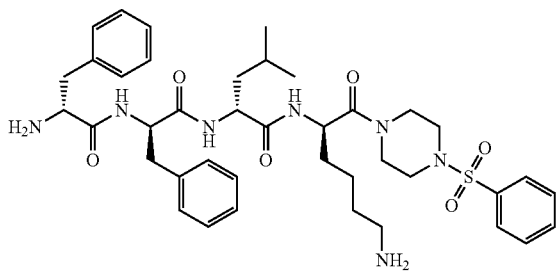

D-Phe-D-Phe-D-Leu-D-Lys-[1-(phenylsulgonyl)piperazine amide]

Compound (70)

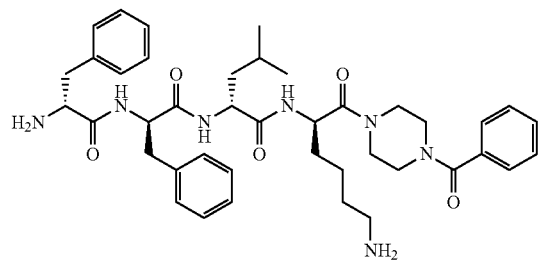

D-Phe-D-Phe-D-Leu-D-Lys-[phenyl(piperazin-1-yl)methanone amide]

Compound (71)

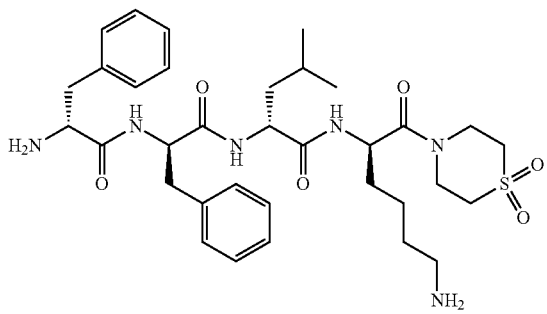

D-Phe-D-Phe-D-Leu-D-Lys-[thiolmorpholine-1,1-dioxide amide]

Compound (72)

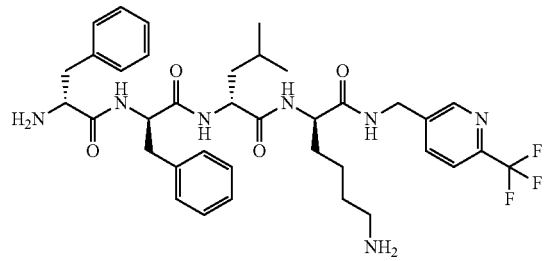

D-Phe-D-Phe-D-Leu-D-Lys-[6-trifluoromethyl-3-aminomethyl pyridine amide]

Compound (73)

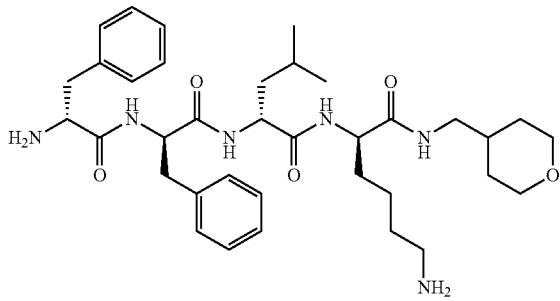

D-Phe-D-Phe-D-Leu-D-Lys-N-methyl-1-(tetrahydro-2H-pyran-4-yl)methanamine amide]

Compound (74)

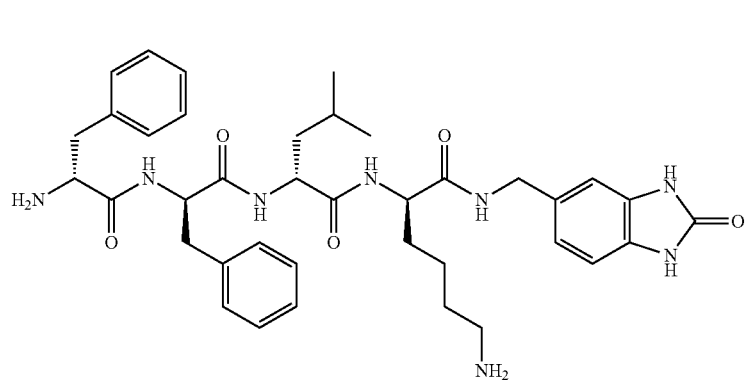

D-Phe-D-Phe-D-Leu-D-Lys-[5-(aminomethyl)-1H-benzo[d]imidazol-2(3H)-one amide]

Compound (75)
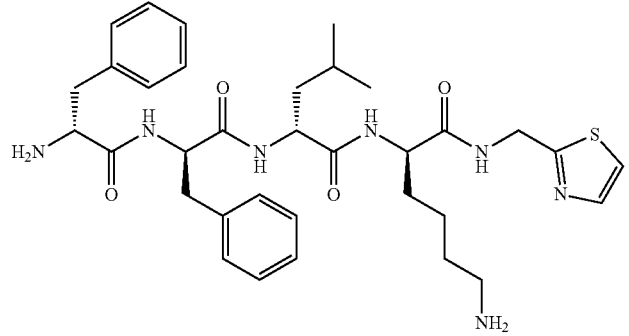
D-Phe-D-Phe-D-Leu-D-Lys-N-(thiazol-2-ylmethyl) amide
Compound (76)
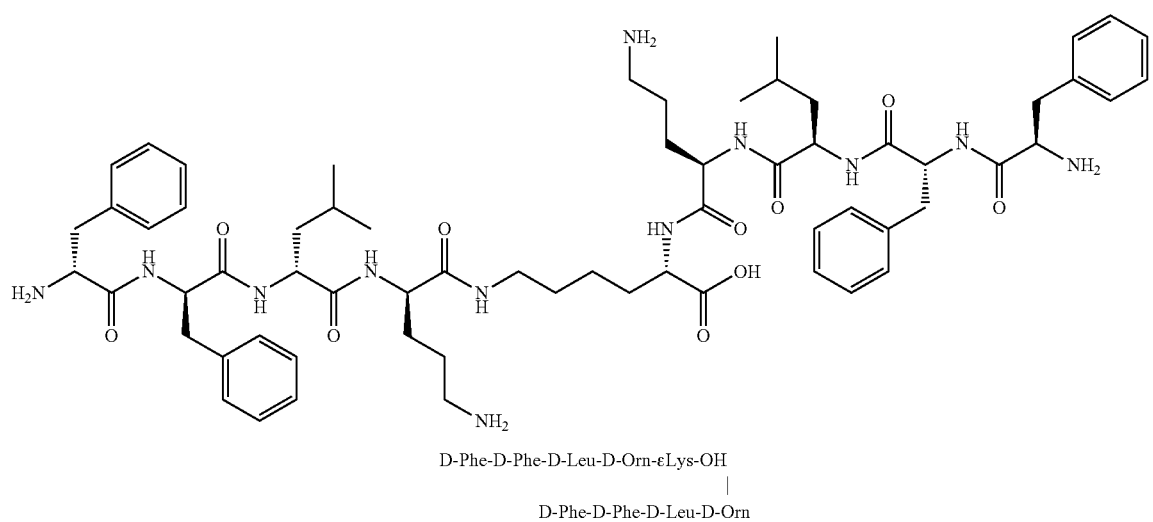
D-Phe-D-Phe-D-Leu-D-Orn-εLys-OH
|
D-Phe-D-Phe-D-Leu-D-Orn
Compound (77)
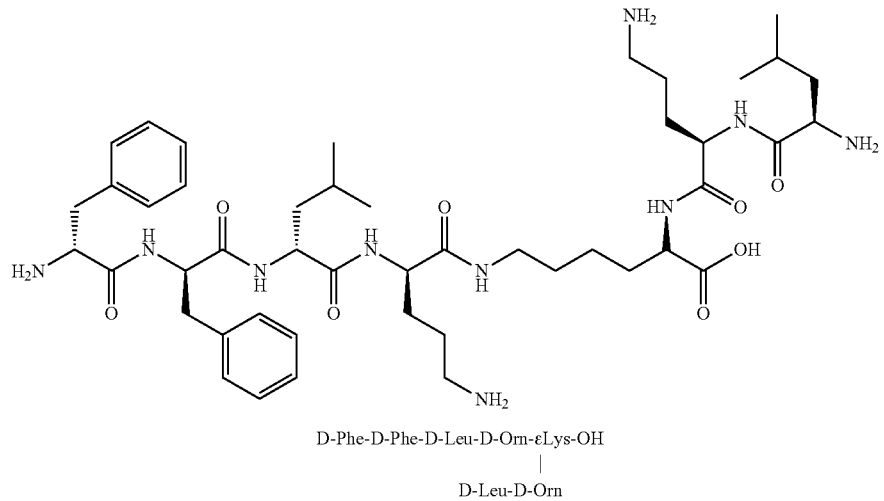
D-Phe-D-Phe-D-Leu-D-Orn-εLys-OH
|
D-Leu-D-Orn -continued
Compound (78)
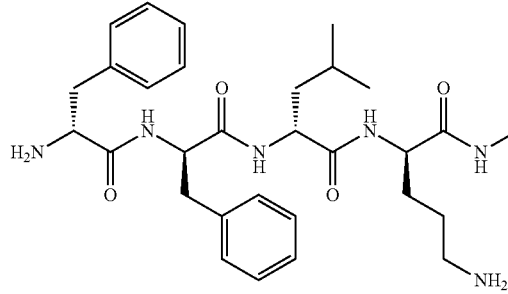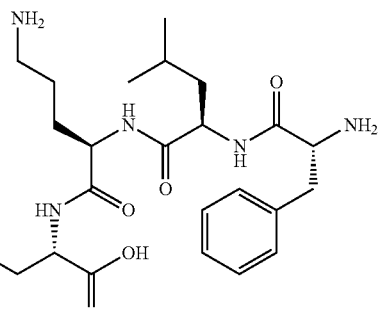
D-Phe-D-Phe-D-Leu-D-Orn-εLys-OH
|
D-Phe-D-Leu-D-Orn
Compound (79)
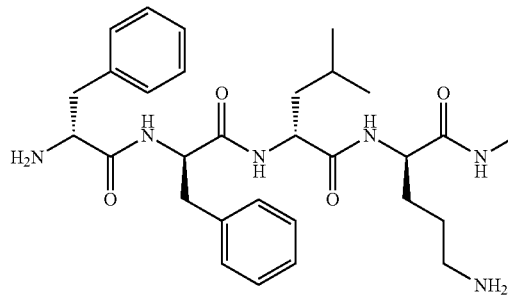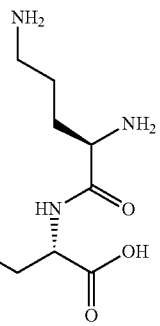
D-Phe-D-Phe-D-Leu-D-Orn-εLys-OH
|
D-Orn
Compound (80)
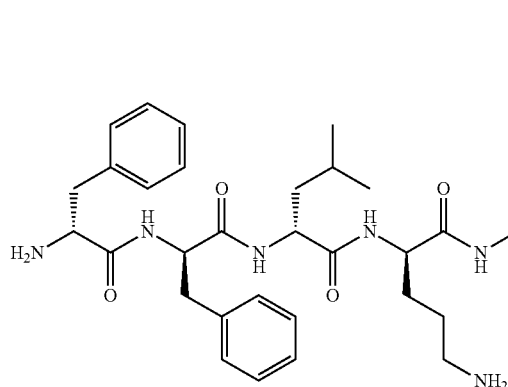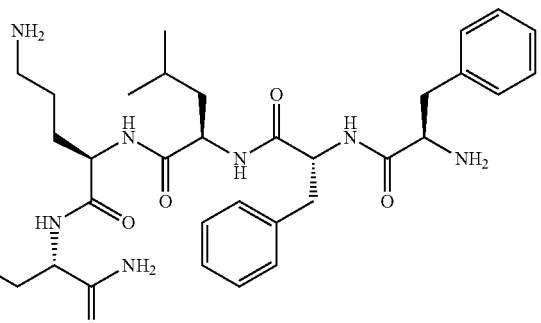
D-Phe-D-Phe-D-Leu-D-Orn-εLys-NH$_2$
|
D-Phe-D-Phe-D-Leu-D-Orn Compound (81)
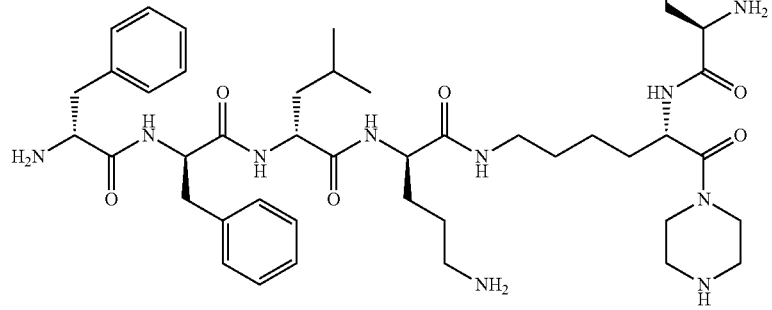
D-Phe-D-Phe-D-Leu-D-Orn-εLys-N(-CH₂CH₂-NH-CH₂CH₂-)
|
D-Orn
Compound (82)
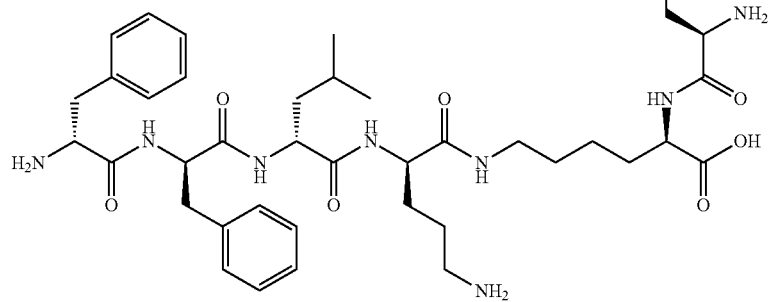
D-Phe-D-Phe-D-Leu-D-Orn-εLys-OH
|
D-Orn
Compound (83)
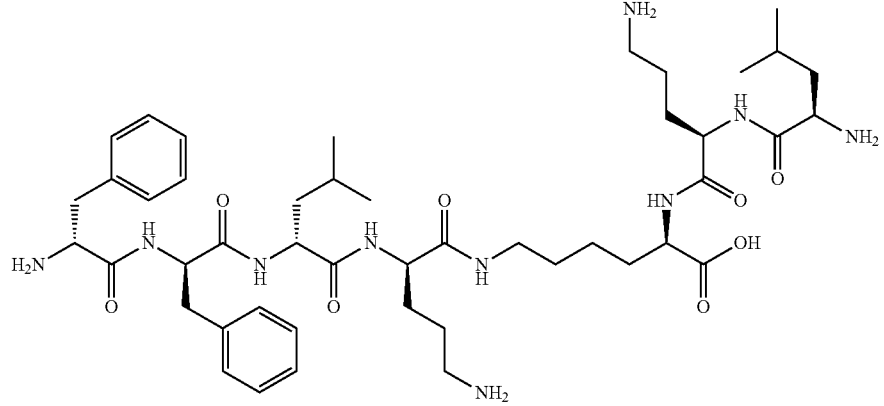
D-Phe-D-Phe-D-Leu-D-Orn-εLys-OH
|
D-Leu-D-Orn Compound (84)
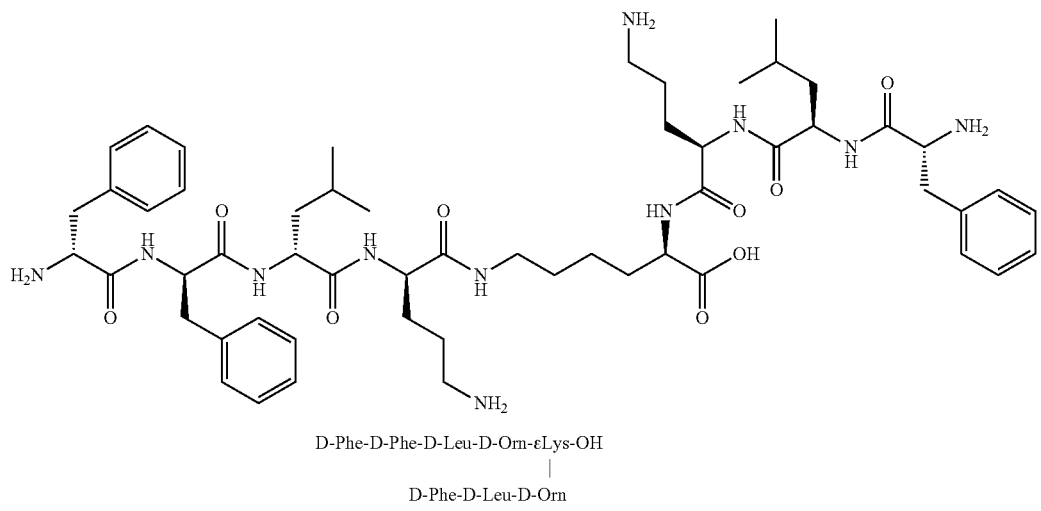
D-Phe-D-Phe-D-Leu-D-Orn-εLys-OH
|
D-Phe-D-Leu-D-Orn
Compound (85)
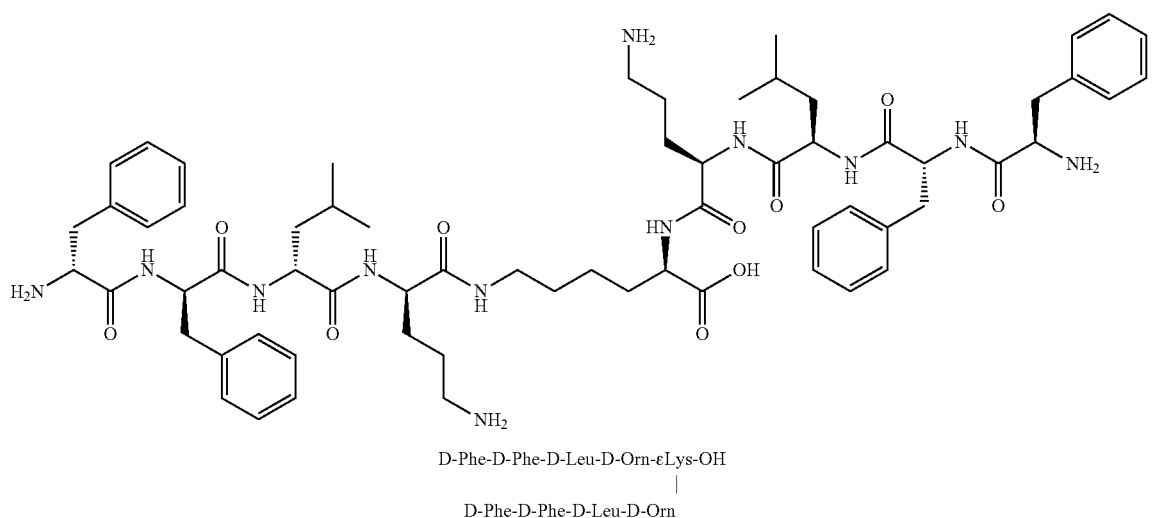
D-Phe-D-Phe-D-Leu-D-Orn-εLys-OH
|
D-Phe-D-Phe-D-Leu-D-Orn
Compound (86)
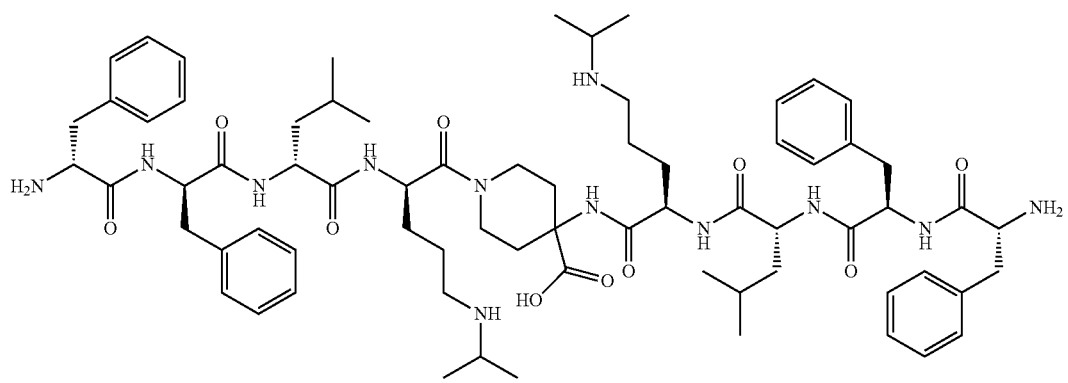
1N,4N-bis-[D-Phe-D-Phe-D-Leu-(iPr)D-Orn]-4-amino-4-carboxylic-piperidine Compound (87)
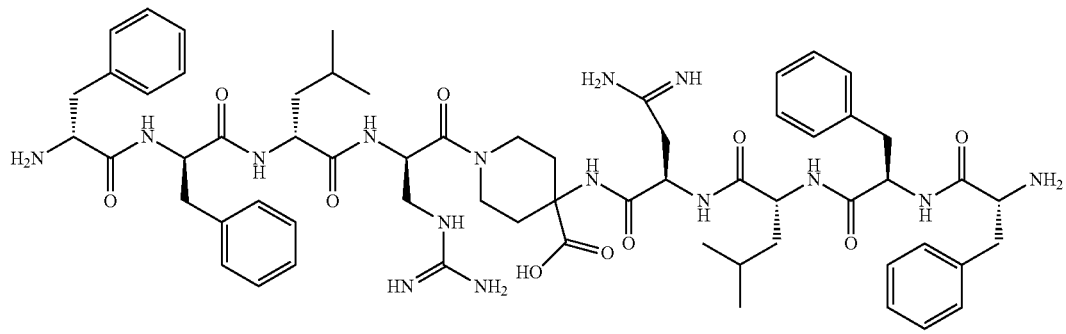
1N,4N-bis-[D-Phe-D-Phe-D-Leu-D-Dap(amidino)]-4-amino-4-carboxylic-piperidine
Compound (88)
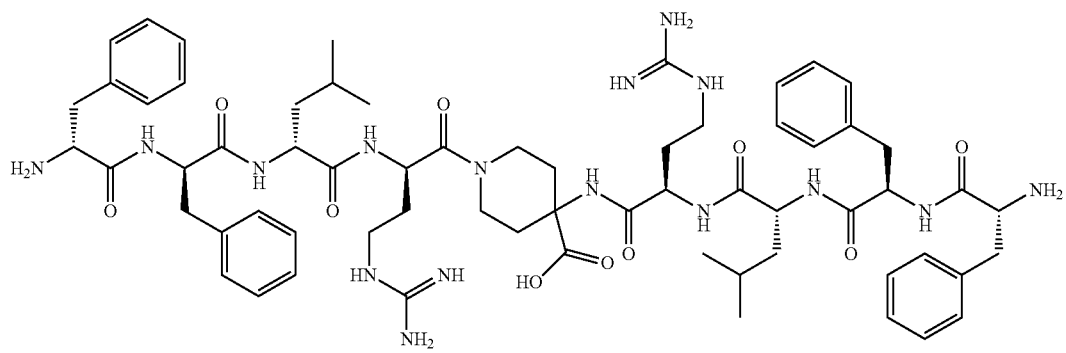
1N,4N-bis-(D-Phe-D-Phe-D-Leu-D-Nar)-4-amino-4-carboxylic-piperidine
Compound (89)
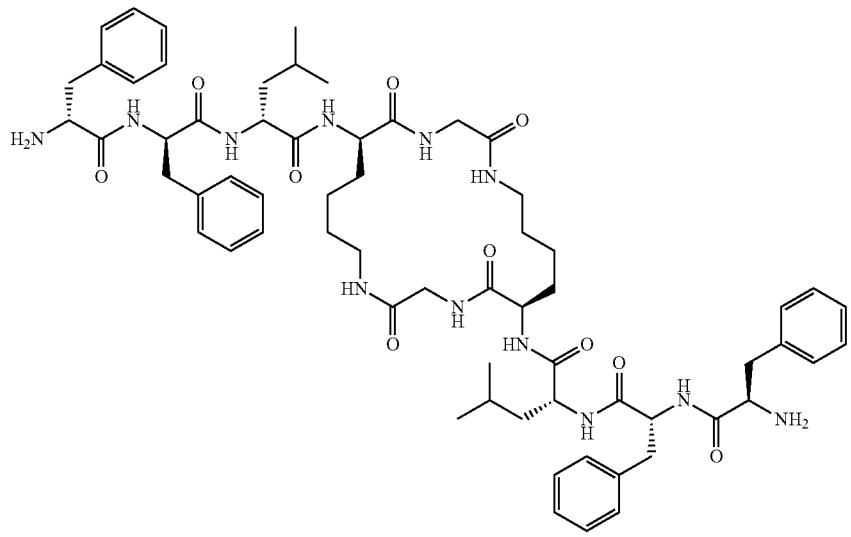
D-Phe-D-Phe-D-Leu-bis(D-Lys-Gly)Lactam
|
D-Phe-D-Phe-D-Leu Compound (90)

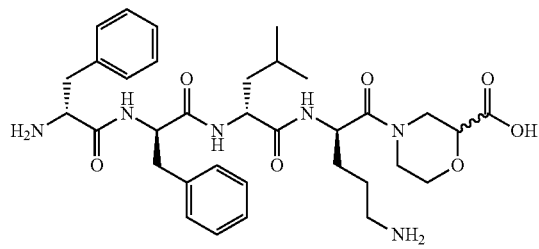

D-Phe-D-Phe-D-Leu-D-Orn-[R/S-2-carboxymorpholine]-OH

Compound (91)

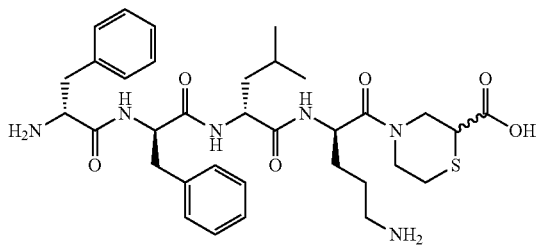

D-Phe-D-Phe-D-Leu-D-Orn-[R/S-2-carboxythiomorpholine]-OH

Compound (92)

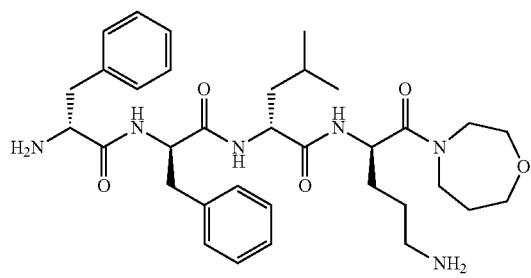

D-Phe-D-Phe-D-Leu-D-Orn-N(homomorpholine)

Compound (93)

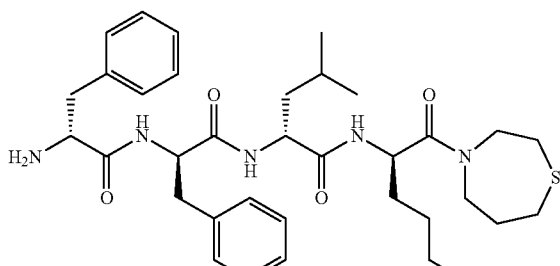

D-Phe-D-Phe-D-Leu-D-Orn-N(homothiomorpholine)

Compound (94)

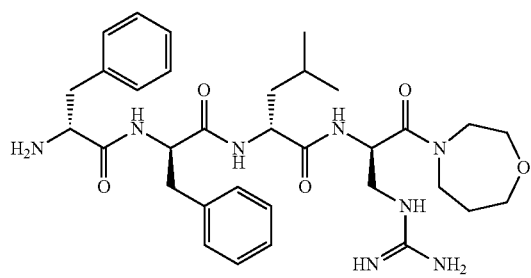

D-Phe-D-Phe-D-Leu-D-Dap(amidio)-[homomorpholine amide]

Compound (95)

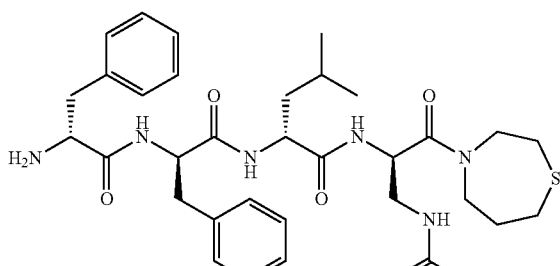

D-Phe-D-Phe-D-Leu-D-Dap(amidino)-[homothiomorpholine amide]

Compound (96)

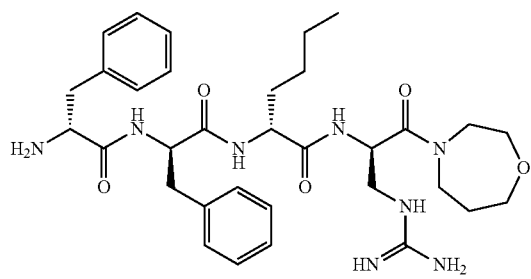

D-Phe-D-Phe-D-Nle-D-Dap(amidio)-[homomorpholine amide]

Compound (97)

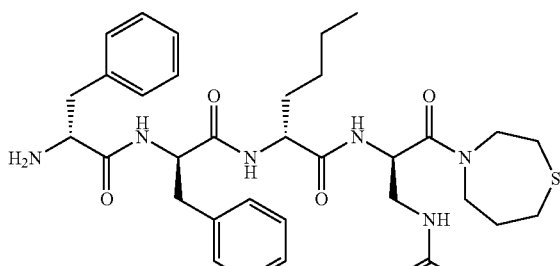

D-Phe-D-Phe-D-Nle-D-Dap(amidino)-[homothiomorpholine amide]

-continued

Compound (98)

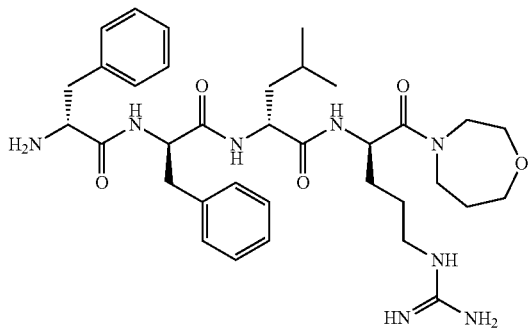

D-Phe-D-Phe-D-Leu-D-Arg-[homomorpholine amide]

Compound (99)

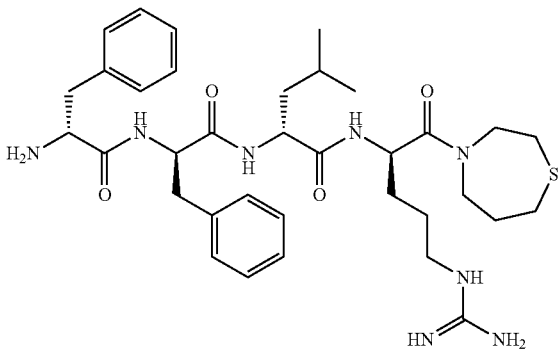

D-Phe-D-Phe-D-Leu-D-Arg-[homothiomorpholine amide]

Compound (100)

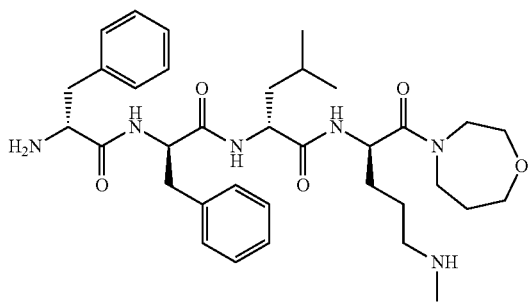

D-Phe-D-Phe-D-Leu-D-Orn(Me)-[homomorpholine amide]

Compound (101)

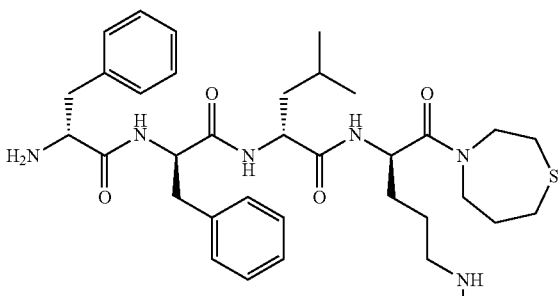

D-Phe-D-Phe-D-Leu-D-Orn(Me)-[homothiomorpholine amide]

Compound (102)

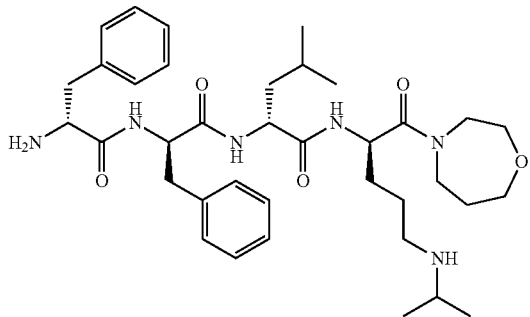

D-Phe-D-Phe-D-Leu-D-Orn(iPr)-[homomorpholine amide]

Compound (103)

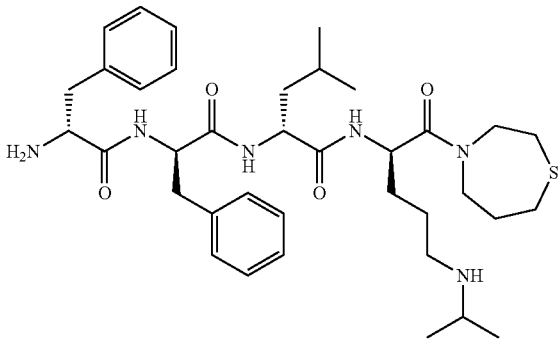

D-Phe-D-Phe-D-Leu-D-Orn(iPr)-[homothiomorpholine amide]

Compound (104)

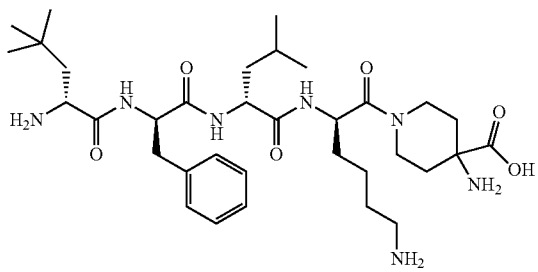

β-tert-Bu-D-Ala-D-Phe-D-Leu-D-Lys-[ω(4-aminopiperidine-4-carboxylic acid)]-OH

Compound (105)

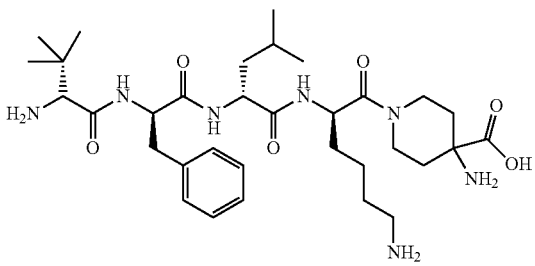

D-tert-Leu-D-Phe-D-Leu-D-Lys-[ω(4-aminopiperidine-4-carboxylic acid)]-OH

Examples 1-105

Synthesis of compounds (1)-(105) has been described: See U.S. Pat. Nos. 7,402,564 and 7,713,937 the entire disclosures of which are incorporated by reference herein.

Example 106: Production of Enterically Coated Size 2 Hydroxypropylmethyl Cellulose (HPMC) Capsules Containing 5 mg CR845 Suspended in 1 g 10% Capric Acid in Miglyol® Solution Miglyol® 812N (44.750 g) was added in a 50 ml glass beaker. Then 5.00 g capric acid was weighed and added to the Miglyol® while stirring on a magnetic stir plate with a 0.5 inch stir bar. The mixture was continuously stirred at a gentle speed. 0.25 g CR845 was weighed (adjusted for peptide content) and added to the Capric Acid/Miglyol® solution while mixing to produce a uniformly dispersed suspension. Mixing was maintained at 500 rpm throughout the capsule filling process performed as follows:

A size "2" capsule plate was set up according to the ProCoater Capsule Filler (Torpac Inc, Fairfield, N.J.) instruction manual with empty capsule bodies. Using a positive displacement pipette, 0.32 mL of the suspension was dispensed into each capsule body in the plate. Individually the opened end of each capsule cap was wetted with 90% Ethanol and snapped on each of the filled capsule bodies in the coating plate. The coating plate with the capsules (cap up) was placed in the Drying Stand and allowed to stand for a minimum of 60 minutes.

Preparation of Enteric Coating Solution

Acetone NF (888 mL) was measured, poured into a 1 L beaker and stirring initiated. Once a gentile vortex was achieved 120 g Eudragit® L100-55 was added to the acetone while mixing. 12 g Triethyl citrate USP was then added to the acetone/Eudragit® L100-55 followed by addition of 19.2 g water USP to the Acetone/Eudragit® L100-55/Triethyl Citrate while continuously stirring until the solution was clear. The solution was then transferred into a 1 L serum bottle and capped.

Application of Enteric Coating Material

Coating solution (200 g) was transferred into the ProCoater Capsule Filler coating pan and the bodies of the filled capsules were dipped in the plate in the coating solution, remove and rotate according to the instructions in the manufacturer's manual. The plate with the coated capsules was placed in the ProCoater Capsule Filler Drying Stand and allowed to dry for a minimum of 25 minutes. The capsule holder was adjusted to expose the capsule caps according to ProCoater manual directions. The cap of each of the capsules was dipped in each plate in the coating solution, removed and rotated as per the manufacturer's instructions. The plate with the coated capsules was then placed in the ProCoater Capsule Filler Drying Stand and dry for a minimum of 25 minutes. Additional coating solution was then added to the coating pan to maintain appropriate volume and the above steps were repeated to recoat the capsules.

The middle 32 capsules of each plate were transferred into an HDPE bottle (75 mL) labeled with Lot #, date, initials, and number of capsules for PK studies. The outside 28 capsules of each plate were transferred into the HDPE bottle (75 mL) labeled with Lot #, date, initials, and number of capsules and marked "For research stability use only."

Example 107: Production of Enterically Coated Size 2 HPMC Capsules Containing 5 mg CR845 suspended in 1 g 30% Capric Acid in Miglyol® Solution Miglyol® (34.75 g) and capric acid (15.0 g) were added to a 50 ml glass beaker while stirring until a clear solution is obtained. CR845 (0.25 g) was added to the capric acid/Miglyol® solution while mixing produce a uniformly dispersed suspension. Capsule plate set up, capsule filling with the 5 mg CR845 suspended in 1 g 30% capric acid/ Miglyol® Solution and application of the enteric coating material were performed as described above.

Example 108: Oral Administration of Dosing Formulations in Canines

The test formulation was delivered orally within a capsule in a single dose. Capsules were lubricated with reverse osmosis water immediately prior to administration. Animals were gently stroked along the neck to stimulate the swallowing reflex after dosing. Immediately after dosing, 5-10 mL of reverse osmosis water was administered to the animal. The oral cavity was inspected following the water flush to ensure that the capsule had been swallowed.

Example 109: Pharmacokinetic Data from Oral Administration of Dosing Formulations in Canines FIG. 1 shows CR845.HCl acid salt bioavailability measured in cohorts of eight animals for each of the formulations delivered in enterically-coated size 2 HPMC capsules prepared as described above. Each capsule of prototype formulation 1 contained: 1.6 mg spray dried CR845 in 90% Miglyol 812, 10% sodium caprate. Each capsule of prototype formulation 2 contained: 1.6 mg crystallized CR845 in 90% Miglyol 812, 10% sodium caprate. Each capsule of prototype formulation 3 contained: 1.6 mg spray dried CR845 in 90% Miglyol 812, 10% capric acid. Each capsule of prototype formulation 4 contained: 1.6 mg spray dried CR845 in 70% Miglyol 812 in 30% capric acid. Bioavailability (% f) is expressed as a percent of CR845 observed (calculated from the area under the curve: AUC) as compared with the total CR845 AUC observed after intravenous delivery of the same dose. Composite IV data from five separate studies with thirty-six canines was averaged and used for bioavailability calculations. Ten kilogram dogs were dosed administered an average dose of 0.029±0.007 mg/kg and the average bioavailability was set as 100%. The observed avg. Cmax was 163.1±39.2 for comparison purposes.

Bioavailability of CR845 as shown used herein are calculated as follows:

$$\% f = \frac{(AUC\ \text{oral}/\text{Dose oral})}{(AUC\ iv/\text{Dose}\ iv)} \times 100$$

Example 110: Prototype Formulation Dissolution Profiles

FIGS. 2-5 and Table 1 below show the results of capsule dissolution studies of capsules containing prototype formulations 1-4 carried out according to US Pharmacopeia for Delayed Release Dosage Forms (USP <711>).

TABLE 1

| Prototype | T for 50% dissolution in Buffer Phase (min) |
|---|---|
| Formulation 1 | 28.0 |
| Formulation 2 | 44.1 |
| Formulation 3 | 31.8 |
| Formulation 4 | 27.9 |

Example 111: Bioactivity of Trehalose-Embedded CR845 Salt Prototype Formulations Spray dried particles of CR845 acetate/trehalose/citric acid (9.8/88.2/2.2% w/w) and CR845.HCl/trehalose (23/77% w/w) were filled into intrinsically enteric (acid resistant) HPMC capsules and administered to cohorts of eight canines. Citric acid added to the acetate salt was to balance the pH. Average bioavailability for each formulation was determined as described above and shown in Table 2 below:

TABLE 2

| Formulation | % f | SEM |
|---|---|---|
| CR845 acetate/trehalose/citric acid | 4.49 | 3.23 |
| CR845.HCl/trehalose | 9.40 | 6.75 |

Example 112: Bioactivity of Spray Dried Trehalose Embedded CR845.HCl Formulations Formulations 5, 6 and 7 in Size 1 LiCap (Capsugel) enterically coated capsules were each administered to a cohort of eight 8 kg canines. Formulation 5 contained 4.0 mg CR845.HCl, 20% capric acid in Miglyol® 812N; formulation 6 contained 4.0 mg CR845.HCl, 10% capric acid in Miglyol® 812N; formulation 7 contained 4.0 mg CR845.HCl, 5% capric acid in Miglyol® 812N.

Figure 6:
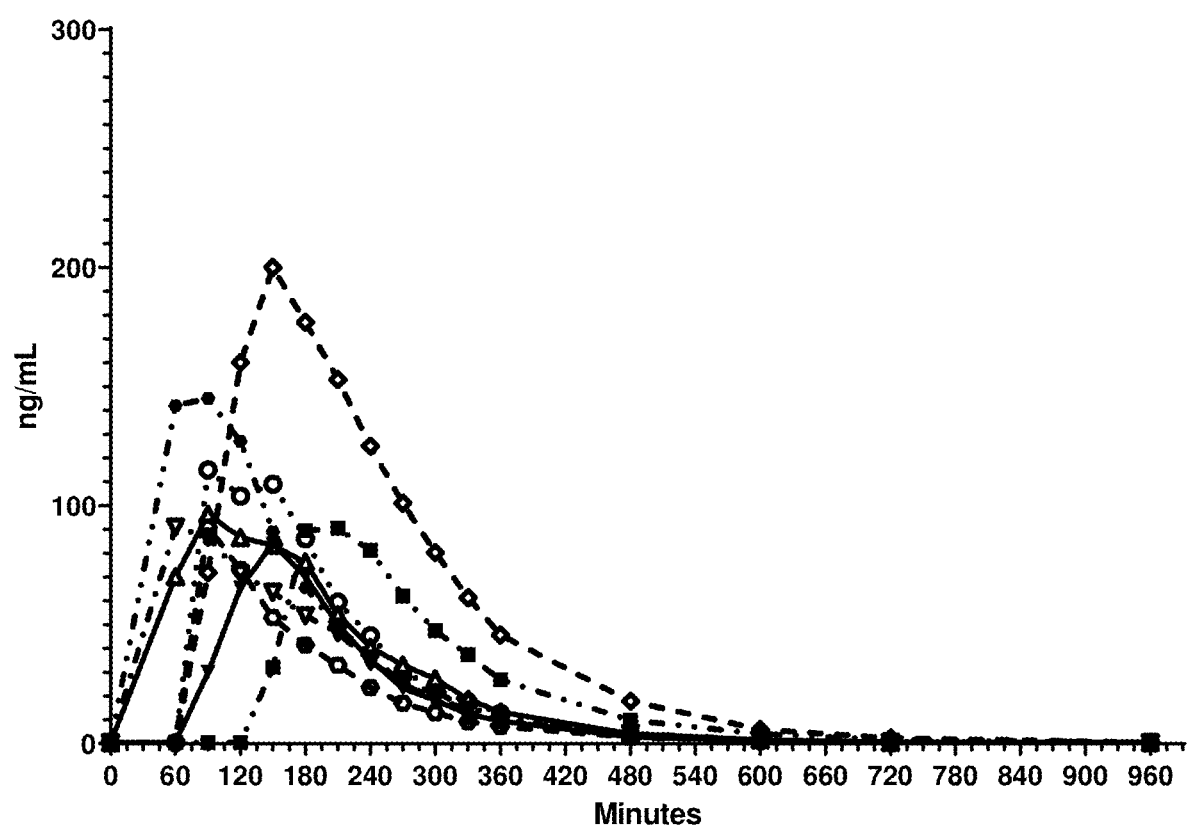
FIG. 6: Plasma concentration profile of formulation 5 containing 4.0 mg CR845.HCl, 20% capric acid in Miglyol® 812.
Figure 7:
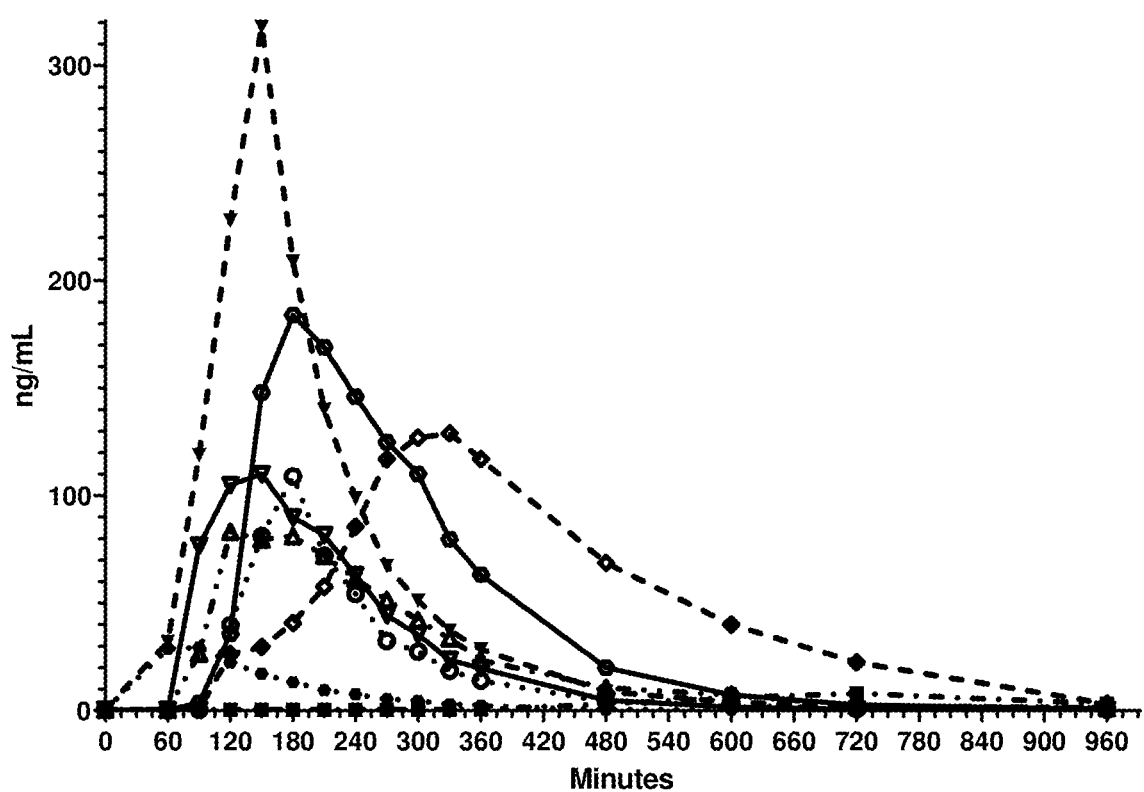
FIG. 7: Plasma concentration profile of formulation 6 containing 4.0 mg CR845.HCl, 10% capric acid in Miglyol® 812.
Figure 8:
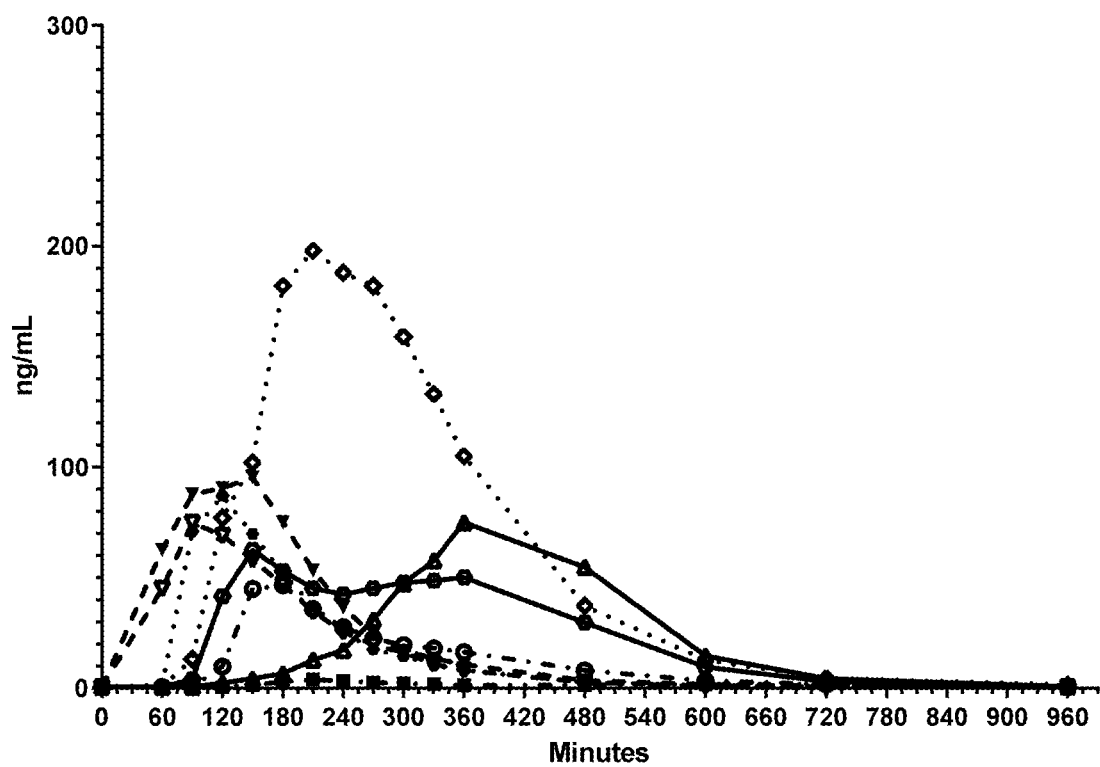
FIG. 8: Plasma concentration profile of formulation 7 containing 4.0 mg CR854, 5% capric acid in Miglyol® 812.

FIGS. 6-8 show PK profiles for formulations 5-7 and average bioavailability data were calculated from these curves and shown in Table 3 below:

TABLE 3

| Formulation | % f | Std. Dev. | SEM |
|---|---|---|---|
| 5 | 12.6 | 5.79 | 2.05 |
| 6 | 13.8 | 9.49 | 3.36 |
| 7 | 11.1 | 9.37 | 3.31 |

Further studies were performed with CR845.HCl/trehalose formulations.

Example 113: Stability of Prototype Formulations Suspended in Miglyol or Capric Acid In a first sample study 2.5 mg spray dried particles of CR845 embedded in trehalose were suspended in 1 gm Miglyol® (A) or 10% capric acid in Miglyol® (B). In another sample study, 2.5 mg spray dried particles of CR845 embedded in trehalose/Na caprate/EDTA were suspended in 1 gm Miglyol® (C) or 10% capric acid in Miglyol® (D). Suspensions prepared at room temperature were assayed for CR845 content and purity. The suspensions were then stored at 40° C., 75% rel. humidity and assayed again at two month and three months to assess stability.

Results are shown in Table 4 below:

TABLE 4

| Suspension Composition | | Initial (RT) | | 2 months (40° C./75% RH) | | 3 months (40° C./75% RH) | |
|---|---|---|---|---|---|---|---|
| | Capric acid (%) | Conc. (mg/g) | Content (mg) | Purity (%) | Content (mg) | Purity (%) | Content (mg) | Purity (%) |
| A | 0 | 2.47 | 2.43 | 98.10 | 2.67 | 98.64 | 2.65 | 98.73 |
| B | 10 | 2.47 | 2.61 | 98.42 | 2.64 | 99.00 | 2.80 | 98.47 |
| C | 0 | 2.46 | 1.98 | 98.24 | 2.07 | 98.70 | 2.03 | 98.50 |
| D | 10 | 2.46 | 2.22 | 98.10 | 2.06 | 97.50 | 2.04 | 96.13 |

Essentially no loss of CR845 content or purity assayed by HPLC was seen after two or three months storage at 40° C./75% RH. The CR845/trehalose/Na caprate particles suspended in Miglyol® did not settle after two months under these conditions. Suspensions were also very stable and although settling occurred during storage in other suspensions, the particles readily resuspended upon inversion.

Figure 9:
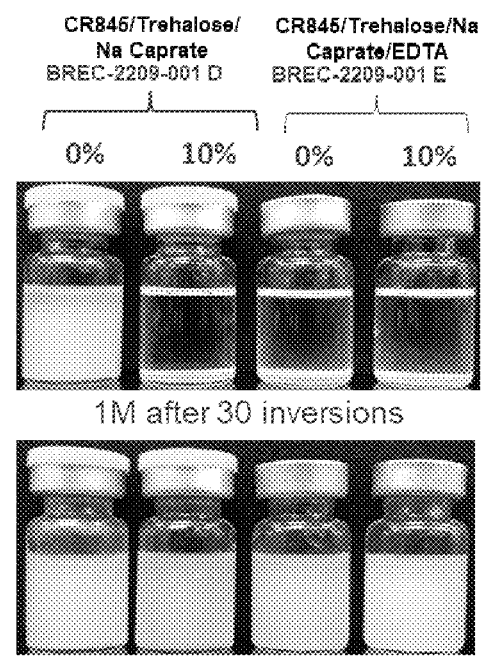
FIG. 9: Suspensions of CR845.HCl with 0% or 10% sodium caprate; or 0% or 10% sodium caprate plus EDTA after standing and 30 inversions after 1 month storage at 40° C. Photomicrographs show consistent particle size after 1 month or 2 months storage at 40° C.
Figure 9:
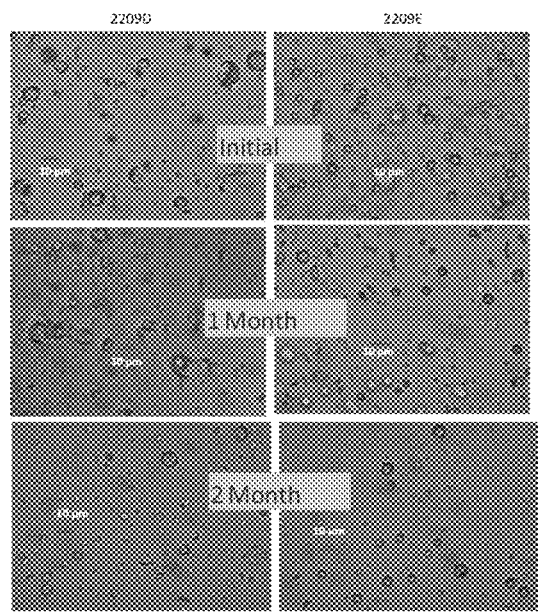
Figure 10:
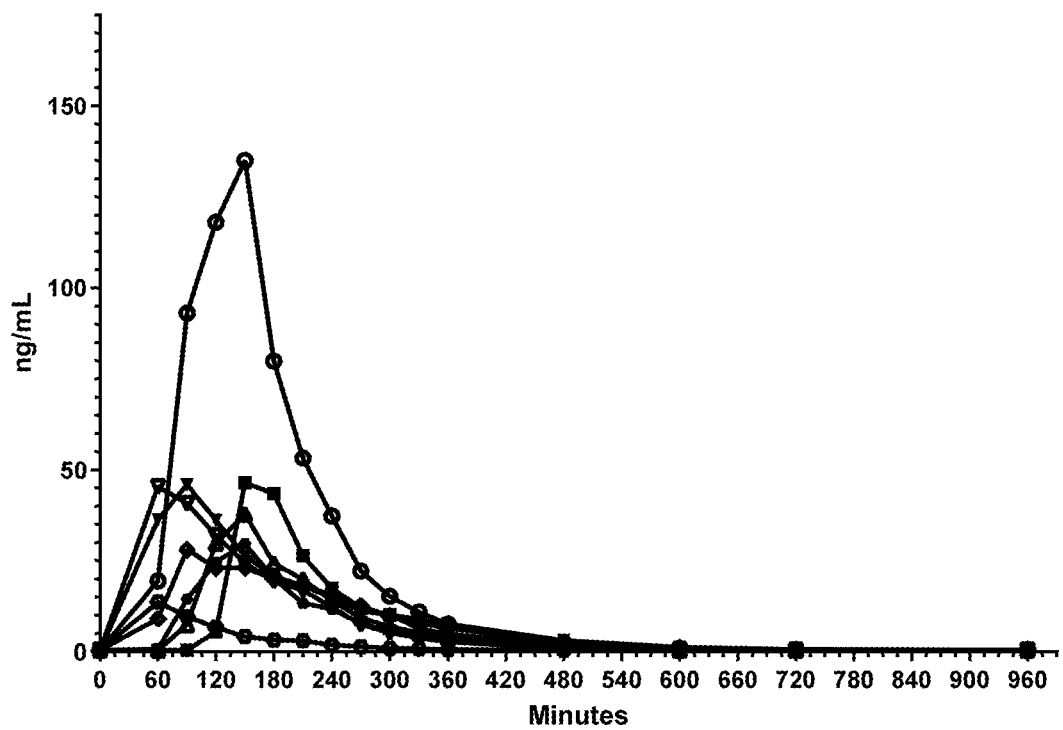
FIG. 10: Plasma concentration profile of formulation 8 containing 2.0 mg spray dried CR845.HCl (21% w/w), trehalose (70% w/w), 9% (w/w) EDTA, suspended in 10% capric acid in Miglyol® 812.
Figure 11:
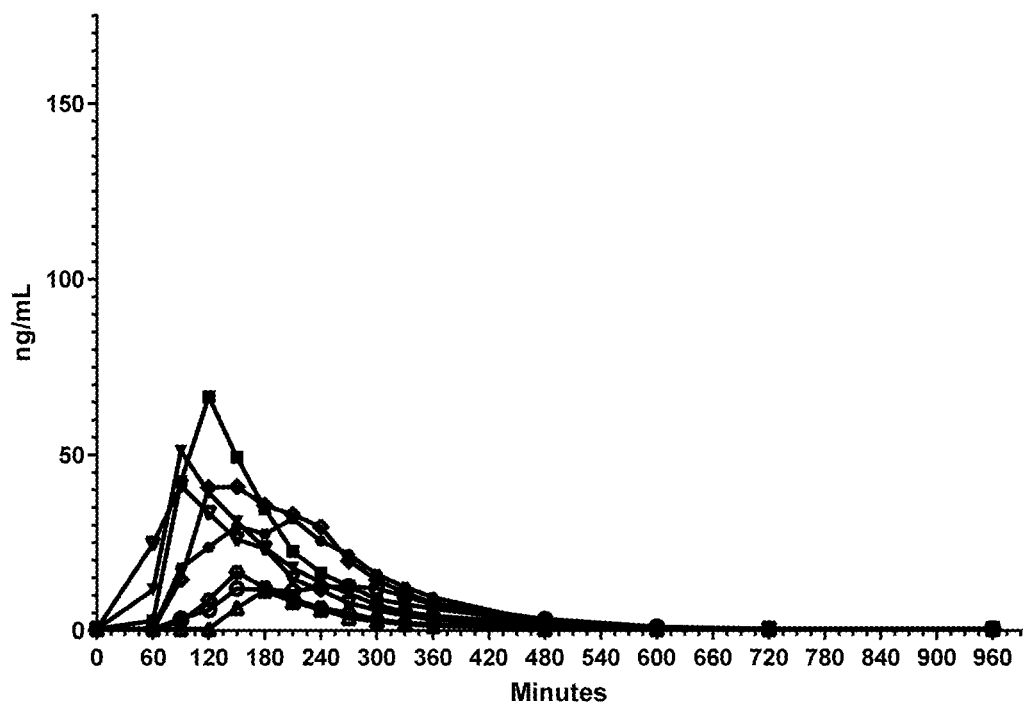
FIG. 11: Plasma concentration profile of formulation 9 containing 2.0 mg spray dried CR845.HCl (19% w/w), trehalose (62% w/w), sodium caprate (14% w/w), EDTA (5% w/w), in Miglyol® 812.
Figure 12:
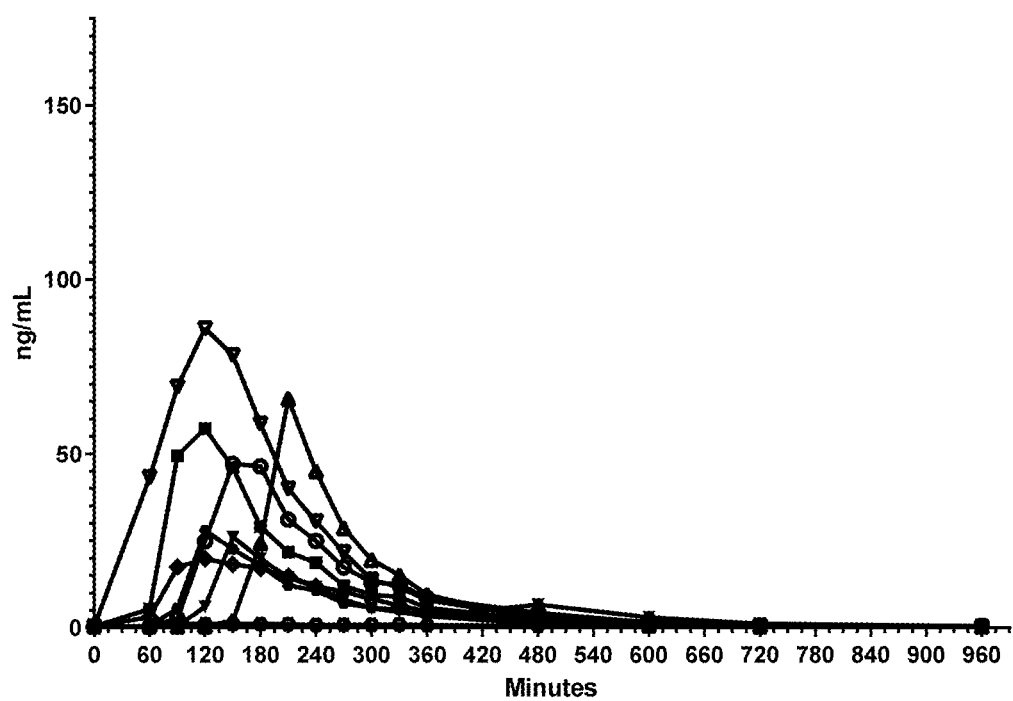
FIG. 12: Plasma concentration profile of formulation 10 containing 2.0 mg spray dried CR845.HCl (18% w/w), trehalose (60% w/w), sodium caprate (13% w/w), EDTA (9% w/w), in Miglyol® 812.
Figure 13:
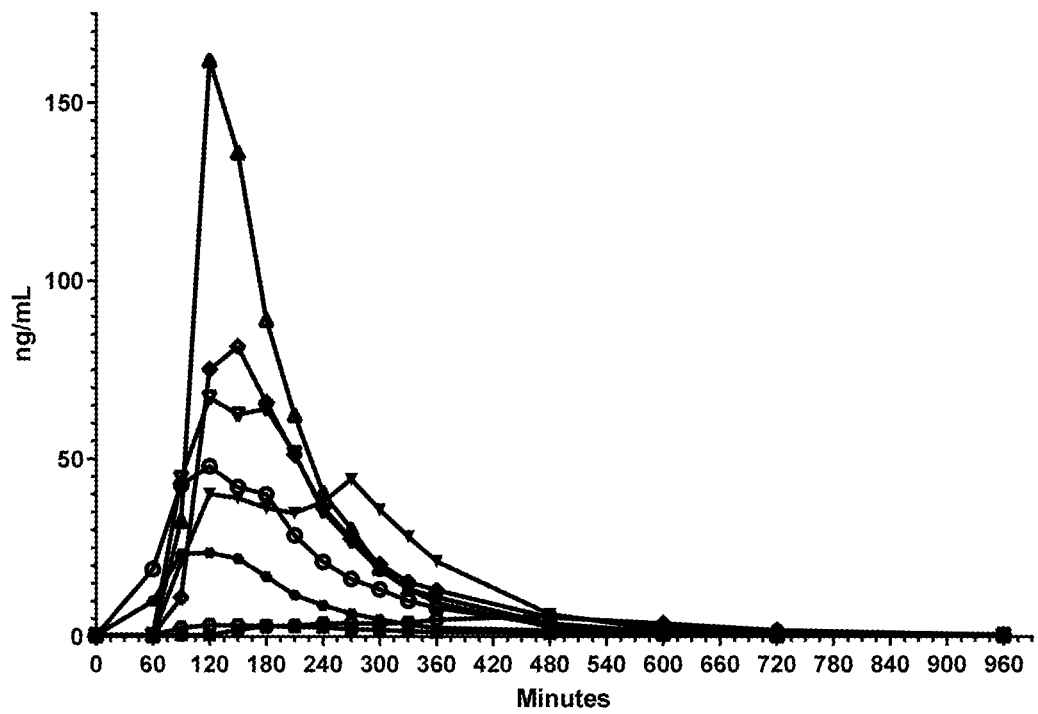
FIG. 13: Plasma concentration profile of formulation 11 containing 2.0 mg spray dried CR845.HCl (18% w/w), trehalose (60% w/w), sodium caprate (22% w/w), in Miglyol® 812.
Figure 14:
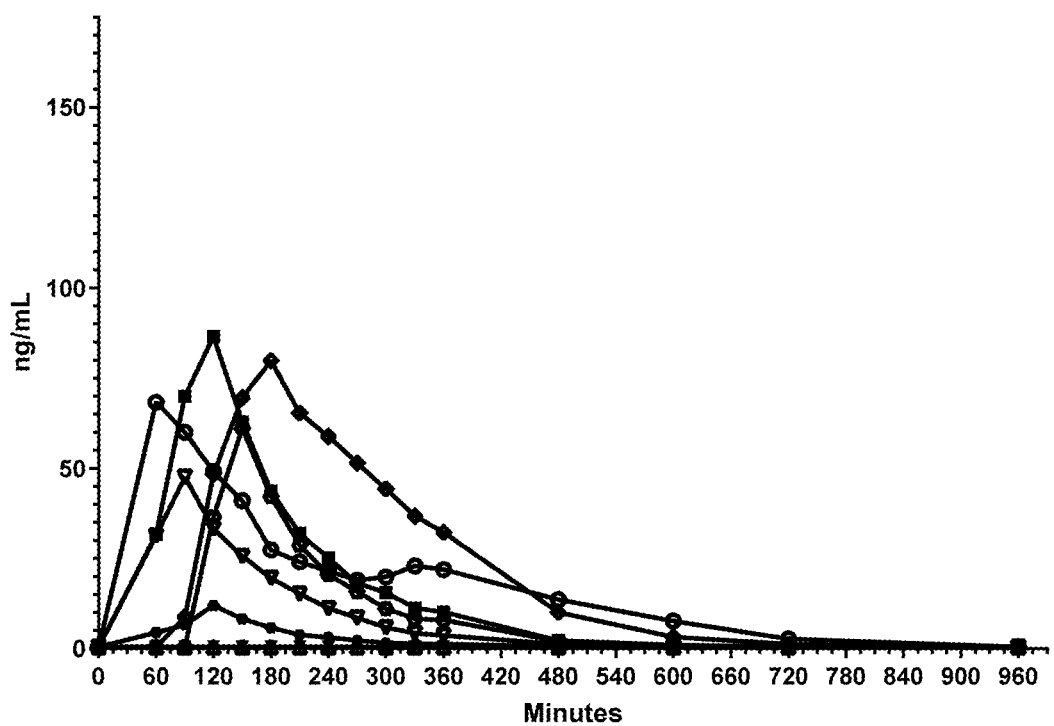
FIG. 14: Plasma concentration profile of formulation 12 containing 2.0 mg spray dried CR845.HCl (23% w/w), trehalose (77% w/w), suspended in 10% capric acid, Miglyol® 812.

FIG. 9 upper panel shows suspensions after two months storage and after two months storage followed by thirty inversions. No polymorphic changes were observed and the particle size distribution of the CR845 embedded in trehalose also remained stable after one and two months of storage at 40° C./75% RH as shown by microscopic examination: FIG. 9 lower panel.

Example 114: Pharmacokinetics of CR845 Formulations Administered in Trehalose-Embedded Particles of CR845.HCl Suspended in Miglyol® 812N Bioactivity of formulations 8-12 were determined as described above. Compositions of the formulations are shown in Table 5 below:

TABLE 5

| Formulation: | Suspension Matrix | CR845.HCl (% w/w) | Trehalose (% w/w) | Na Caprate (% w/w) | EDTA (% w/w) |
|---|---|---|---|---|---|
| 8. | 10% Capric acid/Miglyol ® | 23.17 | 76.83 | 0.00 | 0.00 |
| 9. | Miglyol ® | 18.81 | 62.37 | 14.11 | 4.70 |
| 10. | Miglyol ® | 17.92 | 59.91 | 12.74 | 9.43 |
| 11. | Miglyol ® | 17.92 | 59.91 | 22.17 | 0.00 |
| 12. | 10% Capric acid/Miglyol ® | 20.99 | 69.68 | 0.00 | 9.33 |

FIGS. 10-14 show bioactivity profiles for formulations 8-12. Table 6 shows the bioactivity determined as described above for each of these formulations:

TABLE 6

| Formulation: | Suspension Matrix | % f | Std. Dev. | SEM |
|---|---|---|---|---|
| 8. | 10% Capric acid/Miglyol ® | 16.3 | 14.92 | 5.27 |
| 9. | Miglyol ® | 11.5 | 6.07 | 2.15 |
| 10. | Miglyol ® | 12.4 | 8.95 | 3.17 |
| 11. | Miglyol ® | 18.4 | 11.64 | 4.11 |
| 12. | 10% Capric acid/Miglyol ® | 14.5 | 10.89 | 3.85 |

The specifications of each of the U.S. patents and published patent applications, and the texts of the literature references cited in this specification are herein incorporated by reference in their entireties. In the event that any definition or description contained found in one or more of these references is in conflict with the corresponding definition or description herein, then the definition or description disclosed herein is intended.

The examples provided herein are for illustration purposes only and are not intended to limit the scope of the invention, the full breadth of which will be readily recognized by those of skill in the art.

What is claimed is:

1. A formulation for oral delivery of a kappa opioid receptor agonist, the formulation comprising:
   particles comprising a mixture of about 18% to about 23% (w/w) kappa opioid receptor agonist and about 60% to about 77% (w/w) trehalose, wherein the kappa opioid receptor agonist is D-Phe-D-Phe-D-Arg-D-Lys-ω(4-aminopiperidine-4-carboxylic acid).HCl, (CR845.HCl); and wherein the particles are suspended in a liquid suspension,
   wherein the liquid suspension comprises about 0.01% to about 5% (w/w) of the kappa opioid receptor agonist and about 60% to about 100% (w/w) of an absorption enhancer;
   wherein the absorption enhancer comprises:
      a medium chain fatty acid triglyceride comprising 55% to 60% (w/w) caprylic acid, 40% to 45% (w/w) capric acid; or
      a mixture consisting of 10% capric acid and 90% of a medium chain fatty acid triglyceride comprising 55% to 60% (w/w) caprylic acid, 40% to 45% (w/w) capric acid.

2. The formulation according to claim 1, wherein the CR845.HCl, of the formulation retains at least about 98% purity over a period of 4 months at 40° C., 75% relative humidity.

3. The formulation according to claim 1, further comprising a pharmaceutical diluent, excipient or carrier.

4. The formulation according to claim 1, further comprising a salt of a carboxylic acid, or an additional absorption enhancer, or both.

5. The formulation according to claim 4, wherein the salt of a carboxylic acid comprises sodium citrate.

6. The formulation according to claim 4, wherein the additional absorption enhancer comprises a salt of a medium chain fatty acid, a chelating agent, or both.

7. The formulation according to claim 6, wherein the salt of the medium chain fatty acid comprises sodium caprate.

8. The formulation according to claim 4, wherein the chelating agent comprises EDTA.

9. The formulation according to claim 1, wherein the kappa opioid receptor agonist of the formulation retains at least about 98% purity over a period of at least a year at 25° C.

10. The formulation according to claim 1, wherein the particles comprising the mixture of CR845.HCl and trehalose are spray dried particles.

11. The formulation according to claim 1, wherein the particles comprising the kappa opioid receptor agonist and trehalose comprise about 0.25% of the liquid suspension.

12. A formulation for oral delivery of a kappa opioid receptor agonist, the formulation comprising:
   particles comprising a mixture of about 18% to about 23% (w/w) kappa opioid receptor agonist and about 60% to about 77% (w/w) trehalose, wherein the kappa opioid receptor agonist is D-Phe-D-Phe-D-Arg-D-Lys-ω(4-aminopiperidine-4-carboxylic acid).HCl, (CR845.HCl); and wherein the particles are suspended in a liquid suspension,
   wherein the liquid suspension comprises about 0.01% to about 5% (w/w) of the kappa opioid receptor agonist and an absorption enhancer;
   wherein the absorption enhancer comprises: from about 25% to about 92% (w/w) medium-chain triglycerides of 55% caprylic/45% capric fatty acids; and from about 5% to about 50% (w/w) capric acid.

13. The formulation according to claim 12, comprising from about 0.1% to about 1% (w/w) CR845.HCl; from about 60% to about 90% (w/w) medium-chain triglycerides of 55% caprylic, 45% capric fatty acids; and from about 10% to about 40% (w/w) capric acid.

14. The formulation according to claim 12, comprising 0.5% (w/w) CR845.HCl; about 70% (w/w) medium-chain triglycerides of 55% caprylic, 45% capric fatty acids; and 30% (w/w) capric acid.

15. The formulation according to claim 12, comprising 0.5% (w/w) CR845.HCl; 90% (w/w) medium-chain triglycerides of 55% caprylic, 45% capric fatty acids; and 10% (w/w) capric acid.

16. The formulation according to claim 12, comprising from about 0.1% to about 1% (w/w) CR845.HCl; from about 60% to about 95% (w/w) medium-chain triglycerides of 55% caprylic, 45% capric fatty acids; and from about 1% to about 20% (w/w) sodium caprate.

17. The formulation according to claim 12, comprising about 0.5% (w/w) CR845.HCl; about 90% (w/w) medium-chain triglycerides of 55% caprylic, 45% capric fatty acids; and about 10% (w/w) sodium caprate.

18. A pharmaceutically acceptable caplet, capsule, gel or lozenge comprising the liquid suspension of the formulation according to claim 1.

19. The pharmaceutically acceptable caplet, capsule, gel or lozenge according to claim 18 wherein the caplet, capsule, gel or lozenge is enterically coated.

20. A formulation for oral delivery of a kappa opioid receptor agonist, the formulation comprising:
   particles comprising a mixture of about 18% to about 23% (w/w) kappa opioid receptor agonist and about 60% to about 77% (w/w) trehalose; and wherein the particles are suspended in a liquid suspension,
wherein the liquid suspension comprises about 0.01% to about 5% (w/w) of the kappa opioid receptor agonist and about 60% to about 100% (w/w) of an absorption enhancer;
wherein the absorption enhancer comprises:
   a medium chain fatty acid triglyceride comprising 55% to 60% (w/w) caprylic acid, 40% to 45% (w/w) capric acid and optionally further optionally comprising about 13% to about 22% sodium caprate and/or about 5% to 9% EDTA; or
   a mixture consisting of 10% capric acid and 90% of a medium chain fatty acid triglyceride comprising 55% to 60% (w/w) caprylic acid, 40% to 45% (w/w) capric acid;
   and optionally further optionally comprising about 13% to about 22% sodium caprate and/or about 5% to 9% EDTA;
wherein the kappa opioid receptor agonist is:
D-Phe-D-Phe-D-Leu-D-Lys-[ω(4-aminopiperidine-4-carboxylic acid)]-OH, (CR845.HCl).

\* \* \* \* \*